US010125212B2

(12) United States Patent
Shinohata et al.

(10) Patent No.: US 10,125,212 B2
(45) Date of Patent: Nov. 13, 2018

(54) POLYISOCYANATE COMPOSITION AND ISOCYANATE POLYMER COMPOSITION

(71) Applicant: Asahi Kasei Kabushiki Kaisha, Tokyo (JP)

(72) Inventors: Masaaki Shinohata, Tokyo (JP); Nobuhisa Miyake, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/425,671

(22) PCT Filed: Oct. 31, 2013

(86) PCT No.: PCT/JP2013/079639
§ 371 (c)(1),
(2) Date: Mar. 4, 2015

(87) PCT Pub. No.: WO2014/069605
PCT Pub. Date: May 8, 2014

(65) Prior Publication Data
US 2015/0210631 A1    Jul. 30, 2015

(30) Foreign Application Priority Data

Nov. 1, 2012  (JP) ................................. 2012-242136
Nov. 1, 2012  (JP) ................................. 2012-242139
Nov. 1, 2012  (JP) ................................. 2012-242141

(51) Int. Cl.
| | | |
|---|---|---|
| C08G 18/02 | (2006.01) |
| C08G 18/81 | (2006.01) |
| C08G 18/08 | (2006.01) |
| C07C 263/18 | (2006.01) |
| C07C 263/20 | (2006.01) |
| C07C 271/52 | (2006.01) |
| C07C 265/14 | (2006.01) |
| C07C 271/56 | (2006.01) |
| C07C 271/20 | (2006.01) |

(52) U.S. Cl.
CPC .......... *C08G 18/022* (2013.01); *C07C 263/18* (2013.01); *C07C 263/20* (2013.01); *C07C 265/14* (2013.01); *C07C 271/20* (2013.01); *C07C 271/52* (2013.01); *C07C 271/56* (2013.01); *C08G 18/027* (2013.01); *C08G 18/08* (2013.01); *C08G 18/0809* (2013.01); *C08G 18/0842* (2013.01); *C08G 18/8125* (2013.01); *C07C 2601/14* (2017.05)

(58) Field of Classification Search
CPC . C07C 2101/14; C07C 263/16; C07C 265/14; C07C 271/52; C07C 271/56; C07C 263/18; C07C 263/20
USPC .......... 560/336, 355, 331, 332, 333
See application file for complete search history.

(56) References Cited

U.S. PATENT DOCUMENTS

| | | | | |
|---|---|---|---|---|
| 2,885,420 | A | * | 5/1959 | Spiegler ................ C07C 265/14 252/406 |
| 2,885,423 | A | * | 5/1959 | Spiegler ................ C07C 265/14 252/407 |
| 2,885,424 | A | | 5/1959 | Spiegler |
| 3,281,444 | A | * | 10/1966 | Manning ............... C07C 265/14 560/331 |
| 3,585,230 | A | * | 6/1971 | Woycheshin ........ C08G 18/708 521/111 |
| 3,976,622 | A | | 8/1976 | Wagner et al. |
| 4,152,348 | A | | 5/1979 | Rabourn |
| 4,176,132 | A | | 11/1979 | Ide et al. |
| 4,290,969 | A | | 9/1981 | Komatsu et al. |
| 4,324,879 | A | | 4/1982 | Bock et al. |
| 4,412,073 | A | | 10/1983 | Robin |
| 4,677,221 | A | | 6/1987 | Muller et al. |
| 4,837,359 | A | | 6/1989 | Woynar et al. |
| 4,983,762 | A | | 1/1991 | Robin |

(Continued)

FOREIGN PATENT DOCUMENTS

| | | |
|---|---|---|
| CA | 2074226 A1 | 1/1993 |
| CA | 2130684 A1 | 3/1995 |

(Continued)

OTHER PUBLICATIONS

Creasy ("Study of detection limits and quantitation accuracy using 300 MHZ NMR" http://www.dtic.mil/dtic/tr/fulltext/u2/a482893.pdf, Jul. 1, 2003, p. 1-6).*
NMR ("Sensitivity in NMR", https://www.chem.wisc.edu/~cic/nmr/Guides/Other/sensitivity-NMR.pdf, Oct. 26, 2009, p. 1-2).*
International Search Report issued in corresponding International Patent Application No. PCT/JP2013/079639 dated Feb. 4, 2014.
Supplementary European Search Report issued in corresponding European Patent Application No. 13851480 dated Sep. 1, 2015.
European Search Report issued in counterpart European Patent Application No. 18164645.6 dated Jul. 17, 2018.

*Primary Examiner* — Jafar F Parsa
*Assistant Examiner* — Amy C Bonaparte
(74) *Attorney, Agent, or Firm* — Morgan, Lewis & Bockius LLP

(57) ABSTRACT

The present invention relates to a polyisocyanate composition comprising, on the basis of the total mass of the polyisocyanate composition, 97 weight % or more of a polyisocyanate, and 2.0 mass ppm or more and $1.0 \times 10^4$ mass ppm or less of a compound having at least one unsaturated bond in which the compound is a different compound from the polyisocyanate, or 5.0 mass ppm or more and $2.0 \times 10^4$ mass ppm or less of at least one inactive compound selected from the group consisting of a hydrocarbon compound, an ether compound, a sulfide compound, a halogenated hydrocarbon compound, a Si-containing hydrocarbon compound, a Si-containing ether compound, and a Si-containing sulfide compound.

9 Claims, No Drawings

(56) References Cited

U.S. PATENT DOCUMENTS

| | | | |
|---|---|---|---|
| 4,994,541 A | 2/1991 | Dell et al. | |
| 5,144,031 A | 9/1992 | Pedain | |
| 5,278,317 A | 1/1994 | Hagen et al. | |
| 5,386,054 A | 1/1995 | Scholl et al. | |
| 5,641,851 A | 6/1997 | Wolff et al. | |
| 5,728,317 A * | 3/1998 | Laqua | C07C 263/18 252/182.29 |
| 5,808,138 A | 9/1998 | Laqua et al. | |
| 6,392,001 B1 | 5/2002 | Mertes et al. | |
| 6,765,111 B1 | 7/2004 | Pedain et al. | |
| 8,658,819 B2 | 2/2014 | Shinohata et al. | |
| 2003/0078450 A1 | 4/2003 | Kocher et al. | |
| 2010/0022707 A1 | 1/2010 | Schaefer et al. | |
| 2010/0069665 A1 * | 3/2010 | Shinohata | C07C 263/04 560/345 |
| 2011/0054211 A1 | 3/2011 | Shinohata et al. | |
| 2011/0133121 A1 | 6/2011 | Shinohata et al. | |
| 2011/0251423 A1 | 10/2011 | Binder et al. | |
| 2012/0271067 A1 * | 10/2012 | Shimokawatoko | C07C 29/12 564/393 |
| 2013/0178645 A1 | 7/2013 | Shinohata et al. | |
| 2013/0184488 A1 * | 7/2013 | Shinohata | C07C 263/04 560/345 |

FOREIGN PATENT DOCUMENTS

| | | | |
|---|---|---|---|
| CA | 2806533 A1 | | 4/2012 |
| CN | 101165048 A | | 4/2008 |
| CN | 102471244 A | | 5/2012 |
| DE | 4232769 | * | 3/1994 |
| EP | 0183976 A1 | | 10/1985 |
| EP | 0330966 A2 | | 2/1989 |
| EP | 0456062 A2 | | 4/1991 |
| EP | 0524507 A1 | | 7/1992 |
| EP | 0538500 A1 | | 4/1993 |
| EP | 0581100 A1 | | 2/1994 |
| EP | 0643042 A1 | | 9/1994 |
| EP | 2626345 A1 | | 8/2013 |
| GB | 994890 | | 6/1965 |
| GB | 1186896 | | 4/1970 |
| JP | S54-125616 A | | 9/1979 |
| JP | S57-047319 A | | 3/1982 |
| JP | S61-115059 A | | 6/1986 |
| JP | S63-057577 A | | 3/1988 |
| JP | H02-003682 A | | 1/1990 |
| JP | H02-228317 A | | 9/1990 |
| JP | H04-226966 A | | 8/1992 |
| JP | H04-253951 A | | 9/1992 |
| JP | H05-194353 A | | 8/1993 |
| JP | H07-149705 A | | 6/1995 |
| JP | H07-304724 A | | 11/1995 |
| JP | H08-291129 A | | 11/1996 |
| JP | H11-246508 A | | 9/1999 |
| JP | 2000-119240 A | | 4/2000 |
| JP | 2004-099523 A | | 4/2004 |
| JP | 2010-522715 A | | 7/2010 |
| JP | 2012-506465 A | | 3/2012 |
| JP | 2012-153708 A | | 8/2012 |
| TW | 200844080 A | | 11/2008 |
| TW | 201219346 A1 | | 5/2012 |
| WO | 2008/084824 A1 | | 7/2008 |
| WO | 2009/139061 A1 | | 11/2009 |
| WO | 2012/046734 A1 | | 4/2012 |
| WO | WO 2012/046734 | * | 4/2012 |
| WO | 2012/115110 A1 | | 8/2012 |

* cited by examiner

POLYISOCYANATE COMPOSITION AND ISOCYANATE POLYMER COMPOSITION

TECHNICAL FIELD

The present invention relates to a polyisocyanate composition, and an isocyanate polymer composition manufactured by using the polyisocyanate composition.

BACKGROUND ART

A polyurethane having a urethane bond is manufactured mainly by a reaction of a bi- or higher functional isocyanate and a bi- or higher functional alcohol, is a polymer which excels in tensile strength, abrasion resistance, and oil resistance, and is used in a wide range of fields such as flexible foam, rigid foam, elastomer, an adhesive, a coating material, and a binder. Among them, a polyurethane made mainly from a chain or cyclic aliphatic isocyanate excels in weatherability and light resistance, and is used for fields requiring quality of appearance, such as baking coating, an automotive clear coating material, and coil coating material.

As the isocyanate, there is a case where a diisocyanate that is a bifunctional isocyanate is used, or there is a case where, for the purpose of improving physical properties and suppressing vapor pressure of a polyurethane to secure safety of workers, a diisocyanate is polymerized by reactions represented by formulas (a) to (c) to be used as an isocyanate polymer.

[Chemical Formula 1]

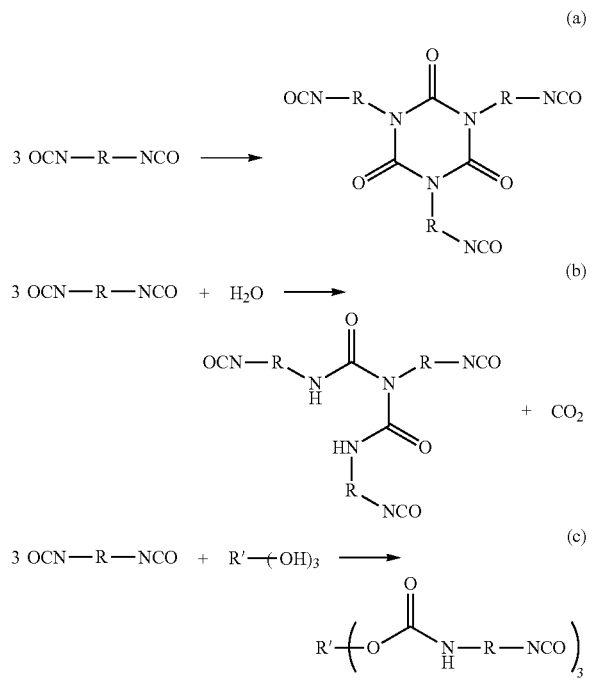

In the formulas, R represents a divalent organic group, and R' represents a trivalent organic group.

An isocyanurate type isocyanate polymer is obtained in the reaction represented by formula (a), a biuret type isocyanate polymer is obtained in the reaction represented by formula (b), and a urethane type isocyanate polymer is obtained in the reaction represented by formula (c).

The biuret type isocyanate polymer is disclosed in Patent Literatures 1 to 6. The isocyanurate type isocyanate polymer is disclosed in Patent Literatures 7 to 10. An allophanate type isocyanate polymer is disclosed in Patent Literatures 11 and 12.

As described above, when being used for fields requiring quality of appearance, a polyurethane is required to be little colored. Therefore, it is important that not only coloration does not occur in a polyurethane-forming reaction but also an isocyanate (bi- or higher functional polyisocyanate) as a raw material is little colored. However, generally, an isocyanate tends to be oxidized by oxygen or the like in the air to be easily altered or colored. Moreover, when manufacturing an isocyanate polymer by polymerization of a diisocyanate, coloration of an isocyanate tends to easily occur due to a catalyst or a solvent used in the polymerization reaction.

Examples of a method for suppressing coloration of an isocyanate include a manufacturing and storing method by sealing with nitrogen gas for air shutoff, and a storing method by adding an ultraviolet absorbing agent, an anti-oxidizing agent and the like. For example, in order to manufacture a polyisocyanate for light-colored polyurethane lacquer, a treatment method with a peroxide after denaturation of an isocyanate is disclosed in Patent Literature 13. Moreover, a method for manufacturing an isocyanate whose coloration is reduced by contacting a colored isocyanate with ozone-containing gas is studied in Patent Literature 14. Furthermore, a method for manufacturing an isocyanate whose coloration is reduced by irradiating a colored isocyanate with light having a wavelength of 200 to 600 nm is also studied in Patent Literature 15.

CITATION LIST

Patent Literature

Patent Literature 1: U.S. Pat. No. 3,976,622 A
Patent Literature 2: U.S. Pat. No. 4,176,132 A
Patent Literature 3: U.S. Pat. No. 4,290,969 A
Patent Literature 4: U.S. Pat. No. 4,837,359 A
Patent Literature 5: U.S. Pat. No. 4,983,762 A
Patent Literature 6: U.S. Pat. No. 5,641,851 A
Patent Literature 7: U.S. Pat. No. 4,324,879 A
Patent Literature 8: U.S. Pat. No. 4,412,073 A
Patent Literature 9: JP 57-47139 A
Patent Literature 10: JP 63-57577 A
Patent Literature 11: GB 994890 A
Patent Literature 12: JP 7-304724 A
Patent Literature 13: JP 2-228317 A
Patent Literature 14: JP 8-291129 A
Patent Literature 15: WO 2012-506465 A1

SUMMARY OF INVENTION

Technical Problem

As described above, various methods have been studied so as to suppress coloration of an isocyanate, but in a storing method by adding a compound unnecessary for a polymerization reaction to an isocyanate, the added compound may become the cause of coloration in manufacturing a polyurethane or the like.

Moreover, the coloration is not necessarily sufficiently reduced by methods disclosed in Patent Literatures 4 to 6, and an isocyanate whose coloration is further reduced is required. Furthermore, although distillation purification is common as a purification method of a compound, the isocyanate is heated in the distillation purification, and thus, the coloration of the isocyanate may proceed or the alteration of the isocyanate may occur.

In view of the circumstances, it is an object of the present invention to provide a manufacturing method of a distillation-purified isocyanate capable of obtaining a polyisocyanate whose coloration is sufficiently suppressed, and a polyisocyanate composition for performing it. Moreover, it is an object of the present invention to provide a manufacturing method of an isocyanate polymer whose coloration is suppressed by polymerization of a polyisocyanate, and a polyisocyanate composition for performing it.

Solution to Problem

The present inventors made extensive research so as to solve the above-described subjects, and found that an isocyanate composition whose coloration is sufficiently suppressed is obtained by distillation separating an isocyanate by a distillation purification method using an isocyanate composition comprising a specific constituent and that an isocyanate polymer whose coloration is sufficiently suppressed can be manufactured by a manufacturing method using the isocyanate composition to complete the present invention.

That is, the present invention relates to the following substances.

[1] A polyisocyanate composition comprising, on the basis of a total mass of the polyisocyanate composition: 97 wt. % or more of a polyisocyanate; and 2.0 mass ppm or more and $1.0 \times 10^4$ mass ppm or less of a compound having at least one unsaturated bond in which the compound is a different compound from the polyisocyanate, or 5.0 mass ppm or more and $2.0 \times 10^4$ mass ppm or less of at least one inactive compound selected from the group consisting of a hydrocarbon compound, an ether compound, a sulfide compound, a halogenated hydrocarbon compound, a Si-containing hydrocarbon compound, a Si-containing ether compound, and a Si-containing sulfide compound.

[2] The composition according to [1], comprising the polyisocyanate, and the compound having at least one unsaturated bond, wherein the unsaturated bond is a carbon-carbon double bond or a carbon-oxygen double bond, and the carbon-carbon double bond is not a carbon-carbon double bond that constitutes an aromatic ring.

[3] The composition according to [2], wherein the compound having at least one unsaturated bond comprises a carbonic acid derivative.

[4] The composition according to [3], wherein the carbonic acid derivative is at least one carbonic acid ester selected from the group consisting of dimethyl carbonate, diethyl carbonate, dibutyl carbonate, dipentyl carbonate, and dihexyl carbonate, or an N-unsubstituted carbamic acid ester.

[5] The composition according to [3] or [4], wherein the compound having at least one unsaturated bond further comprises a compound represented by formula (1):

[Chemical Formula 2]

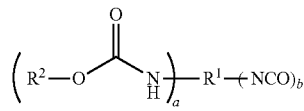

(1)

wherein $R^1$ and $R^2$ each independently represents an organic group, a represents an integer of 1 to 5, b represents an integer of 0 to 4, and the sum of a and b is 2 to 5.

[6] The composition according to [5], further comprising at least one inactive compound selected from the group consisting of the hydrocarbon compound, the ether compound, the sulfide compound, the halogenated hydrocarbon compound, the Si-containing hydrocarbon compound, the Si-containing ether compound, and the Si-containing sulfide compound.

[7] The composition according to [1], comprising the polyisocyanate, and the compound having at least one unsaturated bond, wherein the compound having at least one unsaturated bond comprises a compound represented by formula (1):

[Chemical Formula 3]

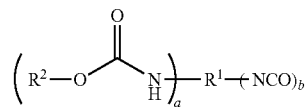

(1)

wherein $R^1$ and $R^2$ each independently represents an organic group, a represents an integer of 1 to 5, b represents an integer of 0 to 4, and the sum of a and b is 2 to 5.

[8] The composition according to [7], further comprising at least one inactive compound selected from the group consisting of the hydrocarbon compound, the ether compound, the sulfide compound, the halogenated hydrocarbon compound, the Si-containing hydrocarbon compound, the Si-containing ether compound, and the Si-containing sulfide compound.

[9] The composition according to [1], comprising the polyisocyanate, and at least one inactive compound selected from the group consisting of the hydrocarbon compound, the ether compound, the sulfide compound, the halogenated hydrocarbon compound, the Si-containing hydrocarbon compound, the Si-containing ether compound, and the Si-containing sulfide compound.

[10] The composition according to [9], further comprising the compound having at least one unsaturated bond, wherein the unsaturated bond is a carbon-carbon double bond or a carbon-oxygen double bond, and the carbon-carbon double bond is not a carbon-carbon double bond that constitutes an aromatic ring.

[11] The composition according to [10], wherein the compound having at least one unsaturated bond comprises a carbonic acid derivative.

[12] The composition according to [11], wherein the carbonic acid derivative is at least one carbonic acid ester selected from the group consisting of dimethyl carbonate, diethyl carbonate, dibutyl carbonate, dipentyl carbonate, and dihexyl carbonate, or an N-unsubstituted carbamic acid ester.

[13] The composition according to [5] or [7], wherein the compound represented by formula (1) is a compound represented by formula (1-3) or (1-4):

[Chemical Formula 4]

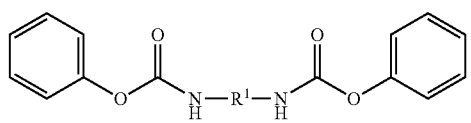

(1-3)

-continued

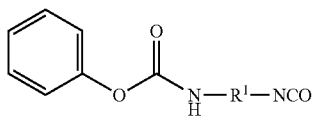
(1-4)

wherein $R^1$ each independently represents an organic group.

[14] The composition according to [13], wherein the $R^1$ is a hexamethylene group.

[15] The composition according to [6], [8] or [9], wherein the inactive compound is at least one compound selected from the group consisting of benzyltoluene, dibenzyl ether, and hexadecane.

[16] The composition according to [2] or [10], wherein the compound having at least one unsaturated bond is at least one compound selected from the group consisting of styrene, α-methylstyrene, pentene, and octene.

[17] A method for preventing coloration in distillation purification of a polyisocyanate, comprising: a step of adding, on the basis of a total mass of the polyisocyanate, 2.0 mass ppm or more and $1.0 \times 10^4$ mass ppm or less of a compound having at least one unsaturated bond in which the compound is a different compound from the polyisocyanate, to the polyisocyanate before the distillation purification.

[18] A polyisocyanate composition comprising the polyisocyanate distillation-purified by the method according to [17].

[19] A manufacturing method of an isocyanate polymer comprising reacting the polyisocyanate comprised in the composition according to any one of [1] to [16] and [18], wherein the polyisocyanate comprised in the composition is a diisocyanate, the isocyanate polymer has a unit represented by formula (2) and at least one unit selected from the group consisting of units represented by formulas (3), (4), (5), (6), (7), (8) and (9), respectively, and a nitrogen atom constituting the isocyanate polymer is bonded to a carbon atom:

[Chemical Formula 5]

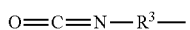
(2)

[Chemical Formula 6]

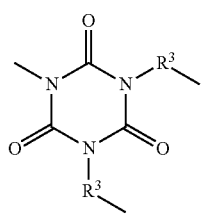
(3)

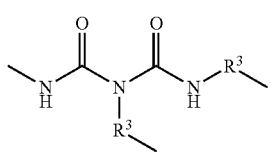
(4)

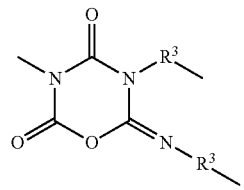
(5)

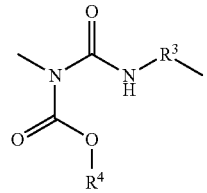
(6)

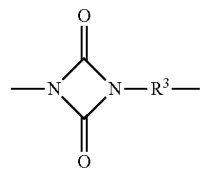
(7)

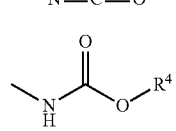

—N=C=O (8)

(9)

wherein $R^3$ each independently represents a divalent hydrocarbon group, and $R^4$ each independently represents a monovalent organic group.

[20] A composition comprising the isocyanate polymer manufactured by the method according to [19].

Advantageous Effects of Invention

According to the present invention, a manufacturing method of a purified polyisocyanate capable of obtaining a polyisocyanate whose coloration is sufficiently suppressed, and a polyisocyanate composition for performing it are provided. Moreover, according to the present invention, a method for suppressing coloration in distillation purification of a polyisocyanate is provided.

DESCRIPTION OF EMBODIMENTS

Hereinafter, preferred embodiments of the present invention will be described. It is to be noted that the present invention is not limited to the following embodiments and may be performed in various ways within the scope of the present invention.

In the present specification, the IUPAC Rules, and the Nomenclature Rules prescribed by IUPAC also described hereinafter (except the case where other years' IUPAC Recommendations and the like are specially cited) mean those cited from "Organic Chemistry and Biochemistry Nomenclature (Japan, Nankodo Co., Ltd., revised second edition published in 1992)", which is based on the edition including all rules of organic chemistry and biochemistry, and Japanese transliteration rules, published as a separate volume of "Kagaku no Ryoiki" in 1980, based on Recommendations 1979, and to which all subsequent revisions and recommendations are added. "Organic" refers to generally a group of compounds that are subjects of the nomenclature disclosed in the Nomenclature. The subjects may be subjects described in Recommendations issued in 1993. In addition, the "organic" compounds that are subjects of the above-described Nomenclature also include organometallic compounds and metal complexes. In the present embodiments, the terms "organic groups", "substituent groups" and the like mean groups composed of atoms not including metal atoms and/or semimetals, unless otherwise explained. Furthermore, in the present embodiments, preferably, "organic compounds", "organic groups", or "substituent groups" composed of atoms selected from H (hydrogen atom), C (carbon atom), N (nitrogen atom), O (oxygen atom), S (sulfur atom), Cl (chlorine atom), Br (bromine atom), and I (iodine atom) are used.

In the explanation below, the terms "aliphatic" and "aromatic" are frequently used. The above-described IUPAC Rules describes that organic compounds are classified into aliphatic compounds and aromatic compounds. The aliphatic compounds are the definition of groups according to aliphatic compounds based on IUPAC Recommendations 1995. In the Recommendations, aliphatic compounds are defined as "Acyclic or cyclic, saturated or unsaturated carbon compounds, excluding aromatic compounds". Moreover, "aliphatic compounds" used in the explanation of the present embodiments include any of saturated and unsaturated, and chain and cyclic, and mean the above-described "organic compounds", "organic groups", or "substituent groups" composed of atoms selected from H (hydrogen atom); C (carbon atom); N (nitrogen atom); O (oxygen atom); S (sulfur atom); Si (silicon atom); and a halogen atom selected from Cl (chlorine atom), Br (bromine atom), and I (iodine atom).

The case where an aromatic group is bonded to an aliphatic group, such as an aralkyl group, is sometimes described as "an aliphatic group substituted with an aromatic group" or "a group composed of an aliphatic group to which an aromatic group is bonded" in such a manner. This is based on reactivity in the present embodiments, and the property regarding the reaction of a group, such as an aralkyl group, is closely similar to the reactivity of an aliphatic group rather than aromaticity. Furthermore, a non-aromatic reactive group including an aralkyl group and an alkyl group is sometimes described as "an aliphatic group which may be substituted with an aromatic group", "an aliphatic group to which an aromatic group may be bonded" or the like.

In addition, when general formulas of compounds used in the present specification are explained, definitions according to the above-described Nomenclature Rules defined by IUPAC are used, but for specific names of groups and names of the exemplified compounds, trivial names are sometimes used. Furthermore, when the number of atoms, the number of substituent groups, and the number are described in the present specification, all of them represent an integer.

In the present specification, "active hydrogen" means a hydrogen atom bonded to an oxygen atom, a sulfur atom, a nitrogen atom, a silicon atom or the like (except aromatic hydroxy group), and a hydrogen atom of a terminal methine group. The "active hydrogen" is hydrogen contained in an atomic group, such as a —C(=O)OH group, a —C(=O)H group, a —SH group, a —SO$_3$H group, a —SO$_2$H group, a —SOH group, an —NH$_2$ group, an —NH— group, a —SiH group, and a —C≡CH group. In addition, a hydrogen atom contained in a hydroxy group (—OH group) is included in the definition of the above-described "active hydrogen", but the hydroxy group (—OH group) is not included in groups containing the "active hydrogen", unless otherwise described. Examples of a compound having a hydroxy group include alcohols and aromatic hydroxy compounds.

"Alcohols" in the present specification are "Compounds in which a hydroxy group, —OH, is attached to a saturated carbon atom: R$_3$COH" described in the definition of IUPAC (Rule C-201), and do not include aromatic hydroxy compounds in which a hydroxy group is bonded to an aromatic ring.

"Aromatic hydroxy compounds" in the present specification are phenols, "Compounds having one or more hydroxy groups attached to a benzene or other arene ring", described in the definition of IUPAC (Rule C-202).

"An unsaturated bond" in the present specification means one in which a chemical bond between two atoms is formed by two or three covalent bonds, and is a term including a double bond and a triple bond (Chemistry Dictionary 7 pocket edition (Kyoritsu Shuppan Co., Ltd., issued in Oct. 1, 2003). Examples of the unsaturated bond include C=C, C≡C, C=O, C=N, C≡N, N=N, and N=O.

A compound comprised in a polyisocyanate composition of the present embodiment will be described.

<Polyisocyanate>

A polyisocyanate according to the present embodiment is not particularly limited as long as it is a compound having two or more isocyanate groups, but a compound represented by formula (10) is preferably used.

[Chemical Formula 7]

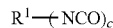

(10)

In the formula, c represents an integer of 2 to 5, and R$^1$ represents a c-valent organic group.

R$^1$ is preferably an organic group having 1 to 85 carbon atoms.

R$^1$ represents an aliphatic group, an aromatic group, or a group formed by combining an aliphatic group and an aromatic group, and specifically, examples thereof include cyclic groups such as cyclic hydrocarbon groups (a monocyclic hydrocarbon group, a condensed polycyclic hydrocarbon group, a cross-linked cyclic hydrocarbon group, a spiro hydrocarbon group, a ring assembly hydrocarbon group, and a cyclic hydrocarbon group having a side chain), hetero ring groups, hetero cyclic spiro groups, and hetero cross-linked ring groups, acyclic hydrocarbon groups, groups bonded to one or more groups selected from acyclic hydrocarbon groups and cyclic groups, and groups to which the above-described group is bonded through a covalent bond with a specific non-metal atom (carbon, oxygen, nitrogen, sulfur or silicon).

The covalent bond with a specific non-metal atom is, for example, a state in which the above-described group is bonded to any of groups represented by formulas (11) to (19) by a covalent bond.

[Chemical Formula 8]

(11)

(12)

-continued

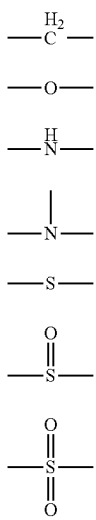

(13)
(14)
(15)
(16)
(17)
(18)
(19)

From the viewpoint of difficulty in occurrence of side reactions, the $R^1$ group that can be preferably used in the present embodiment is a group selected from an aliphatic group, an aromatic group, or a group formed by combining an aliphatic group and an aromatic group, and selected from the group consisting of acyclic hydrocarbon groups, and cyclic hydrocarbon groups (a monocyclic hydrocarbon group, a condensed polycyclic hydrocarbon group, a cross-linked cyclic hydrocarbon group, a spiro hydrocarbon group, a ring assembly hydrocarbon group, and a cyclic hydrocarbon group having a side chain), groups to which at least one group selected from the above-described groups is bonded (mutually-substituted group), and having 1 to 85 carbon atoms. From the viewpoint of fluidity and the like, a group having 1 to 70 carbon atoms is preferable. A group having 1 to 13 carbon atoms is further preferable.

Preferred examples of the polyisocyanate represented by formula (10) are 1) an aromatic polyisocyanate in which the $R^1$ group is a group having 6 to 85 carbon atoms and containing one or more aromatic rings which may be substituted with aliphatic groups and/or aromatic groups, aromatic groups in the $R^1$ group are substituted with isocyanate groups, and c is an integer of 2 to 5, and 2) an aliphatic polyisocyanate in which the $R^1$ group is an aliphatic group having 1 to 85 carbon atoms, which may be substituted with an aromatic group, and c is 2 or 3.

The case where the atom to which the isocyanate group is bonded (preferably, carbon atom) is included in the aromatic ring is represented as an aromatic isocyanate, and the case where it is bonded to the atom other than the aromatic ring (mainly carbon atom) is represented as an aliphatic isocyanate. A further preferable aliphatic group is an aliphatic group having 6 to 70 carbon atoms, and is a chain hydrocarbon group, a cyclic hydrocarbon group, and a group to which at least one group selected from the above-described chain hydrocarbon groups and the above-described cyclic hydrocarbon group is bonded (indicating a cyclic hydrocarbon group substituted with a chain hydrocarbon group, a chain hydrocarbon group substituted with a cyclic hydrocarbon group, and the like, for example).

Hereinafter, specific examples of a preferred polyisocyanate will be described.

1) Aromatic Polyisocyanate

The aromatic polyisocyanate is an aromatic polyisocyanate in which the $R^1$ group is a group having 6 to 85 carbon atoms and containing one or more aromatic rings which may be aliphatic and/or aromatic substituted, one or more hydrogen atoms of aromatic groups in the $R^1$ group are substituted with isocyanate groups, and a is 2. Preferably, it is an aromatic polyisocyanate in which the $R^1$ group is a group having 6 to 70 carbon atoms and c is an integer of 2 to 5, and from the viewpoint of fluidity and the like, further preferably, it is an aromatic polyisocyanate in which the $R^1$ group is a group having 6 to 13 carbon atoms and containing one or more aromatic rings which are "substituted with isocyanate groups", and c is an integer of 2 to 5, and the above-described aromatic rings may be further substituted with alkyl groups, aryl groups, and aralkyl groups.

Examples of the aromatic polyisocyanate include diisocyanatobenzene, diisocyanatotoluene, diphenylmethane diisocyanate, diisocyanatomesitylene, diisocyanatobiphenyl, diisocyanatodibenzyl, bis(isocyanatophenyl)propane, bis(isocyanatophenyl)ether, bis(isocyanatophenoxyethane), diisocyanato xylene, diisocyanato anisole, diisocyanato phenetole, diisocyanatonaphthalene, diisocyanato-methylbenzene, diisocyanato-methylpyridine, diisocyanato-methylnaphthalene, and polymethylene polyphenyl polyamine represented by formula (20).

[Chemical Formula 9]

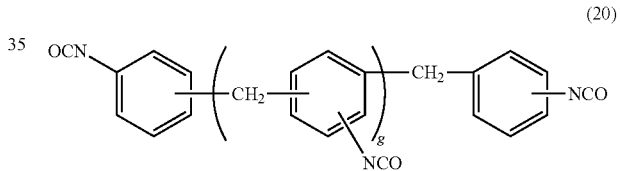

(20)

In the formula, g is an integer of 0 to 6.

2) Aliphatic Polyisocyanate

The polyisocyanate represented by formula (10) is an aliphatic polyisocyanate in which the $R^1$ group is an aliphatic group having 1 to 85 carbon atoms, and c is 2 or 3. The above-described aliphatic group may be further substituted with an aromatic group. A further preferred polyisocyanate is an aliphatic polyisocyanate in which the above-described aliphatic group is a chain hydrocarbon group, a cyclic hydrocarbon group, and a group composed of a chain hydrocarbon group and a cyclic hydrocarbon group. More preferably, it is an aliphatic polyisocyanate in which the $R^1$ group is an aliphatic group which is an acyclic hydrocarbon group and a cyclic hydrocarbon group having 1 to 70 carbon atoms, and a group composed of an acyclic hydrocarbon group and a cyclic hydrocarbon group, and c is 2 or 3. From the viewpoint of fluidity and the like when industrially manufacturing in volume, most preferably, it is an aliphatic polyisocyanate in which the $R^1$ group is an acyclic hydrocarbon group and a cyclic hydrocarbon group having 6 to 13 carbon atoms, and a group composed of an acyclic hydrocarbon group and a cyclic hydrocarbon group. That is, the $R^1$ group is a linear-chain and/or branched-chain alkyl group, a cycloalkyl group, and a group composed of linear-chain and/or branched-chain alkyl group and the above-described cycloalkyl group.

Examples of the aliphatic polyisocyanate include aliphatic diisocyanates such as ethylene diisocyanate, diisocyanatopropane, diisocyanatobutane, diisocyanatopentane, diisocyanatohexane, and diisocyanatodecane; aliphatic triisocyanates such as triisocyanatohexane, triisocyanatononane, and triisocyanatodecane; substituted cyclic aliphatic isocyanates such as diisocyanatocyclobutane, diisocyanatocyclohexane, 3-isocyanatomethyl-3,5,5-trimethylcyclohexylisocyanate (also referred to as "isophorone diisocyanate"), and methylene bis(cyclohexylisocyanate).

Among these polyisocyanates, diisocyanates having two isocyanate groups in one molecule are preferable. From the viewpoint of being suitable for applications requiring weatherability and thermal yellowing resistance and being industrially easily-available, hexamethylene diisocyanate or isophorone diisocyanate is more preferable. The above-described polyisocyanates may be used alone or two or more kinds thereof may be used in combination.

<Compound Having Unsaturated Bond>

The polyisocyanate composition of the present embodiment comprises, together with the polyisocyanate, a compound having at least one unsaturated bond other than the polyisocyanate, and/or at least one compound selected from the group consisting of compound A to compound E described below.

The compound having an unsaturated bond according to the present embodiment (hereinafter, also referred to as "unsaturated bond compound") is preferably a compound in which the unsaturated bond is an unsaturated bond between carbon and carbon, an unsaturated bond between carbon and nitrogen, or an unsaturated bond between carbon and oxygen. Furthermore, from the viewpoint of stability of the compound, a compound in which the unsaturated bond is a double bond is preferable, and a carbon-carbon double bond (C=C) or a carbon-oxygen double bond (C=O) is more preferable.

Generally, the carbon-carbon double bond is sometimes a carbon-carbon double bond that constitutes an aromatic ring, but is preferably not a carbon-carbon double bond that constitutes an aromatic ring in the present embodiment.

Examples of the compound include a carbonic acid derivative, a compound represented by formula (1), and a compound represented by formula (21).

[Chemical Formula 10]

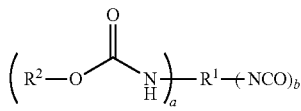

(1)

In the formula, $R^1$ and $R^2$ each independently represents an organic group, a represents an integer of 1 to 5, b represents an integer of 0 to 4, and the sum of a and b is 2 to 5.

[Chemical Formula 11]

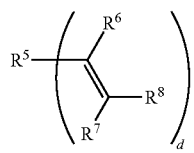

(21)

In the formula, $R^5$, $R^6$, $R^7$ and $R^8$ each independently represents a hydrogen atom, a halogen atom, or an organic group having 1 to 10 carbon atoms, $R^5$ to $R^8$ are not simultaneously hydrogen atoms, and d represents an integer of 1 to 3.

<Carbonic Acid Derivative>

The case where the unsaturated bond compound is a carbonic acid derivative will be described. The carbonic acid derivative according to the present embodiment means a compound represented by formula (22).

[Chemical Formula 12]

(22)

In the formula, X represents an amino group which may be substituted with an organic group having 1 to 20 carbon atoms, and Y represents an amino group which may be substituted with an organic group having 1 to 20 carbon atoms or an organic group having 0 to 20 carbon atoms.

Examples of the compound represented by formula (22) include a urea compound, an N-unsubstituted carbamic acid ester and a carbonic acid ester.

The urea compound is a compound having at least one urea bond in the molecule, preferably a compound having one urea bond, and represented by formula (23).

[Chemical Formula 13]

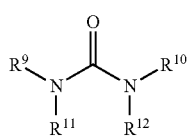

(23)

In the formula, $R^9$, $R^{10}$, $R^{11}$ and $R^{12}$ each independently represents an aliphatic group having 1 to 20 carbon atoms, an aliphatic group substituted with an aromatic compound having 7 to 20 carbon atoms, an aromatic group having 6 to 20 carbon atoms, or a hydrogen atom. The sum of the carbon numbers constituting $R^9$ and $R^{11}$ is an integer of 0 to 20, and the sum of the carbon numbers constituting $R^{10}$ and $R^{12}$ is an integer of 0 to 20.

Examples of $R^9$, $R^{10}$, $R^{11}$ and $R^{12}$ include a hydrogen atom; chain alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, and a nonadecyl group; aromatic groups having 6 to 20 carbon atoms such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, and a tributylphenyl group; and aralkyl groups having 7 to 20 carbon atoms such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specifically, examples of the urea compound represented by formula (23) include urea, methylurea, ethylurea, propylurea, butylurea, pentylurea, hexylurea, heptylurea, octylurea, nonylurea, decylurea, undecylurea, dodecylurea, tridecylurea, tetradecylurea, pentadecylurea, hexadecylurea, heptadecylurea, octadecylurea, nonadecylurea, phenylurea, N-(methylphenyl)urea, N-(ethylphenyl)urea, N-(propylphenyl)urea, N-(butylphenyl)urea, N-(pentylphenyl)urea, N-(hexylphenyl)urea, N-(heptylphenyl)urea, N-(octylphenyl)urea, N-(nonylphenyl)urea, N-(decylphenyl)urea, N-biphenylurea, N-(dimethylphenyl)urea, N-(diethylphenyl)urea, N-(dipropylphenyl)urea, N-(dibutylphenyl)urea, N-(dipentylphenyl)urea, N-(dihexylphenyl)urea, N-(diheptylphenyl)urea, N-terphenylurea, N-(trimethylphenyl)urea, N-(triethylphenyl)urea, N-(tripropylphenyl)urea, N-(tributylphenyl)urea, N-(phenylmethyl)urea, N-(phenylethyl)urea, N-(phenylpropyl)urea, N-(phenylbutyl)urea, N-(phenylpentyl)urea, N-(phenylhexyl)urea, N-(phenylheptyl)urea, N-(phenyloctyl)urea, N-(phenylnonyl)urea, dimethylurea, diethylurea, dipropylurea, dibutylurea, dipentylurea, dihexylurea, diheptylurea, dioctylurea, dinonylurea, didecylurea, diundecylurea, didodecylurea, ditridecylurea, ditetradecylurea, dipentadecylurea, dihexadecylurea, diheptadecylurea, dioctadecylurea, dinonadecylurea, diphenylurea, di(methylphenyl)urea, di(ethylphenyl)urea, di(propylphenyl)urea, di(butylphenyl)urea, di(pentylphenyl)urea, di(hexylphenyl)urea, di(heptylphenyl)urea, di(octylphenyl)urea, di(nonylphenyl)urea, di(decylphenyl)urea, di(biphenyl)urea, di(dimethylphenyl)urea, di(diethylphenyl)urea, di(dipropylphenyl)urea, di(dibutylphenyl)urea, di(dipentylphenyl)urea, di(dihexylphenyl)urea, di(diheptylphenyl)urea, di(terphenyl)urea, di(trimethylphenyl)urea, di(triethylphenyl)urea, di(tripropylphenyl)urea, di(tributylphenyl)urea, di(phenylmethyl)urea, di(phenylethyl)urea, di(phenylpropyl)urea, di(phenylbutyl)urea, di(phenylpentyl)urea, di(phenylhexyl)urea, di(phenylheptyl)urea, di(phenyloctyl)urea, and di(phenylnonyl)urea. Among them, urea in which $R^9$, $R^{10}$, $R^{11}$ and $R^{12}$ are hydrogen atoms in formula (23) is preferable.

As the N-unsubstituted carbamic acid ester, a compound represented by formula (24) is preferably used.

[Chemical Formula 14]

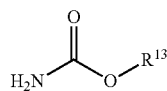

(24)

In the formula, $R^{13}$ represents an aliphatic group having 1 to 50 carbon atoms, an aralkyl group having 7 to 50 carbon atoms, or an aromatic group having 6 to 50 carbon atoms.

Examples of the aliphatic group of $R^{13}$ include a group composed of a specific non-metal atom (a carbon, oxygen, nitrogen, sulfur, silicon or halogen atom). Preferred examples of the aliphatic group include a chain hydrocarbon group, a cyclic hydrocarbon group, and a group composed of a chain hydrocarbon group and a cyclic hydrocarbon group. Examples of the aralkyl group include a group obtained by substituting a chain or branched-chain alkyl group having 1 to 44 carbon atoms with an aromatic group having 6 to 49 carbon atoms. In this case, a preferred aromatic group is a group composed of a specific non-metal atom (a carbon, oxygen, nitrogen, sulfur, silicon or halogen atom), examples thereof include a monocyclic aromatic group, a condensed polycyclic aromatic group, a cross-linked cyclic aromatic group, a ring assembly aromatic group, and a hetero cyclic aromatic group, and a substituted or unsubstituted phenyl group, a substituted or unsubstituted naphthyl group, and a substituted or unsubstituted anthryl group are more preferable.

Examples of the aromatic group of $R^{13}$ include a group composed of a specific non-metal atom (a carbon, oxygen, nitrogen, sulfur, silicon or halogen atom), examples thereof include a monocyclic aromatic group, a condensed polycyclic aromatic group, a cross-linked cyclic aromatic group, a ring assembly aromatic group, and a hetero cyclic aromatic group, and a substituted or unsubstituted phenyl group, a substituted or unsubstituted naphthyl group, and a substituted or unsubstituted anthryl group are preferable. Examples of the substituent group include a hydrogen atom and an aliphatic group (a chain hydrocarbon group, a cyclic hydrocarbon group, and a group composed of a chain hydrocarbon group and a cyclic hydrocarbon group), and may be a group composed of an aliphatic group and an aromatic group.

Specifically, examples of $R^{13}$ include chain alkyl groups having 1 to 50 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, nonadecyl group, and an eicosyl group; aromatic groups having 6 to 50 carbon atoms such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, and a tributylphenyl group; and aralkyl groups having 7 to 50 carbon atoms such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specifically, examples of the N-unsubstituted carbamic acid ester include methyl carbamate, ethyl carbamate, propyl carbamate, butyl carbamate, pentyl carbamate, hexyl carbamate, heptyl carbamate, octyl carbamate, nonyl carbamate, decyl carbamate, undecyl carbamate, dodecyl carbamate, tridecyl carbamate, tetradecyl carbamate, pentadecyl carbamate, hexadecyl carbamate, heptadecyl carbamate, octadecyl carbamate, nonadecyl carbamate, phenyl carbamate, (methylphenyl)carbamate, (ethylphenyl)carbamate, (propylphenyl)carbamate, (butylphenyl)carbamate, (pentylphenyl)carbamate, (hexylphenyl)carbamate, (heptylphenyl)carbamate, (octylphenyl)carbamate, (nonylphenyl)carbamate, (decylphenyl)carbamate, (biphenyl)carbamate, (dimethylphenyl)carbamate, (diethylphenyl)carbamate, (dipropylphenyl)carbamate, (dibutylphenyl)carbamate, (dipentylphenyl)carbamate, (dihexylphenyl)carbamate, (diheptylphenyl)carbamate, (terphenyl)carbamate, (trimethylphenyl)carbamate, (triethylphenyl)carbamate, (tripropylphenyl)carbamate, (tributylphenyl)carbamate, (phenylmethyl)

carbamate, (phenylethyl)carbamate, (phenylpropyl)carbamate, (phenylbutyl)carbamate, (phenylpentyl)carbamate, (phenylhexyl)carbamate, (phenylheptyl)carbamate, (phenyloctyl)carbamate, (phenylnonyl)carbamate, and structural isomers thereof.

<Carbonic Acid Ester>

A carbonic acid ester means a compound in which one or two hydrogen atoms in carbonic acid CO(OH)$_2$ are substituted with aliphatic groups or aromatic groups. In the present embodiment, a compound represented by formula (25) is preferably used.

[Chemical Formula 15]

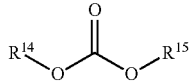
(25)

In the formula, $R^{14}$ and $R^{15}$ each independently represents an aliphatic group having 1 to 20 carbon atoms, an aralkyl group having 7 to 50 carbon atoms, or an aromatic group having 6 to 50 carbon atoms.

Examples of the aliphatic group of $R^{14}$ and $R^{15}$ include a group composed of a specific non-metal atom (a carbon, oxygen, nitrogen, sulfur, silicon or halogen atom). Preferred examples of the aliphatic group include a chain hydrocarbon group, a cyclic hydrocarbon group, and a group composed of a chain hydrocarbon group and a cyclic hydrocarbon group. Examples of the aralkyl group include a group obtained by substituting a chain alkyl group having 1 to 44 carbon atoms with an aromatic group having 6 to 49 carbon atoms. The aromatic group is preferably a group composed of a specific non-metal atom (a carbon, oxygen, nitrogen, sulfur, silicon or halogen atom), examples thereof include a monocyclic aromatic group, a condensed polycyclic aromatic group, a cross-linked cyclic aromatic group, a ring assembly aromatic group, and a hetero cyclic aromatic group, and a substituted or unsubstituted phenyl group, a substituted or unsubstituted naphthyl group, and a substituted or unsubstituted anthryl group are more preferable.

Examples of the aromatic group of $R^{14}$ and $R^{15}$ include a group composed of a specific non-metal atom (a carbon, oxygen, nitrogen, sulfur, silicon, or halogen atom), examples thereof include a monocyclic aromatic group, a condensed polycyclic aromatic group, a cross-linked cyclic aromatic group, a ring assembly aromatic group, and a hetero cyclic aromatic group, and a substituted or unsubstituted phenyl group, a substituted or unsubstituted naphthyl group, and a substituted or unsubstituted anthryl group are further preferable. Examples of the substituent group include a hydrogen atom and an aliphatic group (a chain hydrocarbon group, a cyclic hydrocarbon group, and a group composed of a chain hydrocarbon group and a cyclic hydrocarbon group), and may be a group composed of an aliphatic group and an aromatic group.

Examples of the $R^{14}$ and $R^{15}$ include chain alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group; aromatic groups which may be substituted, such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, and a tributylphenyl group; and aralkyl groups such as a phenylmethyl group, a phenylethyl group, a phenylpropyl group, a phenylbutyl group, a phenylpentyl group, a phenylhexyl group, a phenylheptyl group, a phenyloctyl group and a phenylnonyl group.

Specifically, examples of the carbonic acid ester include dimethyl carbonate, diethyl carbonate, dipropyl carbonate, dibutyl carbonate, dipentyl carbonate, dihexyl carbonate, diheptyl carbonate, dioctyl carbonate, dinonyl carbonate, didecyl carbonate, diundecyl carbonate, didodecyl carbonate, ditridecyl carbonate, ditetradecyl carbonate, dipentadecyl carbonate, dihexadecyl carbonate, diheptadecyl carbonate, dioctadecyl carbonate, dinonadecyl carbonate, diphenyl carbonate, di(methylphenyl)carbonate, di(ethylphenyl)carbonate, di(propylphenyl)carbonate, di(butylphenyl)carbonate, di(pentylphenyl)carbonate, di(hexylphenyl)carbonate, di(heptylphenyl)carbonate, di(octylphenyl)carbonate, di(nonylphenyl)carbonate, di(decylphenyl)carbonate, di(biphenyl)carbonate, di(dimethylphenyl)carbonate, di(diethylphenyl)carbonate, di(dipropylphenyl)carbonate, di(dibutylphenyl)carbonate, di(dipentylphenyl)carbonate, di(dihexylphenyl)carbonate, di(diheptylphenyl)carbonate, di(phenylphenyl)carbonate, di(trimethylphenyl)carbonate, di(triethylphenyl)carbonate, di(tripropylphenyl)carbonate, di(tributylphenyl)carbonate, di(phenylmethyl)carbonate, di(phenylethyl)carbonate, di(phenylpropyl)carbonate, di(phenylbutyl)carbonate, di(phenylpentyl)carbonate, di(phenylhexyl)carbonate, di(phenylheptyl)carbonate, di(phenyloctyl)carbonate, di(phenylnonyl)carbonate, and structural isomers thereof.

Among these compounds, in view of distillation purification of the isocyanate described below and thermal stability of compounds in manufacturing an isocyanate polymer using the above-described isocyanate, as the carbonic acid derivative, the carbonic acid ester or the N-unsubstituted carbamic acid ester is preferable, and the carbonic acid ester is further preferable.

<Compound Represented by Formula (1)>

Examples of the unsaturated bond compound according to the present embodiment include a compound represented by formula (1).

[Chemical Formula 16]

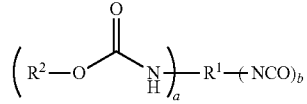
(1)

In the formula, $R^1$ is synonymous with $R^1$ defined in formula (10), $R^2$ represents a monovalent organic group, a represents an integer of 1 to 5, b represents an integer of 0 to 4, the sum of a and b is c, and c is an integer of 2 to 5.

As described below, $R^2$ is derived from a hydroxy compound and can be represented as a residue obtained by removing a hydroxy group (—OH) constituting a hydroxy compound, and thus, hereinafter, for ease of explanation of $R^2$, $R^2$ is defined as a hydroxy compound ($R^2OH$) obtained by adding a hydroxy group to $R^2$.

The hydroxy compound ($R^2OH$) may be an alcohol or an aromatic hydroxy compound.

When the hydroxy compound ($R^2OH$) is an alcohol, a compound represented by $R^2(OH)_e$ can be used. $R^2$ represents an aliphatic group having 1 to 50 carbon atoms, or a group composed of an aliphatic group to which an aromatic group having 7 to 50 carbon atoms is bonded, which is substituted with e hydroxy groups, and e represents an integer of 1 to 3. In addition, $R^2$ is a group not having active hydrogen other than the hydroxy group.

Examples of the aliphatic hydrocarbon group of $R^2$ include an aliphatic hydrocarbon group in which atoms other than hydrogen atoms constituting the above-described group are specific non-metal atoms (a carbon, oxygen, nitrogen, sulfur, silicon, or halogen atom). Preferred examples of the aliphatic group include a chain hydrocarbon group, a cyclic hydrocarbon group, and a group to which at least one group selected from the above-described chain hydrocarbon groups and the above-described cyclic hydrocarbon group is bonded (indicating cyclic hydrocarbon group substituted with chain hydrocarbon group, chain hydrocarbon group substituted with cyclic hydrocarbon group, and the like, for example). Moreover, examples of the aliphatic group substituted with an aromatic group include a chain alkyl group substituted with an aromatic group, a cycloalkyl group substituted with an aromatic group, or an alkyl group having 1 to 44 carbon atoms substituted with the above-described aromatic group having 6 to 49 carbon atoms. As described above, the above-described aromatic group is preferably an aromatic group in which atoms other than hydrogen atoms constituting the above-described aromatic group are specific non-metal atoms (a carbon, oxygen, nitrogen, sulfur, silicon, or halogen atom), examples thereof include a monocyclic aromatic group, a condensed polycyclic aromatic group, a cross-linked cyclic aromatic group, a ring assembly aromatic group, and a hetero cyclic aromatic group, and a substituted or unsubstituted phenyl group, a substituted or unsubstituted naphthyl group, and a substituted or unsubstituted anthryl group are further preferable.

Examples of the $R^2$ include chain alkyl groups such as a methyl group, an ethyl group, a propyl group, a butyl group, a pentyl group, a hexyl group, a heptyl group, an octyl group, a nonyl group, a decyl group, a dodecyl group, an octadecyl group, and structural isomers thereof; cycloalkyl groups such as a cyclopentyl group, a cyclohexyl group, a cycloheptyl group, a cyclooctyl group, and structural isomers thereof; groups composed of a chain alkyl group and a cycloalkyl group, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; and aralkyl groups such as a phenylmethyl group, a phenylethyl group, a phenylpropyl group, a phenylbutyl group, a phenylpentyl group, a phenylhexyl group, a phenylheptyl group, a phenyloctyl group, a phenylnonyl group, and structural isomers thereof.

Among these alcohols, considering industrial use, an alcohol having one or two alcoholic hydroxy groups (a hydroxy group constituting the above-described hydroxy compound and being directly added to a carbon atom other than an aromatic ring) is preferable because of generally low viscosity, and a monoalcohol having the above-described one alcoholic hydroxy group is more preferable.

Specifically, examples of the alcohol include unsubstituted alkyl alcohols such as methyl alcohol, ethyl alcohol, propyl alcohol, butyl alcohol, pentyl alcohol, hexyl alcohol, heptyl alcohol, octyl alcohol, nonyl alcohol, decyl alcohol, dodecyl alcohol, octadecyl alcohol, and structural isomers thereof; unsubstituted cycloalkyl alcohols such as cyclopentyl alcohol, cyclohexyl alcohol, cycloheptyl alcohol, cyclooctyl alcohol, and structural isomers thereof; alcohols composed of a chain alkyl group and a cycloalkyl alcohol, such as methylcyclopentyl alcohol, ethylcyclopentyl alcohol, methylcyclohexyl alcohol, ethylcyclohexyl alcohol, propylcyclohexyl alcohol, butylcyclohexyl alcohol, pentylcyclohexyl alcohol, hexylcyclohexyl alcohol, dimethylcyclohexyl alcohol, diethylcyclohexyl alcohol, dibutylcyclohexyl alcohol, and structural isomers thereof; and alkyl alcohols substituted with an aromatic group, such as phenylmethyl alcohol, phenylethyl alcohol, phenylpropyl alcohol, phenylbutyl alcohol, phenylpentyl alcohol, phenylhexyl alcohol, phenylheptyl alcohol, phenyloctyl alcohol, phenylnonyl alcohol, and structural isomers thereof.

Among them, from the viewpoint of easy availability, and solubility and the like of raw materials and products, alkyl alcohols having 1 to 20 carbon atoms are preferably used.

When the above-described hydroxy compound ($R^2OH$) is an aromatic hydroxy compound, because of industrial usability and low viscosity in general, a mono- to trivalent (that is, the number of hydroxy groups bonded to aromatic ring is integer of 1 to 3) aromatic hydroxy compound is preferable. Examples of the aromatic hydroxy compound include a compound represented by formula (26).

[Chemical Formula 17]

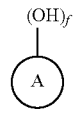

(26)

In the formula, the ring A represents an aromatic hydrocarbon ring which may have a substituent group, the ring A may be monocyclic or polycyclic, and f represents an integer of 1 to 3.

Among the aromatic hydroxy compounds represented by formula (26), a monovalent aromatic hydroxy compound in which f is 1 is more preferable.

The substituent group which substitutes the above-described aromatic hydrocarbon ring is selected from a halogen atom, an aliphatic group, and an aromatic group, and examples thereof include cyclic groups such as cyclic hydrocarbon groups (a monocyclic hydrocarbon group, a condensed polycyclic hydrocarbon group, a cross-linked cyclic hydrocarbon group, a spiro hydrocarbon group, a ring assembly hydrocarbon group, and a cyclic hydrocarbon group having a side chain), hetero ring groups, hetero cyclic spiro groups, and hetero cross-linked ring groups, acyclic hydrocarbon groups, and groups bonded to one or more groups selected from acyclic hydrocarbon groups and cyclic groups.

Among these substituent groups, the substituent group that can be preferably used in the present embodiment is, considering difficulty in occurrence of side reactions, a group selected from the group consisting of acyclic hydrocarbon groups, and cyclic hydrocarbon groups (a monocyclic hydrocarbon group, a condensed polycyclic hydrocarbon group, a cross-linked cyclic hydrocarbon group, a Spiro hydrocarbon group, a ring assembly hydrocarbon group, and a cyclic hydrocarbon group having a side chain), and groups to which at least one group selected from the above-described groups is bonded (mutually-substituted group).

The substituent group that substitutes the ring A is a group selected from the group consisting of an alkyl group, a cycloalkyl group, an aryl group, an aralkyl group, and an ether group (substituted or unsubstituted alkyl ether, arylether, or aralkyl ether); a group to which one or more groups selected from the above-described groups are bonded; a group selected from a group composed of groups to which one or more groups selected from the above-described groups are bonded through a saturated hydrocarbon bond or an ether bond; or a halogen atom, in which the sum of the number of carbon atoms constituting the ring A and the number of carbon atoms constituting the all substituent groups that substitute the ring A is an integer of 6 to 50.

Examples of the ring A include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring, and a structure comprising at least one structure selected from a benzene ring and a naphthalene ring is preferable.

From the viewpoint of industrial use, an aromatic hydroxy compound having an easily-available benzene ring as a skeleton is preferable. Examples of the aromatic hydroxy compound include an aromatic hydroxy compound represented by formula (27).

[Chemical Formula 18]

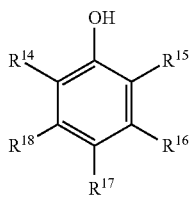

(27)

In the formula, $R^{14}$, $R^{15}$, $R^{16}$, $R^{17}$ and $R^{18}$ each independently represents a group selected from the group consisting of a chain alkyl group, a cycloalkyl group, an aryl group, an aralkyl group, and an ether group (substituted or unsubstituted alkyl ether, arylether, or aralkyl ether); a group to which one or more groups selected from the above-described groups are bonded; a group selected from groups composed of a group to which one or more groups selected from the above-described groups are bonded through a saturated aliphatic bond or an ether bond; a halogen atom; or a hydrogen atom, and the sum of the number of carbon atoms constituting $R^{14}$ to $R^{18}$ is an integer of 0 to 44.

In formula (27), preferred $R^{14}$ to $R^{18}$ are groups independently selected from groups shown in the following (i) to (v):
(i) a hydrogen atom,
(ii) a halogen atom,
(iii) a carbon functional group having the number of constituting carbon atoms of 1 to 44, and the carbon functional group is bonded to the carbon atom at the α-position with a group selected from, each independently, a group selected from a chain alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 carbon atoms and not having a hydroxy group at the terminal, an aryl group having 6 to 43 carbon atoms, an aralkyl group having 7 to 43 carbon atoms, and an aralkyloxy group having 7 to 43 carbon atoms,
(iv) an aromatic group having 1 to 44 carbon atoms, and the above-described aromatic group is bonded with a group selected from a hydrogen atom, a chain alkyl group having 1 to 38 carbon atoms, a cycloalkyl group having 4 to 38 carbon atoms, an alkoxy group having 1 to 38 carbon atoms, a polyoxyalkylene alkyl ether group having 2 to 38 carbon atoms and not having a hydroxy group at the terminal, an aromatic group having 6 to 38 carbon atoms, an aralkyl group having 7 to 38 carbon atoms, an aralkyloxy group having 7 to 38 carbon atoms, and a group to which one or more of the above-described groups,
(v) an oxygen functional group having 1 to 44 carbon atoms, and the above-described oxygen functional group is bonded with an alkyl group having 1 to 44 carbon atoms, a cycloalkyl group having 1 to 44 carbon atoms, an alkoxy group having 1 to 44 carbon atoms, a polyoxyalkylene alkyl ether group having 2 to 44 carbon atoms and not having a hydroxy group at the terminal, an aromatic group having 6 to 44 carbon atoms, an aralkyl group having 7 to 44 carbon atoms, an aralkyloxy group having 7 to 44 carbon atoms, or a group to which one or more of the above-described groups.

Here, the "aralkyloxy group" means a group in which an oxygen atom is bonded to the aralkyl group described above.

Examples of $R^{14}$ to $R^{18}$ include chain alkyl groups such as a methyl group, an ethyl group, a propyl group, a butyl group, a pentyl group, a hexyl group, a heptyl group, an octyl group, a nonyl group, a decyl group, a dodecyl group, an octadecyl group, and structural isomers thereof; cycloalkyl groups such as a cyclopentyl group, a cyclohexyl group, a cycloheptyl group, and a cyclooctyl group; groups composed of a chain alkyl group and a cycloalkyl group, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; chain alkyloxy groups such as a methoxy group, an ethoxy group, a propoxy group, a butyloxy group, a pentyloxy group, a hexyloxy group, a heptyloxy group, an octyloxy group, a nonyloxy group, a decyloxy group, a dodecyloxy group, an octadecyloxy group, and structural isomers thereof; cycloalkyloxy groups such as a cyclopentyloxy group, a cyclohexyloxy group, a cycloheptyloxy group, and a cyclooctyloxy group; alkyloxy groups corresponding to groups composed of a chain alkyl group and a cycloalkyl group, such as a methylcyclopentyloxy group, an ethylcyclopentyloxy group, a methylcyclohexyloxy group, an ethylcyclohexyloxy group, a propylcyclohexyloxy group, a butylcyclohexyloxy group, a pentylcyclohexyloxy group, a hexylcyclohexyloxy group, a dimethylcyclohexyloxy group, a diethylcyclohexyloxy group, a dibutylcyclohexyloxy group, and structural isomers thereof; aromatic groups such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, a tributylphenyl group, and structural isomers thereof; groups composed of an aromatic group and an alkyl group, such as a 1-methyl-1-phenylethyl group, and a 1-phenylethyl group; aromatic oxy groups such as a phenoxy group, a methylphenoxy group, an ethylphenoxy group, a propylphenoxy group, a butylphenoxy group, a pentylphenoxy group, a hexylphenoxy group, a heptylphenoxy group, an octylphenoxy group, a nonylphenoxy group, a decylphenoxy group, a phenylphenoxy group, a dimethylphenoxy group, a diethylphenoxy group, a dipropylphenoxy group, a dibutylphenoxy group, a dipentylphenoxy group, a dihexylphenoxy group, a diheptylphenoxy group, a diphenylphenoxy group, a trimethylphenoxy group, a triethylphenoxy group, a tripropylphenoxy group, a tributylphenoxy group, and structural isomers thereof; aralkyl groups such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group; and aralkyloxy groups such as a phenylmethoxy group, a phenylethoxy group, a phenylpropyloxy group, a phenylbutyloxy group, a phenylpentyloxy group, a phenylhexyloxy group, a phenylheptyloxy group, a phenyloctyloxy group, a phenylnonyloxy group, and structural isomers thereof.

For example, in formula (1), when $R^2O$ is a group obtained by removing a hydrogen atom from a hydroxy group of the aromatic hydroxy compound represented by formula (26) and a is 1 or 2, the compound represented by formula (1) is a compound represented by formula (1-1) and a compound represented by formula (1-2). The compound represented by formula (1) may be one manufactured by the combination of a diisocyanate and a hydroxy compound.

[Chemical Formula 19]

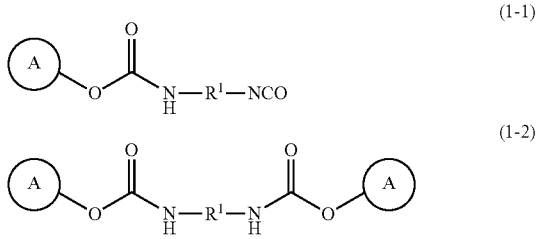

In the formula, the ring A represents a group synonymous with the ring A defined in formula (26), and $R^1$ represents a group synonymous with $R^1$ defined in formula (1).

<Compound Having Unsaturated Bond Between Carbon and Carbon>

Examples of the compound having an unsaturated bond between carbon and carbon in the present embodiment include a compound represented by formula (21).

[Chemical Formula 20]

In the formula, $R^5$, $R^6$, $R^7$, and $R^8$ each independently represents a hydrogen atom, a halogen atom, or an organic group having 1 to 10 carbon atoms, $R^5$ to $R^8$ are not simultaneously hydrogen atoms, and d represents an integer of 1 to 3.

$R^6$ to $R^8$ are preferably hydrogen atoms or organic groups having 1 to 10 carbon atoms. When $R^6$ to $R^8$ are organic groups, they are preferably aliphatic groups having 1 to 10 carbon atoms or aromatic groups having 6 to 10 carbon atoms. Examples of the $R^6$ to $R^8$ include alkyl groups such as a methyl group, an ethyl group, a propyl group, a butyl group, a pentyl group, a hexyl group, a heptyl group, an octyl group, a nonyl group, a decyl group, and structural isomers thereof; chain alkyloxy groups such as a methyloxy group, an ethyloxy group, a propyloxy group, a butyloxy group, a pentyloxy group, a hexyloxy group, a heptyloxy group, an octyloxy group, a nonyloxy group, a decyloxy group, and structural isomers thereof; cycloalkyl groups such as a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; groups composed of a chain alkyl group and a cycloalkyl group; and groups formed by removing one hydrogen atom from aromatic compounds such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof.

$R^5$ is preferably a hydrogen atom or an organic group having 1 to 10 carbon atoms. When $R^5$ is an organic group, it is preferably an aliphatic group having 1 to 10 carbon atoms or an aromatic group having a 6 to 10 carbon atoms. Examples of the $R^5$ include groups formed by removing d hydrogen atoms from alkanes such as methane, ethane, propane, butane, pentane, hexane, heptane, octane, nonane, decane, and structural isomers thereof; groups formed by removing d hydrogen atoms from alkanes such as cyclopentane, cyclohexane, cycloheptane, and cyclooctane; groups formed by removing d hydrogen atoms from cycloalkanes substituted with a chain alkyl group, such as methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof; and groups formed by removing d hydrogen atoms from aromatic compounds such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof.

Examples of the compound represented by formula (21) include propene, butene, pentene, 2-methylbutene, 2,4,4-trimethylpentene-1, hexene, octene, nonene, decene, hexadecene, octadecene, butadiene, pentadiene, hexadiene, chloroethylene, chloropropene, chlorobutene, chloropentene, chlorohexene, chlorooctene, chlorononene, chlorodecene, chlorohexadecene, chlorooctadecene, chlorobutadiene, chloropentadiene, chlorohexadiene, dichloroethylene, dichloropropene, dichlorobutene, dichloropentene, dichlorohexene, dichlorooctene, dichlorononene, dichlorodecene, dichlorohexadecene, dichlorooctadecene, dichlorobutadiene, dichloropentadiene, dichlorohexadiene, bromo ethylene, bromopropene, bromobutene, bromopentene, bromohexene, bromooctene, bromononene, bromodecene, bromohexadecene, bromooctadecene, bromobutadiene, bromopentadiene, bromohexadiene, dibromoethylene, dibromopropene, dibromobutene, dibromopentene, dibromohexene, dibromooctene, dibromononene, dibromodecene, dibromohexadecene, dibromooctadecene, dibromobutadiene, dibromopentadiene, dibromohexadiene, fluoroethylene, fluoropropene, fluorobutene, fluoropentene, fluorohexene, fluorooctene, fluorononene, fluorodecene, fluorohexadecene, fluorooctadecene, fluorobutadiene, fluoropentadiene, fluorohexadiene, difluoroethylene, difluoropropene, difluorobutene, difluoropentene, difluorohexene, difluorooctene, difluorononene, difluorodecene, difluorohexadecene, difluorooctadecene, difluorobutadiene, difluoropentadiene, difluorohexadiene, styrene, propenylbenzene, isopropylbenzene (also referred to as "α-methylstyrene"), allylbenzene, phenylbutadiene, divinylbenzene, stilbene, vinylanisole, propenylanisole, anilanisole, isoanethole, elemicin, asarone, chlorostyrene, chloropropenylbenzene, chloroisopropenylbenzene, chloroallylbenzene, chlorophenylbutadiene, chlorodivinylbenzene, chlorostilbene, chlorovinylanisole, chloropropenylanisole, chloroanilanisole, chloroisoanethole, chloroelemicin, chloroasarone, bromostyrene, bromopropenylbenzene, bromoisopropenylbenzene, bromoallylbenzene, bromophenylbutadiene, bromodivinylbenzene, bromostilbene, bromovinylanisole, bromopropenylanisole, bromoanilanisole, bromoisoanethole, bromoelemicin, bromoasarone, fluorostyrene, fluoropropenylbenzene, fluoroisopropenylbenzene, fluoroallylbenzene, fluorophenylbutadiene, fluorodivinylbenzene, fluorostilbene, fluorovinylanisole, fluoropropenylanisole, fluoroanilanisole, fluoroisoanethole, fluoroelemicin, fluoroasarone, dichlorostyrene, dichloropropenylbenzene, dichloroisopropenylbenzene, dichloroallylbenzene, dichlorophenylbutadiene, dichlorodivinylbenzene, dichlorostilbene, dichlorovinylanisole, dichloropropenylanisole, dichloroanilanisole, dichloroisoanethole, dichloroelemicin, dichloroasarone, dibromostyrene, dibromopropenylbenzene, dibromoisopropenylbenzene, dibromoallylbenzene, dibromophenylbutadiene, dibromodivinylbenzene, dibromostilbene, dibromovinylanisole, dibromopropenylanisole, dibromoanilanisole, dibromoisoanethole, dibromoelemicin, dibromoasarone, difluorostyrene, difluoropropenylbenzene, difluoroisopropenylbenzene, difluoroallylbenzene, difluorophenylbutadiene, difluorodivinylbenzene, difluorostilbene, difluorovinylanisole, difluoropropenylanisole, difluoroanilanisole, difluoroisoanethole, difluoroelemicin, difluoroasarone, and structural isomers thereof. Among them, from the viewpoint of thermal stability, a compound not including a halogen atom is preferably used.

As the compound having at least one unsaturated bond, among the carbonic acid derivative, the compound represented by formula (1), and the compound represented by formula (21), considering stability to heat, handling of the composition of the present embodiment, and stability to oxygen, water and the like that are incorporated during storage, the compound represented by formula (1) or the compound represented by formula (21) are preferable.

<Inactive Compound>

The composition of the present embodiment may comprise at least one compound selected from the group consisting of a hydrocarbon compound, an ether compound, a sulfide compound, a halogenated hydrocarbon compound, a Si-containing hydrocarbon compound, a Si-containing ether compound, and a Si-containing sulfide compound (hereinafter, also referred to as "inactive compound"). The inactive compound is classified into the following compound A to compound G.

The hydrocarbon compound is classified into compound A and compound B, the ether compound and the sulfide compound are classified into the following compounds C to E, the halogenated hydrocarbon compound is classified into the following compound F, and the Si-containing hydrocarbon compound, the Si-containing ether compound, and the Si-containing sulfide compound are classified into the following compound G, respectively.

Compound A: Aliphatic hydrocarbon compounds having a linear-chain, branched-chain, or cyclic structure.

Compound B: Aromatic hydrocarbon compounds which may be substituted with an aliphatic hydrocarbon group.

Compound C: Compounds having an ether bond or a sulfide bond, and an aliphatic hydrocarbon group, to which the same or a different aliphatic hydrocarbon compound is bonded through the ether bond or the sulfide bond.

Compound D: Compounds having an ether bond or a sulfide bond, and an aromatic hydrocarbon group, to which the same or a different aromatic hydrocarbon compound is bonded through the ether bond or the sulfide bond.

Compound E: Compounds having an ether bond or a sulfide bond, an aliphatic hydrocarbon group, and an aromatic hydrocarbon group.

Compound F: Halides in which at least one hydrogen atom constituting an aliphatic hydrocarbon compound or at least one hydrogen atom constituting an aromatic hydrocarbon compound is substituted with a halogen atom.

Compound G: Compounds in which a part or all of carbon atoms of the above-described compound A to compound E is substituted with silicon atoms.

The compound A is preferably a hydrocarbon compound having 5 to 20 carbon atoms. Specific examples of the compound A include pentane, hexane, heptane, octane, nonane, decane, dodecane, tetradecane, pentadecane, hexadecane, octadecane, nonadecane, cyclopentane, cyclohexane, cycloheptane, cyclooctane, methylcyclopentane, ethylcyclopentane, methyl cyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof.

The compound B is preferably a hydrocarbon compound having 5 to 20 carbon atoms. Specific examples of the compound B include benzene, toluene, ethylbenzene, butylbenzene, pentylbenzene, hexylbenzene, octylbenzene, biphenyl, terphenyl, diphenylethane, (methylphenyl)phenylethane, dimethylbiphenyl, benzyltoluene, naphthalene, methylnaphthalene, ethylnaphthalene, butylnaphthalene, and structural isomers thereof.

The compound C is preferably a compound having 2 to 20 carbon atoms. Specific examples of the compound C include ethers to which a hydrocarbon compound is bonded through an ether bond, such as ethyl ether, butyl ether, octyl ether, nonyl ether, decyl ether, methyl ethyl ether, methyl butyl ether, methyl octyl ether, methyl nonyl ether, methyl decyl ether, ethyl butyl ether, ethyl octyl ether, ethyl nonyl ether, ethyl decyl ether, butyl octyl ether, butyl nonyl ether, butyl decyl ether, octyl nonyl ether, octyl decyl ether, dicyclopentyl ether, dicyclohexyl ether, dicyclooctyl ether, cyclohexyl ethyl ether, cyclohexyl butyl ether, cyclohexyl octyl ether, cyclohexyl nonyl ether, cyclohexyl decyl ether, tetraethylene glycol dimethyl ether, and structural isomers thereof; and sulfides to which a hydrocarbon compound is bonded through a sulfide bond, such as ethyl sulfide, butyl sulfide, octyl sulfide, nonyl sulfide, decyl sulfide, methyl ethyl sulfide, methyl butyl sulfide, methyl octyl sulfide, methyl nonyl sulfide, methyl decyl sulfide, ethyl butyl sulfide, ethyl octyl sulfide, ethyl nonyl sulfide, ethyl decyl sulfide, butyl octyl sulfide, butyl nonyl sulfide, butyl decyl sulfide, octyl nonyl sulfide, octyl decyl sulfide, dicyclopentyl sulfide, dicyclohexyl sulfide, dicyclooctyl sulfide, cyclohexyl ethyl sulfide, cyclohexyl butyl sulfide, cyclohexyl octyl sulfide, cyclohexyl nonyl sulfide, cyclohexyl decyl sulfide, and structural isomers thereof.

The compound D is preferably a compound having 2 to 20 carbon atoms. Specific examples of the compound D include aromatic ethers to which an aromatic hydrocarbon compound is bonded through an ether bond, such as diphenyl ether, (methylphenyl)-phenyl ether, (ethylphenyl)phenyl ether, (butylphenyl)phenyl ether, (hexylphenyl)phenyl ether, (methylphenyl)ether, (ethylphenyl)ether, (butylphenyl) ether, (hexylphenyl)ether, dibenzyl ether, di(methylbenzyl) ether, di(ethylbenzyl)ether, di(butylbenzyl)ether, di(pentylbenzyl)ether, di(hexylbenzyl)ether, di(octylbenzyl)ether, diphenyl ether, and structural isomers thereof; and aromatic sulfides to which an aromatic hydrocarbon compound is bonded through a sulfide bond, such as diphenyl sulfide, (methylphenyl)phenyl sulfide, (ethylphenyl)phenyl sulfide, (butylphenyl)phenyl sulfide, (hexylphenyl)phenyl sulfide, (methylphenyl)sulfide, (ethylphenyl)sulfide, (butylphenyl) sulfide, (hexylphenyl)sulfide, di(methylbenzyl)sulfide, di(ethylbenzyl)sulfide, di(butylbenzyl)sulfide, di(pentylbenzyl)sulfide, di(hexylbenzyl)sulfide, di(octylbenzyl)sulfide, diphenyl sulfide, dibenzyl sulfide, and structural isomers thereof.

The compound E is preferably a compound having 7 to 20 carbon atoms. Specific examples of the compound E include phenyl methyl ether, phenyl ethyl ether, phenyl butyl ether, phenyl octyl ether, phenyl nonyl ether, phenyl decyl ether, benzyl ethyl ether, benzyl butyl ether, benzyl octyl ether, benzyl nonyl ether, benzyl decyl ether, (methylphenyl) ethyl ether, (methylphenyl) butyl ether, (methylphenyl)octyl ether, (methylphenyl)nonyl ether, (methylphenyl)decyl ether, (ethylphenyl) ethyl ether, (ethylphenyl) butyl ether, (ethylphenyl)octyl ether, (ethylphenyl)nonyl ether, (ethylphenyl)decyl ether, (butylphenyl) ethyl ether, (butylphenyl) butyl ether, (butylphenyl)octyl ether, (butylphenyl)nonyl ether, (butylphenyl)decyl ether, and structural isomers thereof.

The compound F is preferably a compound having 2 to 20 carbon atoms. Specifically, examples thereof include chloroethane, chloropropane, chlorobutane, chloropentane, chlorohexane, chloroheptane, chlorooctane, chlorononane, chlorodecane, chlorododecane, chlorotetradecane, chloropentadecane, chlorohexadecane, chlorooctadecane, chlorononadecane, chlorocyclopentane, chlorocyclohexane, chlorocycloheptane, chlorocyclooctane, chloromethylcyclopentane, chloroethylcyclopentane, chloromethylcyclohexane, chloroethylcyclohexane, chloropropylcyclohexane, chlorobutylcyclohexane, chloropentylcyclohexane, chlorohexylcyclohexane, chlorodimethylcyclohexane, chlorodiethylcyclohexane, chlorodibutylcyclohexane, chlorobenzene, chloromethylbenzene, chloroethylbenzene, chlorobutylbenzene, chloropentylbenzene, chlorohexylbenzene, chlorooctylbenzene, chlorobiphenyl, chloroterphenyl, chlorodiphenylethane, chloro(methylphenyl)phenylethane, chlorodimethylbiphenyl, chlorobenzyltoluene, chloronaphthalene, chloromethylnaphthalene, chloroethylnaphthalene, chlorobutylnaphthalene, dichloroethane, dichloropropane, dichlorobutane, dichloropentane, dichlorohexane, dichloroheptane, dichlorooctane, dichlorononane, dichlorodecane, dichlorododecane, dichlorotetradecane, dichloropentadecane, dichlorohexadecane, dichlorooctadecane, dichlorononadecane, dichlorocyclopentane, dichlorocyclohexane, dichlorocycloheptane, dichlorocyclooctane, dichloromethylcyclopentane, dichloroethylcyclopentane, dichloromethylcyclohexane, dichloroethylcyclohexane, dichloropropylcyclohexane, dichlorobutylcyclohexane, dichloropentylcyclohexane, dichlorohexylcyclohexane, dichlorodimethylcyclohexane, dichlorodiethylcyclohexane, dichlorodibutylcyclohexane, dichlorobenzene, dichloromethylbenzene, dichloroethylbenzene, dichlorobutylbenzene, dichloropentylbenzene, dichlorohexylbenzene, dichlorooctylbenzene, dichlorobiphenyl, dichloroterphenyl, dichlorodiphenylethane, dichloro(methylphenyl)phenylethane, dichlorodimethylbiphenyl, dichlorobenzyltoluene, dichloronaphthalene, dichloromethylnaphthalene, dichloroethylnaphthalene, dichlorobutylnaphthalene, dibromoethane, dibromopropane, dibromobutane, dibromopentane, dibromohexane, dibromoheptane, dibromooctane, dibromononane, dibromodecane, dibromododecane, dibromotetradecane, dibromopentadecane, dibromohexadecane, dibromooctadecane, dibromononadecane, dibromocyclopentane, dibromocyclohexane, dibromocycloheptane, dibromocyclooctane, dibromomethylcyclopentane, dibromoethylcyclopentane, dibromomethylcyclohexane, dibromoethylcyclohexane, dibromopropylcyclohexane, dibromobutylcyclohexane, dibromopentylcyclohexane, dibromohexylcyclohexane, dibromodimethylcyclohexane, dibromodiethylcyclohexane, dibromodibutylcyclohexane, dibromobenzene, dibromomethylbenzene, dibromoethylbenzene, dibromobutylbenzene, dibromopentylbenzene, dibromohexylbenzene, dibromooctylbenzene, dibromobiphenyl, dibromoterphenyl, dibromodiphenylethane, dibromo(methylphenyl)phenylethane, dibromodimethylbiphenyl, dibromobenzyltoluene, dibromonaphthalene, dibromomethylnaphthalene, dibromoethylnaphthalene, dibromobutylnaphthalene, difluoroethane, difluoropropane, difluorobutane, difluoropentane, difluorohexane, difluoroheptane, difluorooctane, difluorononane, difluorodecane, difluorododecane, difluorotetradecane, difluoropentadecane, difluorohexadecane, difluorooctadecane, difluorononadecane, difluorocyclopentane, difluorocyclohexane, difluorocycloheptane, difluorocyclooctane, difluoromethylcyclopentane, difluoroethylcyclopentane, difluoromethylcyclohexane, difluoroethylcyclohexane, difluoropropylcyclohexane, difluorobutylcyclohexane, difluoropentylcyclohexane, difluorohexylcyclohexane, difluorodimethylcyclohexane, difluorodiethylcyclohexane, difluorodibutylcyclohexane, difluorobenzene, difluoromethylbenzene, difluoroethylbenzene, difluorobutylbenzene, difluoropentylbenzene, difluorohexylbenzene, difluorooctylbenzene, difluorobiphenyl, difluoroterphenyl, difluorodiphenylethane, difluoro(methylphenyl)phenylethane, difluorodimethylbiphenyl, difluorobenzyltoluene, difluoronaphthalene, difluoromethylnaphthalene, difluoroethylnaphthalene, difluorobutylnaphthalene, and structural isomers thereof.

The compound G is a compound obtained by substituting a part or all of carbon atoms of the compound A to compound E with silicon atoms, and specifically, examples thereof include tetraethylsilane, tetrabutylsilane, tetrahexylsilane, tetracyclohexylsilane, tetraphenylsilane, dimethyldibutylsilane, dimethyldicyclohexylsilane, dimethyldiphenylsilane, hexamethylcyclotrisiloxane, hexaethylcyclotrisiloxane, hexacyclohexylcyclotrisiloxane, trimethyltricyclohexylcyclotrisiloxane, trimethyltriphenylcyclotrisiloxane, hexaphenylcyclotrisiloxane, octamethylcyclotetrasiloxane, octaethylcyclotetrasiloxane, octacyclohexylcyclotetrasiloxane, tetramethyltetracyclohexylcyclotetrasiloxane, tetramethyltetraphenylcyclotetrasiloxane, octaphenylcyclotetrasiloxane, octamethyltrisiloxane, decamethyltetrasiloxane, tetramethyltetraphenyltrisiloxane, pentamethylpentaphenyltetrasiloxane, and structural isomers thereof.

Among them, compounds containing a halogen atom, such as the compound F, may provoke unexpected side reactions associated with generation of a halogen radical depending on handling and storing conditions of the polyisocyanate composition of the present embodiment. In addition, compounds having an ether bond or a sulfide bond, such as the compound C, compound D, and compound E, may generate an oxide or a peroxide depending on conditions. From the viewpoint of being thermally-stable, the compound A, compound B, or compound G is preferable.

<Polyisocyanate Composition>

The polyisocyanate composition of the present embodiment is characterized by comprising a polyisocyanate, and a compound having at least one unsaturated bond that is a different compound from the polyisocyanate, or at least one inactive compound selected from the group consisting of a hydrocarbon compound, an ether compound, a sulfide compound, a halogenated hydrocarbon compound, a Si-containing hydrocarbon compound, a Si-containing ether compound, and a Si-containing sulfide compound.

The polyisocyanate composition has a plurality of preferred embodiments. Hereinafter, the preferred embodiments will be described with reference to three examples (I) to (III), but the present invention is not limited thereto.

(I) Polyisocyanate composition containing polyisocyanate and compound other than polyisocyanate, having at least one unsaturated bond (unsaturated bond compound).

The content of the polyisocyanate is, on the basis of the total mass of the polyisocyanate composition, 97 mass % or more, and the content of the unsaturated bond compound is 2.0 mass ppm or more and $1.0 \times 10^4$ mass ppm or less.

According to the present embodiment, a method for suppressing coloration in distillation purification of the polyisocyanate can be provided. In the method of the present embodiment, on the basis of the total mass of the polyisocyanate, 2.0 mass ppm or more and $1.0 \times 10^4$ mass ppm or less of the unsaturated bond compound is added to the polyisocyanate before distillation purification. When the distillation purification is performed using the above-described polyisocyanate composition, coloration is thus sufficiently suppressed.

In the polyisocyanate composition of the present embodiment, the content of the polyisocyanate is 97 mass % or more, and preferably 98 mass % or more. In addition, the content of the polyisocyanate may be 99.5 mass % or less, or 99 mass % or less.

The content of the unsaturated bond compound is, on the basis of the total mass of the polyisocyanate composition, 2.0 mass ppm or more and $1.0 \times 10^4$ mass ppm or less (0.0002 mass % or more and 1 mass % or less).

Generally, an unsaturated bond of an unsaturated bond compound tends to be oxidized, and an unsaturated bond compound as contaminant is easy to become the cause of coloration. However, in the present embodiment, the unsaturated bond compound effectively acts in the distillation purification of the polyisocyanate and exhibits an effect of suppressing the coloration of the polyisocyanate to be distillation-purified.

Although the mechanism for exhibiting the effect is not clear, it is considered that, when the unsaturated bond compound selectively interacts with a compound that becomes the cause of the coloration, such as oxygen, the coloration of the polyisocyanate is suppressed. On the other hand, it is considered that a colored substance derived from the unsaturated bond compound is produced by the reaction of the unsaturated bond compound and the compound of the cause of the coloration, such as oxygen, but the colored substance can be separated from the polyisocyanate by distillation, and therefore, it is considered that, in the polyisocyanate after the distillation purification, the coloration due to incorporation of the colored substance is sufficiently suppressed.

The content of the unsaturated bond compound is preferably increased so as to suppress the coloration of the polyisocyanate, whereas when the content of the unsaturated bond compound is too high, the efficiency of the distillation purification of the polyisocyanate and the unsaturated bond compound is decreased, and the yield of the polyisocyanate purified product may be decreased. Therefore, the content of the unsaturated bond compound in the present embodiment is 2.0 mass ppm or more and $1.0 \times 10^4$ mass ppm or less, and the polyisocyanate composition containing the unsaturated bond compound within the range can sufficiently suppress the coloration of the polyisocyanate while sufficiently maintaining the efficiency of the distillation purification.

From the viewpoint of further suppressing the coloration of the polyisocyanate, the content of the unsaturated bond compound is preferably 3.0 mass ppm or more, more preferably 5.0 mass ppm or more, and further preferably 10 mass ppm or more.

Furthermore, from the viewpoint of making the distillation purification more efficient, the content of the unsaturated bond compound is preferably $5.0 \times 10^3$ mass ppm or less, more preferably $3.0 \times 10^3$ mass ppm or less, and further preferably $1.0 \times 10^3$ mass ppm or less.

When the polyisocyanate composition further contains the compound represented by formula (1), the coloration of the polyisocyanate in the distillation purification tends to be further suppressed. Although the mechanism for exhibiting the effect is not clear, it is assumed that, in the distillation purification of the polyisocyanate composition, a part of the compound represented by formula (1) is thermally dissociated to generate a hydroxy compound and the hydroxy compound exhibits the similar functions as antioxidizing agents. From this viewpoint, $R^2$ in formula (1) is preferably a residue obtained by removing a hydroxy group from an aromatic hydroxy compound. In addition, although it is considered that a colored substance derived from a hydroxy compound is generated by the addition of the compound represented by formula (1), even when the colored substance is generated, by appropriately selecting the compound represented by formula (1), the polyisocyanate and the colored substance are sufficiently separated by the distillation purification. The content of the compound represented by formula (1) is preferably increased so as to suppress the coloration of the polyisocyanate.

On the other hand, when the content of the compound represented by formula (1) is too high, the efficiency of the distillation purification of the polyisocyanate and the compound represented by formula (1) is decreased, and the yield of the polyisocyanate purified product may be decreased. Therefore, in the present embodiment, the content of the compound represented by formula (1) in the polyisocyanate composition is preferably, on the basis of the total mass of the polyisocyanate composition, 2.0 mass ppm or more and $1.0 \times 10^4$ mass ppm or less. The polyisocyanate composition containing the compound represented by formula (1) within the range can sufficiently suppress the coloration of the isocyanate while sufficiently maintaining the efficiency of the distillation purification.

In the isocyanate composition, from the viewpoint of further suppressing the coloration of the polyisocyanate, the content of the compound represented by formula (1) is more preferably 3 mass ppm or more, even more preferably 5 mass ppm or more, and further preferably 10 mass ppm or more.

Furthermore, from the viewpoint of making the distillation purification more efficient, the content of the compound represented by formula (1) is more preferably $5.0 \times 10^3$ mass ppm or less, even more preferably $3.0 \times 10^3$ mass ppm or less, and further preferably $1.0 \times 10^3$ mass ppm or less.

Only one kind of the compound represented by formula (1) contained in the polyisocyanate composition may be used, or a plurality of kinds thereof may be used in combination. In addition, when a plurality of kinds of the compound represented by formula (1) is contained, the content of the compound represented by formula (1) is the sum of the plurality of kinds thereof.

The polyisocyanate composition in the present embodiment may further comprise the above-described inactive compound. When isomers exist, any of the isomers may be used, or a mixture of these isomers may be used. In addition, the content of the inactive compound described below means the sum of the content of the isomers. Fluidity of the polyisocyanate composition can be improved by blending the inactive compound.

The content of the inactive compound in the polyisocyanate composition of the present embodiment is preferably within a range exhibiting the above-described effect sufficiently, and not preventing the distillation purification or not impairing the performance of the purified polyisocyanate, and specifically, is preferably 5.0 mass ppm or more and $2.0 \times 10^4$ mass ppm or less. From the viewpoint of effectively exhibiting the above-described effect, the content of the inactive compound is more preferably 20 mass ppm or more, further preferably 100 mass ppm or more, and particularly preferably 300 mass ppm or more.

Furthermore, from the viewpoint of making the distillation purification more efficient, the content of the inactive compound is preferably $1.5 \times 10^4$ mass ppm or less, more preferably $1.3 \times 10^4$ mass ppm or less, and further preferably $1.0 \times 10^4$ mass ppm or less.

<Manufacturing Method of Purified Polyisocyanate>

A manufacturing method of a purified polyisocyanate according to the present embodiment comprises a step of obtaining a purified polyisocyanate by distillation purifying a polyisocyanate from the above-described polyisocyanate composition.

In the present embodiment, as a method of distillation purification, a conventionally-known method of distillation purification of a diisocyanate can be applied.

Materials for devices and lines in which the distillation purification of the polyisocyanate is performed may be any of those known as long as they do not have adverse effects on starting materials and reacting materials. As the materials for the devices and lines, for example, SUS304, SUS316, SUS316L or the like is inexpensive and can be preferably used.

Moreover, the form of a distillation device is not particularly limited, and a known distillation device can be used. As the distillation device, for example, known various distillation devices such as a distillation device including any of a multistage distillation column, a continuous multistage distillation column, and a packed column, and a distillation device combining them can be used.

The multistage distillation column means a distillation column having multiple plates in which the number of theoretical plates in distillation is three or more. As the multistage distillation column, for example, one that can perform continuous distillation can be appropriately used. In addition, when the number of theoretical plates is too large, the multistage distillation column becomes huge and industrial practice may be difficult, and thus, the number of theoretical plates is preferably 500 or less.

As the multistage distillation column, for example, any one that is generally used as a multistage distillation column, such as a plate column system using trays such as bubble cap trays, porous plate trays, valve trays, and countercurrent trays, and a packed column system filled with various types of packing materials such as Raschig ring, Lessing ring, Pall ring, Berl saddle, Intalox saddle, Dixon packing, McMahon packing, HELI PACK, Sulzer packing and Mellapak, can be used. Furthermore, one having a plate-packed mixed column system including both of plate parts and parts filled with packing materials is also preferably used.

The pressure at which the distillation purification is performed can be appropriately varied depending on a composition of the polyisocyanate composition to be supplied to the distillation device in which the distillation purification is performed, a temperature, a type of the distillation device and the like, and the distillation purification is performed under reduced pressure, under atmospheric pressure, or under increased pressure, but the distillation purification is generally performed preferably within a range of 0.01 kPa to 10 MPa (absolute pressure), considering easiness of industrial practice, more preferably within a range of 0.1 kPa to 1 MPa (absolute pressure), and further preferably within a range of 0.5 kPa to 50 kPa (absolute pressure).

The temperature at which the distillation purification is performed can be appropriately varied depending on a composition of the polyisocyanate composition to be supplied to the distillation device in which the distillation purification is performed, a temperature, a type of the distillation device and the like, but the polyisocyanate may be heat altered when the temperature is too high, whereas industrial practice is not easy because of requiring new equipment for cooling and the like when the temperature is too low, and thus, the distillation purification is performed preferably within a range of 50° C. to 350° C., more preferably within a range of 80° C. to 300° C., and further preferably within a range of 100° C. to 250° C.

In the above-described method, a constituent other than the unsaturated bond compound may be added so as to prepare the polyisocyanate composition. For example, on the basis of the total mass of the polyisocyanate composition, 2.0 mass ppm or more and $1.0 \times 10^4$ mass ppm or less of the compound represented by formula (1) can be further added to the polyisocyanate composition before the distillation purification.

Moreover, in the above-described method, on the basis of the total mass of the polyisocyanate, 5.0 mass ppm or more and $2.0 \times 10^4$ mass ppm or less of the inactive compound (at least one compound selected from the group consisting of compound A to compound G) can be further added to the polyisocyanate before the distillation purification.

Furthermore, the present embodiment relates to the purified polyisocyanate manufactured by the above-described method. The purified polyisocyanate of the present embodiment can sufficiently suppress the coloration due to heating and the like in the distillation purification, and can be suitably used for applications which emphasize quality such as appearance and the like.

Hereinafter, the present embodiment will be described more specifically.

(Polyisocyanate Composition)

The polyisocyanate composition of the present embodiment comprises a polyisocyanate having an isocyanate group and α-methylstyrene. In the polyisocyanate composition, the content of the polyisocyanate is, on the basis of the total mass of the polyisocyanate composition, 97 mass % or more, and the content of α-methylstyrene is, on the basis of the total mass of the polyisocyanate composition, 2.0 mass ppm or more and $1.0 \times 10^4$ mass ppm or less (0.0002 mass % or more and 1 mass % or less).

Generally, an aromatic compound, in particular, an aromatic compound having an unsaturated bond, such as styrene, tends to be oxidized, and in many cases, an aromatic compound as contaminant becomes the cause of coloration. However, in the present embodiment, α-methylstyrene effectively acts in distillation separation of the polyisocyanate and exhibits an effect of suppressing the coloration of the polyisocyanate to be distillation separated.

Although the mechanism for exhibiting the effect is not clear, it is considered that, when α-methylstyrene selectively interacts with a compound that becomes the cause of the coloration, such as oxygen, the coloration of the polyisocyanate is suppressed. Moreover, it is considered that a colored substance derived from α-methylstyrene is produced by the reaction of α-methylstyrene and the compound of the cause of the coloration, but the colored substance is sufficiently separated from the polyisocyanate by the distillation separation, and therefore, it is considered that, in the polyisocyanate after the distillation separation, the coloration due to incorporation of the colored substance is sufficiently suppressed.

The content of α-methylstyrene is preferably increased so as to suppress the coloration of the polyisocyanate, whereas when the content of α-methylstyrene is too high, the efficiency of the distillation separation of the polyisocyanate and α-methylstyrene is decreased, and the yield of the polyisocyanate purified product may be decreased. Therefore, the content of α-methylstyrene in the present embodiment is 2.0 mass ppm or more and $1.0 \times 10^4$ mass ppm or less, and the polyisocyanate composition containing α-methylstyrene within the range can sufficiently suppress the coloration of the polyisocyanate while sufficiently maintaining the efficiency of the distillation separation.

In the polyisocyanate composition, from the viewpoint of further suppressing the coloration of the polyisocyanate, the content of α-methylstyrene is preferably 3.0 mass ppm or more, more preferably 5.0 mass ppm or more, and further preferably 10 mass ppm or more.

Furthermore, from the viewpoint of making the distillation separation more efficient, the content of α-methylstyrene is preferably $5.0 \times 10^3$ mass ppm or less, more preferably $3.0 \times 10^3$ mass ppm or less, and further preferably $1.0 \times 10^3$ mass ppm or less.

The polyisocyanate of the present embodiment is not particularly limited, and for example, a polyisocyanate that can be distillation-purified can be used depending on the purpose. For example, from the viewpoint of capable of being suitably used for applications requiring weatherability and thermal yellowing resistance, an aliphatic diisocyanate and/or an alicyclic diisocyanate can be selected. In addition, for the purpose of being applied to fields not requiring weatherability and the like, an aromatic diisocyanate can also be selected.

From the viewpoint of remarkably exhibiting the effect of the present invention, the polyisocyanate may be a polyisocyanate having two or more isocyanate groups, may also be a polyisocyanate having two to four isocyanate groups, or may also be a polyisocyanate having two isocyanate groups. Furthermore, the polyisocyanate may be a compound represented by formula (10).

[Chemical Formula 21]

(10)

In the formula, c represents an integer of 2 to 4, and $R^1$ represents a c-valent organic group.

Examples of $R^1$ include an aliphatic hydrocarbon group, an alicyclic hydrocarbon group (a hydrocarbon group having an alicyclic group), and an aromatic hydrocarbon group (a hydrocarbon group having an aromatic ring).

Examples of the aliphatic hydrocarbon group include a group having 1 to 40 carbon atoms (preferably 4 to 30 carbon atoms). Moreover, specific examples of the aliphatic hydrocarbon group include groups obtained by removing c hydrogen atoms from aliphatic hydrocarbons such as butane (each isomer), pentane (each isomer), hexane (each isomer), heptane (each isomer), octane (each isomer), decane (each isomer), dodecane (each isomer), and octadecane (each isomer).

Examples of the alicyclic hydrocarbon group include a group having 6 to 40 carbon atoms (preferably 8 to 30 carbon atoms). Moreover, specific examples of the alicyclic hydrocarbon group include groups obtained by removing c hydrogen atoms from alicyclic hydrocarbons such as cyclohexane, dimethylcyclohexane (each isomer), tetramethylcyclohexane (each isomer), dicyclohexylmethane, cycloheptane, and cyclooctane.

Examples of the aromatic hydrocarbon group include a group having 6 to 40 carbon atoms (preferably 8 to 30 carbon atoms). Moreover, specific examples of the aromatic hydrocarbon group include groups obtained by removing c hydrogen atoms from aromatic hydrocarbons such as benzene, toluene, xylene (each isomer), naphthalene, diphenylmethane, and biphenyl.

Furthermore, $R^1$ may be a group which is the above-described group substituted with a substituent group, such as a halogen atom, an alkoxy group, and an alkoxycarbonyl group.

Specific examples of the polyisocyanate include tetramethylene diisocyanate, pentamethylene diisocyanate, hexamethylene diisocyanate, 2,2,4-trimethyl-1,6-diisocyanatohexane, lysine diisocyanate, isophorone diisocyanate, 1,3-bis(isocyanatomethyl)-cyclohexane, 4,4'-dicyclohexylmethane diisocyanate, 4,4'-diphenylmethane diisocyanate, toluene diisocyanate (each isomer), and lysine triisocyanate. Among them, from the viewpoint of being suitable for applications requiring weatherability and thermal yellowing resistance and being industrially easily-available, hexamethylene diisocyanate and isophorone diisocyanate are preferable. Moreover, the polyisocyanate may be used alone or a plurality of kinds thereof may be used in combination.

In the polyisocyanate composition of the present embodiment, the content of the polyisocyanate is 97 mass % or more, and preferably 98 mass % or more. In addition, the content of the polyisocyanate may be 99.5 mass % or less, or 99 mass % or less.

The polyisocyanate composition of the present embodiment may further comprise a compound in which a urethane bond is formed by the reaction of a part or all of the isocyanate groups of the polyisocyanate with phenol. That is, when the polyisocyanate is the compound represented by formula (10), the polyisocyanate composition may further comprise a compound represented by formula (1).

[Chemical Formula 22]

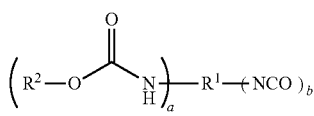
(1)

In the formula, $R^1$ is synonymous with $R^1$ in formula (10), a represents an integer of 1 to 4, b represents an integer of 0 to 3, and the sum of a and b is the same value as c in formula (10) (a+b=c).

When the polyisocyanate composition contains the compound represented by formula (1) in addition to α-methylstyrene, the coloration of the polyisocyanate in the distillation separation tends to be further suppressed. Although the mechanism for exhibiting the effect is not clear, it is assumed that, in the distillation separation of the polyisocyanate composition, a part of the compound represented by formula (1) is thermally dissociated to generate phenol, for example, in the case where $R^2$ in formula (1) is a phenyl group, and the phenol exhibits the similar functions as antioxidizing agents. In addition, although it is considered that a colored substance derived from phenol is generated by the addition of the compound represented by formula (1), even when the colored substance is generated, the polyisocyanate and the colored substance are sufficiently separated by the distillation separation.

The content of the compound represented by formula (1) is preferably increased so as to suppress the coloration of the polyisocyanate, whereas when the content of the compound represented by formula (1) is too high, the efficiency of the distillation separation of the polyisocyanate and the compound represented by formula (1) is decreased, and the yield of the polyisocyanate purified product may be decreased. Therefore, in the present embodiment, the content of the compound represented by formula (1) in the polyisocyanate composition is preferably 2.0 mass ppm or more and $1.0 \times 10^4$ mass ppm or less. The polyisocyanate composition containing the compound represented by formula (1) within the range can sufficiently suppress the coloration of the polyisocyanate while sufficiently maintaining the efficiency of the distillation separation.

In the polyisocyanate composition, from the viewpoint of further suppressing the coloration of the polyisocyanate, the content of the compound represented by formula (1) is more preferably 3 mass ppm or more, even more preferably 5.0 mass ppm or more, and further preferably 10 mass ppm or more.

Furthermore, from the viewpoint of making the distillation separation more efficient, the content of the compound represented by formula (1) is more preferably $5.0 \times 10^3$ mass ppm or less, even more preferably $3.0 \times 10^3$ mass ppm or less, and further preferably $1.0 \times 10^3$ mass ppm or less.

The polyisocyanate composition may contain only one kind of the compound represented by formula (1), or a plurality of kinds thereof. In addition, when a plurality of kinds of the compound represented by formula (1) is contained, the content of the compound represented by formula (1) is the sum of the plurality of kinds thereof.

When the polyisocyanate is a compound having two isocyanate groups (that is, when c is 2, and $R^1$ is a divalent organic group in formula (10)), examples of the compound represented by formula (1) include a compound represented by formula (1-3) and a compound represented by formula (1-4). In addition, in the formulas, $R^1$ represents a divalent organic group that is the same as $R^1$ in formula (1).

[Chemical Formula 23]

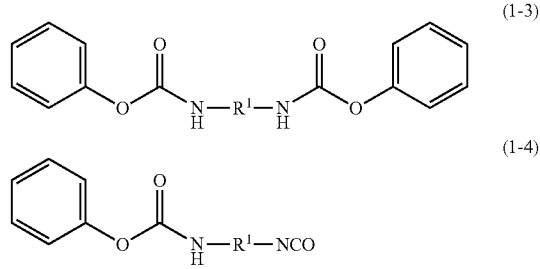

The polyisocyanate composition according to the present embodiment may further contain benzyltoluene. Benzyltoluene has three kinds of isomers represented by formulas (3-1), (3-2), and (3-3), and in the present embodiment, any of these isomers may be used, or a mixture of these isomers may be used as benzyltoluene. In addition, the content of benzyltoluene described below is the sum of the content of the isomers.

[Chemical Formula 24]

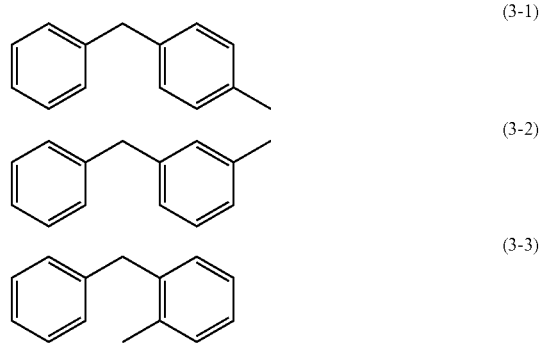

Fluidity of the polyisocyanate composition can be improved by blending benzyltoluene. Furthermore, when the polyisocyanate composition contains the compound represented by formula (1), solubility of the compound represented by formula (1) in the polyisocyanate composition can be improved by further containing benzyltoluene.

The content of benzyltoluene in the polyisocyanate composition is preferably 5.0 mass ppm or more and $2.0 \times 10^4$ mass ppm or less as a range exhibiting the above-described effect sufficiently, and not preventing the distillation separation or not impairing the performance of the polyisocyanate purified product.

From the viewpoint of effectively obtaining the above-described effect, the content of benzyltoluene is preferably 20 mass ppm or more, more preferably 100 mass ppm or more, and further preferably 300 mass ppm or more.

Furthermore, from the viewpoint of making the distillation separation more efficient, the content of benzyltoluene is preferably $1.5 \times 10^4$ mass ppm or less, more preferably $1.3 \times 10^4$ mass ppm or less, and further preferably $1.0 \times 10^4$ mass ppm or less.

Commercial benzyltoluene or the like may contain compounds represented by formulas (4-1) to (4-8), and in the present embodiment, benzyltoluene containing these compounds may be directly used or benzyltoluene purified by distillation purification or the like may be used. The content of these compounds is preferably 5 parts by mass or less with respect to 100 parts by mass of benzyltoluene.

[Chemical Formula 25]

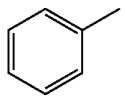 (4-1)

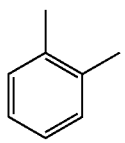 (4-2)

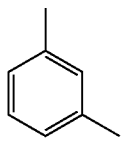 (4-3)

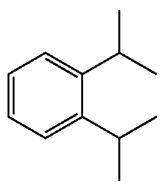 (4-4)

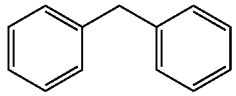 (4-5)

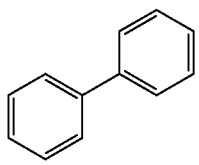 (4-6)

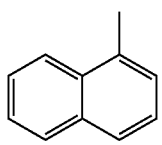 (4-7)

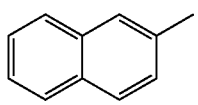 (4-8)

(Manufacturing Method of Purified Polyisocyanate)

A manufacturing method of a purified polyisocyanate (hereinafter, referred to as "polyisocyanate purified product" in some cases) according to the present embodiment comprises a step of obtaining a polyisocyanate purified product by distillation separating a polyisocyanate from the above-described polyisocyanate composition.

In the present embodiment, as a method of distillation separation, a conventionally-known method of distillation separation of a polyisocyanate can be applied.

Materials for devices and lines in which the distillation separation of the polyisocyanate is performed may be any of those known as long as they do not have adverse effects on starting materials and reacting materials. As the materials, for example, SUS304, SUS316, SUS316L or the like is inexpensive and can be preferably used.

Moreover, the form of a distillation device is not particularly limited, and a known distillation device can be used. As the distillation device, for example, known various distillation devices such as a distillation device including any of a multistage distillation column, a continuous multistage distillation column, and a packed column, and a distillation device combining them can be used.

The multistage distillation column means a distillation column having multiple plates in which the number of theoretical plates in distillation is three or more. As the multistage distillation column, for example, one that can perform continuous distillation can be appropriately used. In addition, when the number of theoretical plates is too large, the multistage distillation column becomes huge and industrial practice may be difficult, and thus, the number of theoretical plates is preferably 500 or less.

As the multistage distillation column, for example, any one that is generally used as a multistage distillation column, such as a plate column system using trays such as bubble cap trays, porous plate trays, valve trays, and countercurrent trays, and a packed column system filled with various types of packing materials such as Raschig ring, Lessing ring, Pall ring, Berl saddle, Intalox saddle, Dixon packing, McMahon packing, HELI PACK, Sulzer packing and Mellapak, can be used. Furthermore, one having a plate-packed mixed column system including both of plate parts and parts filled with packing materials is also preferably used.

The pressure at which the distillation separation is performed can be appropriately varied depending on a composition of the polyisocyanate composition to be supplied to the distillation device in which the distillation separation is performed, a temperature, a type of the distillation device and the like, and the distillation separation is performed under reduced pressure, under atmospheric pressure, or under increased pressure, but the distillation separation is generally performed preferably within a range of 0.01 kPa to 10 MPa (absolute pressure), considering easiness of industrial practice, more preferably within a range of 0.1 kPa to 1 MPa (absolute pressure), and further preferably within a range of 0.5 kPa to 50 kPa (absolute pressure).

The temperature at which the distillation separation is performed can be appropriately varied depending on a composition of the polyisocyanate composition to be supplied to the distillation device in which the distillation separation is performed, a temperature, a type of the distillation device and the like, but the polyisocyanate may be heat altered when the temperature is too high, whereas industrial practice is not easy because of requiring new equipment for cooling and the like when the temperature is too low, and thus, the distillation separation is performed preferably within a range of 50° C. to 350° C., more preferably within a range of 80° C. to 300° C., and further preferably within a range of 100° C. to 250° C.

Heretofore, the preferred embodiment of the present invention has been described, but the present invention is not limited to the above-described embodiment.

For example, one aspect of the present invention relates to a method for suppressing coloration in distillation purification of a polyisocyanate having an isocyanate group. In the method of the present aspect, on the basis of the total mass of the polyisocyanate, 2.0 mass ppm or more and $1.0 \times 10^4$ mass ppm or less of α-methylstyrene is added to the polyisocyanate before the distillation purification. The above-described isocyanate composition is prepared, and thus, the coloration in the distillation purification is sufficiently suppressed.

In the above-described method, a constituent other than α-methylstyrene may be added so as to prepare the above-described polyisocyanate composition. For example, in the above-described method, on the basis of the total mass of the polyisocyanate, 2.0 mass ppm or more and $1.0 \times 10^4$ mass ppm or less of the compound represented by formula (1) can be further added to the polyisocyanate before the distillation purification.

Moreover, in the above-described method, on the basis of the total mass of the polyisocyanate, 5.0 mass ppm or more and $2.0 \times 10^4$ mass ppm or less of benzyltoluene can be further added to the polyisocyanate before the distillation purification.

Furthermore, another aspect of the present invention relates to a purified polyisocyanate (polyisocyanate purified product) manufactured by the above-described manufacturing method of a purified polyisocyanate. Since the polyisocyanate purified product of the present aspect is obtained by the above-described method, the coloration due to heating and the like in the distillation separation is sufficiently suppressed, and the polyisocyanate purified product can be suitably used as a polyisocyanate for applications which emphasize quality of appearance.

(II) Polyisocyanate composition comprising polyisocyanate and compound represented by formula (1).

A polyisocyanate composition of the present embodiment comprises, on the basis of the total mass thereof, 97 mass % or more of a polyisocyanate, and 2.0 mass ppm or more and $1.0 \times 10^4$ mass ppm or less of a compound represented by formula (1).

[Chemical Formula 26]

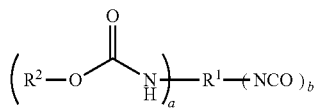

(1)

In the formula, $R^1$ represents a group synonymous with $R^1$ defined in formula (10), $R^2$ represents a monovalent organic group, a represents an integer of 1 to 5, b represents an integer of 0 to 4, the sum of a and b is c, and c is an integer of 2 to 5.

The polyisocyanate composition according to the present embodiment is effective when manufacturing an isocyanate polymer by polymerizing the polyisocyanate contained in the above-described composition and when manufacturing a composition containing the isocyanate polymer. In addition, the above-described isocyanate polymer may contain a urethane bond (a structure represented by formula (9)), an allophanate bond (a structure represented by formula (6)), a biuret bond (a structure represented by formula (4)), an isocyanurate bond (a structure represented by formula (3)) and the like.

In the polyisocyanate composition according to the present embodiment, the content of the polyisocyanate is, on the basis of the total mass of the polyisocyanate composition, 97 mass % or more, and preferably 98 mass % or more. In addition, the content of the polyisocyanate may be 99.5 mass % or less, or 99 mass % or less.

In the polyisocyanate composition according to the present embodiment, the content of the compound represented by formula (1) is preferably $2.0 \times 10^{-4}$ parts by mass or more and 1.0 part by mass or less with respect to 100 parts by mass of the polyisocyanate.

The polyisocyanate composition according to the present embodiment exhibits an effect of capable of efficiently obtaining an isocyanate polymer in a reaction of a polyisocyanate and a polyol. Surprisingly, the present inventors found that, by performing the reaction of a polyisocyanate and a polyol in a reaction system to which a predetermined amount of the compound represented by formula (1) is added, the reaction rate of the reaction of a polyisocyanate and a polyol (in particular, condensation polymerization reaction for producing urethane bond) is improved and the manufacturing efficiency of the isocyanate polymer can be improved.

Although the mechanism for exhibiting these effects is not clear, the present inventors assume that the urethane bond (—NHCOO—) of the compound represented by formula (1) accelerates the reaction of a polyisocyanate and a polyol. By making the content of the compound represented by formula (1) be $2.0 \times 10^{-4}$ parts by mass or more and 1.0 part by mass or less with respect to 100 parts by mass of the polyisocyanate, a reaction accelerating effect of the reaction of a polyisocyanate and a polyol is further improved. In addition, a urethane bond is generated also by the reaction of a polyisocyanate and a polyol, but surprisingly, there is little reaction accelerating effect in this urethane bond.

From the viewpoint of further improving the reaction rate, the additive amount of the compound represented by formula (1) is preferably $3.0 \times 10^{-4}$ parts by mass or more, more preferably $5.0 \times 10^{-4}$ parts by mass or more, and further preferably $1.0 \times 10^{-3}$ parts by mass or more with respect to 100 parts by mass of the polyisocyanate.

Moreover, from the viewpoint of sufficiently suppressing the coloration of the isocyanate polymer by the compound represented by formula (1), the additive amount of the compound represented by formula (1) is preferably 0.5 parts by mass or less, more preferably 0.3 parts by mass or less, and further preferably 0.1 parts by mass or less with respect to 100 parts by mass of the polyisocyanate.

In the above-described reaction system, only one kind of the compound represented by formula (1) may be added, or a plurality of kinds thereof may be added. In addition, when a plurality of kinds of the compound represented by formula (1) is added, the additive amount of the compound represented by formula (1) is the sum of the plurality of kinds thereof.

In the present embodiment, an unsaturated bond compound may be further added to the reaction system of the reaction of a polyisocyanate and a polyol. The addition of the unsaturated bond compound exhibits an effect of accelerating an allophanate-forming reaction (an adding reaction of an isocyanate to a urethane bond), especially.

The above-described polyol means a compound containing two or more hydroxy groups in one molecule. Examples of the polyol include dihydric alcohols to octahydric alcohols.

Examples of dihydric alcohols include ethylene glycol, diethylene glycol, triethylene glycol, propylene glycol, dipropylene glycol, tripropylene glycol, 1,2-propanediol, 1,3-propanediol, 1,2-butanediol, 1,3-butanediol, 1,4-butanediol, 2,3-butanediol, 2-methyl-1,2-propanediol, 1,5-pentanediol, 2-methyl-2,3-butanediol, 1,6-hexanediol, 1,2-hexanediol, 2,5-hexanediol, 2-methyl-2,4-pentanediol, 2,3-dimethyl-2,3-butanediol, 2-ethyl-hexanediol, 1,2-octanediol, 1,2-decanediol, 2,2,4-trimethylpentanediol, 2-butyl-2-ethyl-1,3-propanediol and 2,2-diethyl-1,3-propanediol.

Examples of trihydric alcohols include glycerin and trimethylolpropane. Examples of tetrahydric alcohols include diglycerin, ditrimethylolpropane, pentaerythritol, dipentaerythritol, and D-threitol. Examples of pentahydric alcohols include L-arabinitol, ribitol, xylitol, and L-rhamnitol. Examples of hexahydric alcohols include D-glucitol, D-mannitol, and galactitol. Examples of heptahydric alcohols include trehalose. Examples of octahydric alcohols include sucrose, maltose, gentiobiose, lactose, and melibiose. Furthermore, a compound obtained by adding ε-caprolactone or the like to the polyol can be used. The average value of the number of hydroxy groups per one molecule of the polyol used in the present embodiment is preferably 2 to 8, more preferably 2 to 6, and further preferably 2 to 4.

The allophanate-forming reaction proceeds only by heating, but generally, heating at a temperature of 150° C. or more and for several hours or more is required, and the obtained composition of the isocyanate polymer was sometimes colored after the heat history at a high temperature and for a long time. Although it is performed in the presence of a catalyst in many cases so as to solve the subject, the reaction is accelerated by the addition of the unsaturated bond compound and the amount of a catalyst required for progression of the allophanate-forming reaction can be reduced.

Using a large quantity of catalyst is considered so as to accelerate the allophanate-forming reaction. However, when using a large quantity of catalyst in the allophanate-forming reaction, efforts may be required for removing a residue of the catalyst after the completion of the reaction, and moreover, the residue of the catalyst may become the cause of coloration of the isocyanate polymer that is a manufactured article. As described above, in many cases, the isocyanate polymer is used for applications requiring high-quality appearance and excellent weatherability and durability, such as topcoat applications of automobiles and information appliances, and therefore, the coloration of the isocyanate polymer becomes an enormous problem. In the polyisocyanate composition according to the present embodiment, by adding the unsaturated bond compound, the amount of the catalyst used can be reduced while accelerating the allophanate-forming reaction, and the coloration of the isocyanate polymer can be sufficiently suppressed.

Although the mechanism for exhibiting these effects by the addition of the unsaturated bond compound is not clear, the present inventors assume that coordination of the unsaturated bond to the catalyst increases a catalytic activity.

From the viewpoint of sufficiently obtaining the effects by the addition of the unsaturated bond compound, the additive amount of the unsaturated bond compound is preferably $2.0 \times 10^{-4}$ parts by mass or more and 1.0 part by mass or less with respect to 100 parts by mass of the polyisocyanate.

Moreover, from the viewpoint of further accelerating the allophanate-forming reaction, the additive amount of the unsaturated bond compound is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the polyisocyanate.

Furthermore, from the viewpoint of preventing the coloration, the additive amount of the unsaturated bond compound is more preferably 0.5 parts by mass or less, even more preferably 0.3 parts by mass or less, and further preferably 0.1 parts by mass or less with respect to 100 parts by mass of the polyisocyanate.

In the present embodiment, an inactive compound may be further added to the reaction system of a polyisocyanate and a polyol compound. By the addition of the inactive compound, solubility of the polyisocyanate in the reaction system is improved and the reaction efficiency is further improved. Furthermore, the addition of the inactive compound also exhibits an effect of making it easy to distill away the unreacted polyisocyanate after the reaction. In this case, from the viewpoint of effectively obtaining the above-described effect, the additive amount of the inactive compound is preferably $5.0 \times 10^{-4}$ parts by mass or more, more preferably $2.0 \times 10^{-3}$ parts by mass or more, and further preferably $3.0 \times 10^{-2}$ parts by mass or more with respect to 100 parts by mass of the polyisocyanate.

Furthermore, in order to avoid incorporation of the inactive compound into the isocyanate polymer, the additive amount of the inactive compound is preferably 1.5 parts by mass or less, more preferably 1.3 parts by mass or less, and further preferably 1.0 part by mass or less with respect to 100 parts by mass of the polyisocyanate.

Hereinafter, a manufacturing method of an isocyanate polymer using the polyisocyanate composition of the present embodiment and the effect thereof will be specifically described.

<Manufacturing Method of Urethane Type Isocyanate Polymer>

In the present embodiment, a urethane compound is obtained by a urethane-forming reaction of a polyisocyanate and a polyol compound (a condensation polymerization reaction), and then, an allophanate compound is obtained by an allophanate-forming reaction of a polyisocyanate and a urethane compound (an adding reaction of an isocyanate to a urethane bond).

In the present embodiment, the urethane-forming reaction and the allophanate-forming reaction can be simultaneously performed, or after performing the urethane-forming reaction, the allophanate-forming reaction can be performed by further adding an allophanate-forming catalyst into the reaction system.

Regarding a proportion of the polyisocyanate to the polyol compound subjected to the reaction, a proportion in which the molar number of the isocyanate group of the polyisocyanate is 3 to 100 when the molar number of the hydroxy group of the polyol compound is 1 is preferable. The lower limit of the molar number of the isocyanate group of the polyisocyanate is more preferably 6, further preferably 8, and most preferably 10. Moreover, the upper limit is more preferably 80, further preferably 60, and most preferably 30. When the molar number of the isocyanate group of the polyisocyanate is excessive as 3 or more, a low-viscosity isocyanate polymer can be manufactured. Moreover, when the molar number of the isocyanate group of the polyisocyanate is 100 or less, the sufficient production efficiency can be maintained.

The urethane-forming reaction is preferably 20° C. to 200° C. The lower limit of the urethane-forming reaction temperature is more preferably 40° C., further preferably 50° C., and most preferably 60° C. Moreover, the upper limit of the urethane-forming reaction temperature is more preferably 160° C., further preferably 140° C., and most preferably 120° C. The reaction time is preferably 10 minutes to 24 hours, more preferably 15 minutes to 15 hours, and further preferably 20 minutes to 10 hours. When the reaction temperature is 20° C. or more, the sufficient reaction rate is obtained, and when the reaction temperature is 200° C. or less, the coloration can be suppressed. The urethane-forming reaction may be performed without a catalyst, or in the presence of a catalyst such as a tin-based catalyst or an amine-based catalyst.

The allophanate-forming reaction can be performed using a known allophanate-forming catalyst. Examples of a preferred catalyst include a compound containing lead, a compound containing zinc, a compound containing tin, a compound containing zirconium, a compound containing bismuth, and a compound containing lithium. One kind of these catalysts may be used alone, or two or more kinds thereof may be used in combination. The compound containing zinc, the compound containing lead, the compound containing tin, or the compound containing zirconium is preferable, and the compound containing zirconium is more preferable. Examples of the compound containing zirconium include zirconyl naphthenate and zirconyl 2-ethylhexanoate. These are particularly preferable because of being relatively inexpensive and industrially easily-available, and having high selectivity of the allophanate-forming reaction, and furthermore, high safety.

In the present embodiment, an adding method of the allophanate-forming catalyst is not limited. For example, the allophanate-forming catalyst may be added before manufacturing the urethane compound, that is, before the start of the urethane-forming reaction of a polyisocyanate and a polyol compound, may be added in the middle of the urethane-forming reaction, and may be added after manufacturing the urethane compound by the urethane-forming reaction.

Moreover, as the adding method, a requisite amount of the allophanate-forming catalyst may be added at one time or may be added by dividing into several times. Furthermore, a method for continuously adding at a constant addition rate can be adopted.

Generally, the allophanate-forming reaction is performed at a temperature of 20° C. to 200° C. The lower limit of the reaction temperature when performing the allophanate-forming reaction is more preferably 30° C., further preferably 60° C., and most preferably 80° C. Moreover, the upper limit of the reaction temperature when performing the allophanate-forming reaction is more preferably 180° C., and further preferably 160° C. When the reaction temperature is 20° C. or more, the allophanate-forming reaction can be made to proceed at an appropriate reaction rate without causing side reactions. Furthermore, when the reaction temperature is 200° C. or less, side reactions and coloration tend to be difficult to occur.

In the allophanate-forming reaction when manufacturing the isocyanate polymer, it is preferable that the conversion rate of a urethane group to an allophanate group be increased as high as possible. The conversion rate is preferably 80% or more, more preferably 90% or more, and further preferably 92% or more. By sufficiently increasing the conversion rate of a urethane group to an allophanate group, the average value of the number of isocyanate groups (fn) in the isocyanate polymer can be increased while keeping the viscosity relatively low. The average value of the number of isocyanate groups (fn) means a statistical average value of the number of isocyanate groups contained in one molecule of the isocyanate polymer, and is calculated by the following equation.

average value of the number of isocyanate groups (fn)=(number average molecular weight of isocyanate polymer×mass % of isocyanate groups× 0.01)/42

The average value of the number of isocyanate groups in the isocyanate polymer containing an allophanate group obtained in the present embodiment is preferably 2.5 or more. Furthermore, it is more preferably 2.8 or more, further preferably 3.0 or more, and most preferably 3.2 or more.

If the average value of the number of isocyanate groups is 2.5 or more, a cross-linkage property when being used as a curing agent for a coating material can be exhibited. Although the urethane-forming reaction and the allophanate-forming reaction can be performed in the absence of a solvent, as necessary, an organic solvent which does not have the reactivity with the isocyanate groups, such as butyl acetate, methyl ethyl ketone, toluene, xylene, hydrocarbon solvents, and aromatic solvents, can be used as a solvent.

Progression of the reaction of a polyisocyanate and a polyol compound can be traced by measuring a concentration of the isocyanate groups of the reaction mixture or measuring a refractive index.

The allophanate-forming reaction can be terminated by being cooled to room temperature or by adding a reaction-terminating agent. In the case of using the allophanate-forming catalyst, it is preferable that the allophanate-forming reaction be terminated by adding the reaction-terminating agent because the stability of the isocyanate polymer is improved.

The additive amount of the reaction-terminating agent is 0.2 to 100 times of molar quantity, preferably 0.5 to 50 times of molar quantity, and more preferably 1.0 to 20 times of molar quantity with respect to the allophanate-forming catalyst. In the case of 0.2 times or more, the allophanate-forming catalyst can be sufficiently deactivated. Moreover, in the case of 100 times or less, occurrence of turbidity and the like of the composition containing the isocyanate polymer due to a residue of the reaction-terminating agent can be sufficiently suppressed.

The reaction-terminating agent is not particularly limited as long as it deactivates the allophanate-forming catalyst. Examples of the reaction-terminating agent include compounds showing phosphoric acid acidity, such as phosphoric acid, pyrophosphoric acid, metaphosphoric acid, and polyphosphoric acid, monoalkyl esters or dialkyl esters of phosphoric acid, pyrophosphoric acid, metaphosphoric acid, and polyphosphoric acid; halogenated acetic acids such as monochloroacetic acid; benzoyl chloride; sulfonic acid ester; sulfuric acid; sulfate ester; ion-exchange resins; and chelating agents.

Moreover, industrially, as the reaction-terminating agent, phosphoric acid, pyrophosphoric acid, metaphosphoric acid, polyphosphoric acid, phosphate monoalkyl esters, or phosphate dialkyl esters are preferable in that they are difficult to corrode stainless steel. Examples of phosphate monoesters and phosphate diesters include phosphate monoethyl ester, phosphate diethyl ester, phosphate monobutyl ester, phosphate dibutyl ester, phosphate mono(2-ethylhexyl)ester, and phosphate di(2-ethylhexyl)ester.

Furthermore, phosphoric acid, pyrophosphoric acid, metaphosphoric acid, and polyphosphoric acid not substantially containing water are more preferable as the reaction-terminating agent. When the reaction-terminating agent not substantially containing water is used, a reaction product of the reaction-terminating agent and the catalyst becomes easy to be precipitated, and thus, there is an effect that the reaction product of the reaction-terminating agent and the catalyst becomes difficult to remain in the composition containing the isocyanate polymer.

Furthermore, when the reaction-terminating agent not substantially containing water is used, generation of a reaction product of water and an isocyanate can be suppressed, and there are effects that viscosity increase of the composition containing the isocyanate polymer is difficult to occur, and reducibility with respect to an organic solvent is difficult to be decreased. In addition, the term "not substantially containing water" means that water may be contained as long as the above-described effects are exhibited, and specifically, less than 5.0 mass %, preferably less than 2.0 mass %, and further preferably less than 0.50 mass % of water may be contained with respect to the reaction-terminating agent.

In addition, as another preferred reaction-termination method when using the allophanate-forming catalyst, there is a method for adsorbing a catalyst with an adsorbent. Furthermore, the reaction may be terminated by combining the adsorbent and the above-described reaction-terminating agent. Examples of the above-described adsorbent include silica gel, activated carbon, and activated alumina. The additive amount of the adsorbent is preferably 0.05 to 10 mass % with respect to the mass of the polyisocyanate used in the reaction.

After the completion of the reaction, the unreacted polyisocyanate and the solvent can be separated from the composition containing the isocyanate polymer by treatment such as a thin-film distillation method and a solvent extraction method.

The concentration of the polyisocyanate contained in the composition containing the isocyanate polymer is preferably controlled to be 1 mass % or less by performing the above-described treatment. The upper limit of the polyisocyanate concentration in the composition containing the above-described isocyanate polymer is more preferably 0.7 mass % or less, further preferably 0.5 mass % or less, and particularly preferably 0.3 mass % or less. By making the polyisocyanate concentration be the above-described upper limit or less, toxicity of the composition containing the isocyanate polymer can be further reduced, and safety can be increased.

In the present embodiment, the urethane-forming reaction and the allophanate-forming reaction can be performed in one reactor. Moreover, in the present embodiment, two reactors are connected, and a step of the urethane-forming reaction and a step of the allophanate-forming reaction can be separately performed.

Furthermore, in the present embodiment, several reactors are arranged in tandem, and the urethane-forming reaction and the allophanate-forming reaction can be continuously performed.

Hereinafter, the present embodiment will be described more specifically.

(Polyisocyanate Composition)

The polyisocyanate composition according to the present embodiment is obtained by a reaction of an isocyanate compound represented by formula (1) and a polyol compound having two or more hydroxy groups, and comprises an allophanate compound having at least one allophanate group and two or more isocyanate groups.

[Chemical Formula 27]

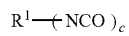

(10)

In the formula, c represents an integer of 2 to 4, and $R^1$ represents a c-valent organic group.

The isocyanate compound is not particularly limited as long as it is the compound represented by formula (10), and can be appropriately varied depending on an intended polyisocyanate composition. For example, from the viewpoint of obtaining a polyisocyanate composition capable of being suitably used for applications requiring weatherability, an aliphatic diisocyanate and/or an alicyclic diisocyanate are preferable. In addition, for the purpose of being applied to fields not requiring weatherability and the like, an aromatic diisocyanate can also be selected.

Examples of $R^1$ include an aliphatic hydrocarbon group, an alicyclic hydrocarbon group (a hydrocarbon group having an alicyclic group), and an aromatic hydrocarbon group (a hydrocarbon group having an aromatic ring).

Examples of the aliphatic hydrocarbon group include a group having 1 to 40 carbon atoms (preferably 4 to 30 carbon atoms). Moreover, specific examples of the aliphatic hydrocarbon group include groups obtained by removing c hydrogen atoms from aliphatic hydrocarbons such as butane (each isomer), pentane (each isomer), hexane (each isomer), heptane (each isomer), octane (each isomer), decane (each isomer), dodecane (each isomer), and octadecane (each isomer).

Examples of the alicyclic hydrocarbon group include a group having 6 to 40 carbon atoms (preferably 8 to 30 carbon atoms). Moreover, specific examples of the alicyclic hydrocarbon group include groups obtained by removing c hydrogen atoms from alicyclic hydrocarbons such as cyclohexane, dimethylcyclohexane (each isomer), tetramethylcyclohexane (each isomer), dicyclohexylmethane, cycloheptane, and cyclooctane.

Examples of the aromatic hydrocarbon group include a group having 6 to 40 carbon atoms (preferably 8 to 30 carbon atoms). Moreover, specific examples of the aromatic hydrocarbon group include groups obtained by removing c hydrogen atoms from aromatic hydrocarbons such as benzene, toluene, xylene (each isomer), naphthalene, diphenylmethane, and biphenyl.

Furthermore, $R^1$ may be a group obtained by substituting the above-described group with a substituent group, such as a halogen atom, an alkoxy group, and an alkoxycarbonyl group.

Specific examples of the isocyanate compound include tetramethylene diisocyanate, pentamethylene diisocyanate, hexamethylene diisocyanate, 2,2,4-trimethyl-1,6-diisocyanatohexane, lysine diisocyanate, isophorone diisocyanate, 1,3-bis(isocyanatomethyl)-cyclohexane, 4,4'-dicyclohexylmethane diisocyanate, 4,4'-diphenylmethane diisocyanate, toluene diisocyanate (each isomer), and lysine triisocyanate. Among them, from the viewpoint of being suitable for applications requiring weatherability and thermal yellowing resistance and being industrially easily-available, hexamethylene diisocyanate and isophorone diisocyanate are preferable. Moreover, the isocyanate compound may be used alone or a plurality of kinds thereof may be used in combination.

The polyol compound is a compound having two or more hydroxy groups. Examples of the polyol compound include a polyester polyol. In addition, the polyol compound may be used alone or two or more kinds thereof may be used in combination.

The polyol compound is preferably a polyester polyol obtained from a dihydric to trihydric alcohol and ε-caprolactone, and the number average molecular weight of the polyester polyol is preferably 250 to 2000. Moreover, the upper limit of the number average molecular weight of the polyester polyol is preferably 1800, more preferably 1400, and further preferably 1000. When the number average molecular weight is within the preferred range, a coating composition using the obtained polyisocyanate composition excels in extensibility of a coating film, and viscosity of the coating composition is within a practically preferred range.

Examples of the above-described dihydric to trihydric alcohol include 1,2-propylene glycol, 1,3-butylene glycol, neopentyl glycol, hydroxypivalinic acid ester of neopentyl glycol, 2-methyl-1,3-propanediol, 2,3,5-trimethylpentanediol, ethylene glycol, diethylene glycol, 1,3-propanediol, 1,4-butylenediol, 1,5-pentanediol, 1,6-hexanediol, trimethylolpropane, glycerin, 1,1,7-trimethylolheptane, and 1,2,7-trimethylolheptane. One kind of them may be used or two or more kinds of them may be used in combination.

The polyisocyanate composition comprises at least an allophanate compound. The allophanate compound is a compound in which an isocyanate compound is further added to the urethane bond of the urethane compound that is a condensation polymerization product of an isocyanate compound and a polyol compound.

From the aspect of the amount of an organic solvent and the number of functional groups, the viscosity of the polyisocyanate composition is preferably 500 to 15000 mPa·s. In the case of 500 mPa·s or more, the number of functional groups can be sufficiently increased, and in the case of 15000 mPa·s or less, the amount of an organic solvent can be sufficiently reduced. The viscosity of the polyisocyanate composition is more preferably 600 to 12000 mPa·s, and further preferably 700 to 10000 mPa·s. In addition, the viscosity described here is a value measured at 25° C. using E-type viscometer (TOKIMEC Inc.).

From the viewpoint of excelling in curability and showing good viscosity, a number average functional group number (hereinafter, referred to as "fn") of the polyisocyanate composition is preferably 3.5 to 7.0. When fn is 3.5 or more, sufficient curability is obtained, and when fn is 7.0 or less, viscosity does not become too high. fn of the polyisocyanate composition is preferably 3.6 to 6.9, and more preferably 3.7 to 6.8.

In addition, fn of the polyisocyanate composition is determined by the following equation.

(fn of polyisocyanate composition)=(number average molecular weight)×NCO %/4200

The number average molecular weight is determined from gel filtration chromatography (hereinafter, referred to as GPC). Specifically, HLC-8120 (manufactured by TOSOH CORPORATION) is used as equipment used, TSK GEL SuperH1000, TSK GEL SuperH2000, and TSK GEL SuperH3000 (all manufactured by TOSOH CORPORATION) are used as columns, a sample concentration is 5 mass %, tetrahydrofuran is used as a developer, a developer flow rate is 0.6 mL/min, a differential refractometer is used as a detector, and calibration curves prepared by using, as standards, polystyrenes having a molecular weight of 50000 to 2050 (PSS-06 (weight average molecular weight 50000), BK13007 (peak top molecular weight=20000, weight average molecular weight/number average molecular weight=1.03), PSS-08 (weight average molecular weight=9000), PSS-09 (weight average molecular weight=4000), 5040-35125 (peak top molecular weight=2050, weight average molecular weight/number average molecular weight=1.05) manufactured by GL Sciences Inc.), and a trimer to heptamer of an isocyanurate modification (molecular weight of isocyanurate trimer=504, molecular weight of isocyanurate pentamer=840, molecular weight of isocyanurate heptamer=1176) and hexamethylene diisocyanate (molecular weight=168) of the HMDI type polyisocyanate composition (DURANATE TPA-100 manufactured by Asahi Kasei Chemicals Corporation) are used so that the number average molecular weight is determined. In addition, the number average molecular weights of the polyisocyanate composition, the polyol compound and the like of the present embodiment are all determined by the above-described method.

NCO % of the polyisocyanate composition (proportion of mass of isocyanate group per unit mass of solid content of polyisocyanate composition) is, on the basis of 100% of the solid content, preferably 3.0% to 25.0%. In the case of 3.0% or more, better performance tends to be shown when a coating composition using the polyisocyanate composition is formed into a coating film, and in the case of 25.0% or less, the crosslink density does not become too high and a coating film difficult to break is formed. NCO % of the polyisocyanate composition is more preferably 3.2% to 24.0%, and further preferably 3.4% to 23.0%. In addition, NCO % can be determined by back titration with 1N hydrochloric acid after neutralizing the isocyanate group with excessive 2N amine.

The polyisocyanate composition preferably contains an allophanate group and does not substantially contain an isocyanurate group. Here, not substantially contain an isocyanurate group means that the molar ratio of the allophanate group and the isocyanurate group is 91/9 to 100/0. The ratio is preferably 93/7 to 100/0, more preferably 95/5 to 100/0, and further preferably 97/3 to 100/0. When the molar ratio of the allophanate group and the isocyanurate group is within the range of 91/9 to 100/0, viscosity of the polyisocyanate composition can be sufficiently reduced, and a coating film which excels in extensibility can be formed by a coating composition using the polyisocyanate composition.

Since a uretdione modification is easy to be dissociated by heat and the like to generate a diisocyanate compound, the polyisocyanate composition preferably has a low uretdione modification content. The content of the uretdione modification is, on the basis of the total amount of the solid content of the polyisocyanate composition, preferably 10 mass % or less, more preferably 8 mass % or less, and further preferably 5 mass % or less.

The content of the uretdione modification can be determined by measuring a proportion of an area of a peak at a molecular weight of about 336 by gel filtration chromatography (hereinafter, referred to as GPC) using a differential refractometer. In addition, if there is a peak that impedes the measurement in the vicinity of the peak at a molecular weight of about 336, the content of the uretdione modification can be determined using FT-IR by a method for quantitating a ratio of a height of a peak of the uretdione group at about 1770 cm$^{-1}$ and a height of a peak of the allophanate group at about 1720 cm$^{-1}$ using an internal standard.

In the polyisocyanate composition, a biuret modification and other isocyanate polymers may have adverse effects on weatherability and the like of the coating film, and thus, it is not preferable that the contents thereof be high. As a range of the content of the biuret modification and other isocyanate polymers in the polyisocyanate composition, on the basis of the total amount of the solid content of the polyisocyanate composition, preferably 10 mass % or less, more preferably 5 mass % or less, and further preferably 3 mass % or less are appropriate.

In the polyisocyanate composition, a urethane modification may increase adhesion with a base material, but if the content thereof is too high, a number average functional group number is decreased and a cross-linkage property may be decreased. As a range of the content of the urethane modification, when it is expressed by a ratio (mol %) of the molar number of a urethane group with respect to the sum of the molar numbers of an allophanate group and an isocyanurate group, preferably less than 10 mol %, more preferably 8 mol % or less, and further preferably 6 mol % or less are appropriate.

The mol % of the urethane group can be determined by using $^1$H-NMR. A specific example of a measurement method of $^1$H-NMR is as follows.

Example of Measurement Method of $^1$H-NMR:

The polyisocyanate composition is dissolved in deuterochloroform at a concentration of 10 mass %, and with respect to the polyisocyanate composition, 0.03 mass % of tetramethylsilane is added. A signal of hydrogen atoms of tetramethylsilane is used as a standard of a chemical shift, and the signal is defined as 0 ppm. A $^1$H-NMR measurement is performed, and the allophanate group can be quantitated from a ratio of an area of a signal of a hydrogen atom bonded to a nitrogen atom of the allophanate group in the vicinity of 8.5 ppm (1 mol of hydrogen atoms with respect to 1 mol of allophanate groups) and an area of the signal of hydrogen atoms of tetramethylsilane. Moreover, the isocyanurate group can be quantitated from a ratio of an area of a signal of hydrogen atoms of methylene groups adjacent to the isocyanurate group in the vicinity of 3.85 ppm (6 mol of hydrogen atoms with respect to 1 mol of isocyanurate groups) and an area of the signal of hydrogen atoms of tetramethylsilane. Furthermore, the urethane group can be quantitated from a ratio of an area of a signal of a hydrogen atom bonded to nitrogen of the urethane group in the vicinity of 4 to 5 ppm (1 mol of hydrogen atoms with respect to 1 mol of urethane groups) and an area of the signal of hydrogen atoms of tetramethylsilane.

In the polyisocyanate composition, the remained amount of the isocyanate compound is, on the basis of the total amount of the solid content, preferably 5 mass % or less, and more preferably 2 mass % or less. In addition, the remained amount of the isocyanate compound can be measured by methods such as gas chromatography.

(Manufacturing Method of Polyisocyanate Composition)

In a manufacturing method of a polyisocyanate composition according to the present embodiment, a product can be obtained by a reaction of an isocyanate compound and a polyol compound. More specifically, it can be obtained by adding an isocyanate compound to the urethane bond of the urethane compound that is a condensation polymerization product of an isocyanate compound and a polyol compound.

In the present embodiment, the reaction of an isocyanate compound and a polyol compound is performed in a reaction system to which $2.0 \times 10^{-4}$ parts by mass or more and 1.0 part by mass or less of the compound represented by formula (1) is added with respect to 100 parts by mass of the isocyanate compound.

[Chemical Formula 28]

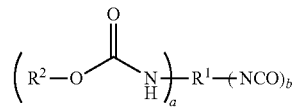

(1)

In the formula, $R^1$ is synonymous with $R^1$ in formula (10), a represents an integer of 1 to 4, b represents an integer of 0 to 3, and the sum of a and b is the same value as c in formula (10) (a+b=c).

According to the manufacturing method, the polyisocyanate composition can be efficiently obtained. Surprisingly, the present inventors found that, by performing the reaction of an isocyanate compound and a polyol compound in a reaction system to which a predetermined amount of the compound represented by formula (1) is added, the reaction rate of the reaction of an isocyanate compound and a polyol compound (in particular, condensation polymerization reaction for producing urethane compound) is improved and the manufacturing efficiency of the polyisocyanate composition can be improved.

Although the mechanism for exhibiting these effects is not clear, the present inventors assume that the urethane bond (—NHCOO—) of the compound represented by formula (1) accelerates the reaction of an isocyanate composition and a polyol compound. In order to effectively exhibit the effects, the additive amount of the compound represented by formula (1) is $2.0 \times 10^{-4}$ parts by mass or more and 1.0 part by mass or less with respect to 100 parts by mass of the isocyanate compound. In addition, a urethane bond is generated also by the reaction of an isocyanate compound and a polyol compound, but surprisingly, there is little improvement effect of the reaction rate in this urethane bond.

From the viewpoint of further improving the reaction rate, the additive amount of the compound represented by formula (1) is preferably $3.0 \times 10^{-4}$ parts by mass or more, more preferably $5.0 \times 10^{-4}$ parts by mass or more, and further preferably $1.0 \times 10^{-3}$ parts by mass or more with respect to 100 parts by mass of the isocyanate compound.

Moreover, from the viewpoint of sufficiently suppressing the coloration of the polyisocyanate composition by the compound represented by formula (1), the additive amount of the compound represented by formula (1) is preferably 0.5 parts by mass or less, more preferably 0.3 parts by mass or less, and further preferably 0.1 parts by mass or less with respect to 100 parts by mass of the isocyanate compound.

In the above-described reaction system, only one kind of the compound represented by formula (1) may be added, or a plurality of kinds thereof may be added. In addition, when a plurality of kinds of the compound represented by formula (1) is added, the additive amount of the compound represented by formula (1) is the sum of the plurality of kinds thereof.

When the isocyanate compound is a compound having two isocyanate groups (that is, when c in formula (10) is 2, and $R^1$ is a divalent organic group), examples of the compound represented by formula (1) include a compound represented by formula (1-3) and a compound represented by formula (1-4). In addition, in the formulas, $R^1$ represents a divalent organic group that is the same as $R^1$ in formula (1).

[Chemical Formula 29]

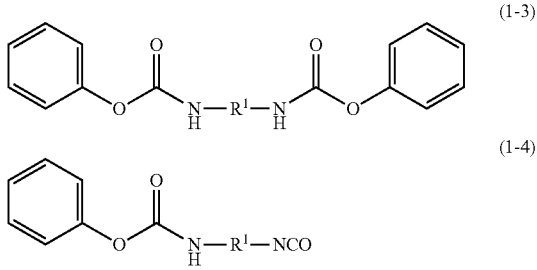

(1-3)

(1-4)

In the present embodiment, α-methylstyrene may be further added to the reaction system of the reaction of an isocyanate compound and a polyol compound. The addition of α-methylstyrene exhibits an effect of accelerating an allophanate-forming reaction (an adding reaction of an isocyanate compound to a urethane bond), especially.

Although the allophanate-forming reaction is performed in the presence of a catalyst in many cases, the reaction is accelerated by the addition of α-methylstyrene, and thus, the amount of a catalyst required for the allophanate-forming reaction can be reduced.

Using a large quantity of catalyst is considered so as to accelerate the allophanate-forming reaction. However, when using a large quantity of catalyst in the allophanate-forming reaction, efforts may be required for removing a residue of the catalyst after the completion of the reaction, and moreover, the residue of the catalyst may become the cause of coloration of the polyisocyanate composition that is a manufactured article. As described above, in many cases, the polyisocyanate composition is used for applications requiring high-quality appearance and excellent weatherability and durability, such as topcoat applications of automobiles and information appliances, and therefore, the coloration of the polyisocyanate composition becomes an enormous problem. In the present embodiment, by the addition of α-methylstyrene, the amount of the catalyst used can be reduced while accelerating the allophanate-forming reaction, and the coloration of the polyisocyanate composition that is a manufactured article can be sufficiently suppressed.

Although the mechanism for exhibiting these effects by the addition of α-methylstyrene is not clear, the present inventors assume that one of the causes is that coordination of the unsaturated bond of α-methylstyrene to the catalyst increases a catalytic activity.

From the viewpoint of sufficiently obtaining the effects by the addition of α-methylstyrene, the additive amount of α-methylstyrene is preferably $2.0 \times 10^{-4}$ parts by mass or more and 1.0 part by mass or less with respect to 100 parts by mass of the isocyanate compound.

Moreover, from the viewpoint of further accelerating the allophanate-forming reaction, the additive amount of α-methylstyrene is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the isocyanate compound.

Furthermore, from the viewpoint of preventing the coloration, the additive amount of α-methylstyrene is more preferably 0.5 parts by mass or less, even more preferably 0.3 parts by mass or less, and further preferably 0.1 parts by mass or less with respect to 100 parts by mass of the isocyanate compound.

In the present embodiment, benzyltoluene may be further added to the reaction system of the reaction of an isocyanate compound and a polyol compound. By the addition of benzyltoluene, solubility of the isocyanate compound in the reaction system is improved and the reaction efficiency is further improved. Furthermore, the addition of benzyltoluene also exhibits an effect of making it easy to distill away the unreacted isocyanate compound after the reaction.

Benzyltoluene has three kinds of isomers represented by formulas (3-1), (3-2), and (3-3), and in the present embodiment, any of these isomers may be used, or a mixture of these isomers may be used as benzyltoluene. In addition, the content of benzyltoluene is the sum of the content of the isomers.

[Chemical Formula 30]

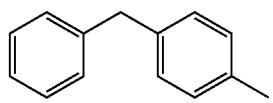

(3-1)

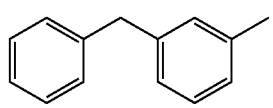

(3-2)

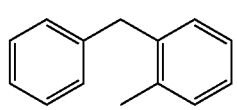

(3-3)

From the viewpoint of effectively obtaining the above-described effect, the additive amount of benzyltoluene is preferably $5.0 \times 10^{-4}$ parts by mass or more, more preferably $2.0 \times 10^{-3}$ parts by mass or more, and further preferably $3.0 \times 10^{-2}$ parts by mass or more with respect to 100 parts by mass of the isocyanate compound.

Furthermore, in order to avoid remaining of benzyltoluene in the polyisocyanate composition that is a manufactured article, the additive amount of benzyltoluene is preferably 1.5 parts by mass or less, more preferably 1.3 parts by mass or less, and further preferably 1.0 part by mass or less with respect to 100 parts by mass of the isocyanate compound.

In addition, commercial benzyltoluene or the like may contain compounds represented by formulas (4-1) to (4-8), and in the present embodiment, benzyltoluene containing these compounds may be directly used or benzyltoluene purified by distillation purification or the like may be used. In addition, the content of these compounds in the reaction system is preferably 10 parts by mass or less with respect to 100 parts by mass of benzyltoluene.

[Chemical Formula 31]

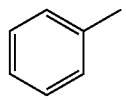

(4-1)

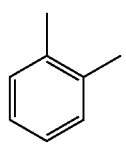

(4-2)

-continued

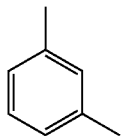
(4-3)

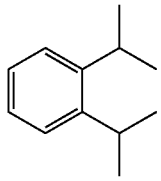
(4-4)

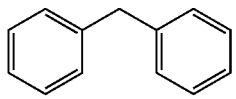
(4-5)

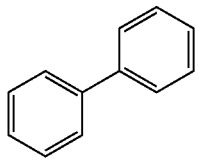
(4-6)

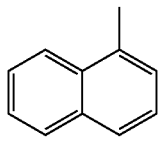
(4-7)

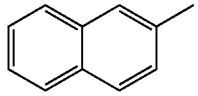
(4-8)

In the present embodiment, a urethane compound is obtained by a urethane-forming reaction of an isocyanate compound and a polyol compound (a condensation polymerization reaction), and then, an allophanate compound is obtained by an allophanate-forming reaction of an isocyanate compound and a urethane compound (an adding reaction of an isocyanate compound to a urethane bond).

In the present embodiment, the urethane-forming reaction and the allophanate-forming reaction can be simultaneously performed, or after performing the urethane-forming reaction, the allophanate-forming reaction can be performed by adding an allophanate-forming catalyst into the reaction system or the like.

Regarding a proportion of the isocyanate compound to the polyol compound subjected to the reaction, a proportion in which a ratio of the molar number of the isocyanate group of the isocyanate compound to the molar number of the hydroxy group of the polyol compound is 6/1 to 100/1 is preferable. The ratio is preferably 8/1 to 80/1, and more preferably 10/1 to 60/1. When the isocyanate group is excessive, that is the ratio is 6/1 or more, a low-viscosity polyisocyanate composition can be manufactured. Moreover, when the hydroxy group exists such that the ratio is 100/1 or more, the sufficient production efficiency can be maintained.

The urethane-forming reaction is performed at preferably 20° C. to 200° C., more preferably 40° C. to 150° C., and further preferably 60° C. to 120° C. The reaction time is preferably 10 minutes to 24 hours, more preferably 15 minutes to 15 hours, and further preferably 20 minutes to 10 hours. When the reaction temperature is 20° C. or more, the sufficient reaction rate is obtained, and when the reaction temperature is 200° C. or less, the coloration can be suppressed. The urethane-forming reaction may be performed without a catalyst, or in the presence of a catalyst such as a tin-based catalyst or an amine-based catalyst.

The allophanate-forming reaction can be performed using a known allophanate-forming catalyst. Examples of a preferred catalyst include a compound containing lead, a compound containing zinc, a compound containing tin, a compound containing zirconium, a compound containing bismuth, and a compound containing lithium. One kind or two or more kinds of these compounds may be used.

Among them, the compound containing zinc, the compound containing lead, the compound containing tin, and the compound containing zirconium are more preferable, and the compound containing zirconium is further more preferable. Examples of the compound containing zirconium include zirconyl naphthenate and zirconyl 2-ethylhexanoate. These are particularly preferable because of being relatively inexpensive and industrially easily-available, and having high selectivity of the allophanate-forming reaction, and furthermore, high safety.

In the present embodiment, an adding method of the allophanate-forming catalyst is not limited. For example, the allophanate-forming catalyst may be added before manufacturing the urethane compound, that is, before the urethane-forming reaction of an isocyanate compound and a polyol compound, may be added in the middle of the urethane-forming reaction of an isocyanate compound and a polyol compound, and may be added after manufacturing the urethane compound by the urethane-forming reaction.

Moreover, as the adding method, a requisite amount of the allophanate-forming catalyst may be added at one time or may be added by dividing into several times. Furthermore, a method for continuously adding at a constant addition rate can be adopted.

Generally, the allophanate-forming reaction is performed at a temperature of 20 to 200° C. It is preferably 30 to 180° C., and more preferably 60 to 160° C. When the reaction temperature is 20° C. or more, the allophanate-forming reaction can be made to proceed at an appropriate reaction rate without causing side reactions. When the reaction temperature is 200° C. or less, side reactions and coloration can be prevented from occurring.

In the allophanate-forming reaction when manufacturing the polyisocyanate composition, it is preferable that the conversion rate of a urethane group to an allophanate group be increased as high as possible. The conversion rate is preferably 91% or more, and more preferably 92% or more. By sufficiently increasing the conversion rate of a urethane group to an allophanate group, fn of the isocyanate group can be increased while keeping the viscosity relatively low.

Although the urethane-forming reaction and the allophanate-forming reaction can be performed in the absence of a solvent, as necessary, an organic solvent which does not have the reactivity with the isocyanate groups, such as butyl acetate, methyl ethyl ketone, toluene, xylene, hydrocarbon solvents, and aromatic solvents, can be used as a solvent.

The process of the reaction of an isocyanate compound and a polyol compound can be traced by measuring NCO % of the reaction mixture or measuring a refractive index.

Although the allophanate-forming reaction can be terminated by being cooled to room temperature or by adding a reaction-terminating agent, in the case of using the allophanate-forming catalyst, it is preferable that the allophanate-forming reaction be terminated by adding the reaction-terminating agent because the stability of the polyisocyanate composition is improved.

The additive amount of the reaction-terminating agent is 0.2 to 100 times of molar quantity, preferably 0.5 to 50 times of molar quantity, and more preferably 1.0 to 20 times of molar quantity with respect to the allophanate-forming catalyst. In the case of 0.2 times or more, the catalyst can be sufficiently deactivated. Moreover, in the case of 100 times or less, occurrence of turbidity and the like of the polyisocyanate composition due to a residue of the reaction-terminating agent can be sufficiently suppressed.

The reaction-terminating agent is not particularly limited as long as it deactivates the allophanate-forming catalyst. Examples of the reaction-terminating agent include compounds showing phosphoric acid acidity, such as phosphoric acid, pyrophosphoric acid, metaphosphoric acid, and polyphosphoric acid; monoalkyl or dialkyl esters of phosphoric acid, pyrophosphoric acid, metaphosphoric acid, and polyphosphoric acid; halogenated acetic acids such as monochloroacetic acid; benzoyl chloride; sulfonic ester; sulfuric acid; sulfate ester; ion-exchange resins; and chelating agents.

Industrially, phosphoric acid, pyrophosphoric acid, metaphosphoric acid, polyphosphoric acid, phosphate monoalkyl esters, and phosphate dialkyl esters are preferable because they are difficult to corrode stainless steel. Examples of phosphate monoesters and phosphate diesters include phosphate monoethyl ester, phosphate diethyl ester, phosphate monobutyl ester, phosphate dibutyl ester, phosphate mono (2-ethylhexyl)ester, and phosphate di(2-ethylhexyl)ester.

Moreover, phosphoric acid, pyrophosphoric acid, metaphosphoric acid, and polyphosphoric acid not substantially containing water are more preferable as the terminating agent. When being used in a state of not containing water, a reaction product of the terminating agent and the catalyst becomes easy to be precipitated, and thus, there is an effect that the reaction product of the terminating agent and the catalyst becomes difficult to remain in the polyisocyanate composition.

Furthermore, when being used in a state of not containing water, since a reaction product of water and an isocyanate is not incorporated into the polyisocyanate composition, there are effects that viscosity increase of the polyisocyanate composition is difficult to occur, and reducibility with respect to an organic solvent is not decreased. In addition, not substantially containing water in the present invention means that water may be contained as long as the above-described effects are exhibited, and a rough indication thereof is less than 5.0 mass %, preferably less than 2.0 mass %, and further preferably less than 0.50 mass % with respect to the terminating agent.

In addition, examples of another preferred termination method when using the allophanate-forming catalyst include a method for terminating the reaction by adsorbing a catalyst with an adsorbent. Furthermore, termination by the combination of the adsorbent and the above-described reaction-terminating agent is also a preferred method. Examples of the adsorbent include silica gel, activated carbon, and activated alumina. The additive amount of the adsorbent is preferably an additive amount of 0.05 to 10 mass % with respect to the isocyanate compound used in the reaction.

After the completion of the reaction, the unreacted isocyanate compound and the solvent can be separated from the polyisocyanate composition by a thin-film distillation method and a solvent extraction method, for example.

In the present embodiment, the urethane-forming reaction and the allophanate-forming reaction can be performed in one reactor. Moreover, two reactors are connected, and a step of the urethane-forming reaction and a step of the allophanate-forming reaction can be separately performed. Alternatively, by arranging several reactors in tandem, the urethane-forming reaction and the allophanate-forming reaction can be continuously performed.

Heretofore, the preferred embodiment of the present invention has been described, but the present invention is not limited to the above-described embodiment.

That is, one aspect of the present invention may be a manufacturing method of a urethane compound in which a urethane compound having a urethane bond is obtained by the above-described step of the urethane-forming reaction. According to the present aspect, the urethane-forming reaction is accelerated by the addition of the compound represented by formula (1), and thus, the urethane compound can be efficiently obtained.

Moreover, another aspect of the present invention may be an isocyanate composition used for the above-described manufacturing method of a polyisocyanate composition or the above-described manufacturing method of a urethane compound. In the above-described manufacturing method, the isocyanate compound and the compound represented by formula (1) may be separately subjected to the reaction system, or the isocyanate composition containing the isocyanate compound and the compound represented by formula (1) is prepared in advance, and then, the isocyanate composition may be subjected to the reaction system.

That is, the isocyanate composition of the present aspect contains the isocyanate compound and, with respect to 100 parts by mass of the isocyanate composition, $2.0 \times 10^{-3}$ parts by mass or more and 2.0 parts by mass or less of the compound represented by formula (1). By preparing the isocyanate composition, the above-described manufacturing method can be easily performed.

On the basis of the total mass of the isocyanate composition, the content of the isocyanate compound in the isocyanate composition may be 98 mass % or more, and may also be 99 mass % or more.

The isocyanate composition may further contain α-methylstyrene, and the content thereof is preferably $2.0 \times 10^{-4}$ parts by mass or more and 1.0 part by mass or less. The above-described manufacturing method to which α-methylstyrene is added can thus be more easily performed.

Furthermore, the isocyanate composition may further contain benzyltoluene, and the content thereof is preferably $5.0 \times 10^{-4}$ parts by mass or more and 2.0 parts by mass or less with respect to 100 parts by mass of the isocyanate compound. The above-described manufacturing method to which benzyltoluene is added can thus be more easily performed.

<Manufacturing Method of Biuret Type Isocyanate Polymer>

According to the polyisocyanate composition of the present embodiment, in generation of an isocyanate polymer by a reaction of a polyisocyanate and a biuret-forming agent, there is an effect that the isocyanate polymer can be efficiently obtained by containing the compound represented by formula (1).

The biuret-forming agent is not particularly limited as long as it is a compound that results in forming a biuret bond, and examples thereof include water, monovalent tertiary alcohols, formic acid, hydrogen sulfide, organic primary monoamines, and organic primary diamines. Among them, water is preferable.

Surprisingly, the present inventors found that, by adding a predetermined amount of the compound represented by formula (1) to the reaction of a polyisocyanate and a biuret-forming agent (in particular, a reaction for producing a urea compound), the reaction rate and the manufacturing efficiency of the isocyanate polymer can be improved.

Although the mechanism for exhibiting these effects is not clear, the present inventors assume that the urethane bond (—NHCOO—) of the compound represented by formula (1) accelerates the reaction of a polyisocyanate and a biuret-forming agent. When the additive amount of the compound represented by formula (1) is $2.0 \times 10^{-4}$ parts by mass or more and 1.0 part by mass or less with respect to 100 parts by mass of the polyisocyanate, the above-described effect can be further improved.

From the viewpoint of further improving the reaction rate, the additive amount of the compound represented by formula (1) is preferably $3.0 \times 10^{-4}$ parts by mass or more, more preferably $5.0 \times 10^{-4}$ parts by mass or more, and further preferably $1.0 \times 10^{-3}$ parts by mass or more with respect to 100 parts by mass of the polyisocyanate.

Moreover, from the viewpoint of sufficiently suppressing the coloration of the composition containing the isocyanate polymer, the additive amount of the compound represented by formula (1) is preferably 0.5 parts by mass or less, more preferably 0.3 parts by mass or less, and further preferably 0.1 parts by mass or less with respect to 100 parts by mass of the polyisocyanate.

In the reaction of a polyisocyanate and a biuret-forming agent, only one kind of the compound represented by formula (1) may be added, or a plurality of kinds thereof may be added. In addition, when a plurality of kinds of the compound represented by formula (1) is added, the additive amount of the compound represented by formula (1) is the sum of the plurality of kinds thereof.

In the present embodiment, an unsaturated bond compound may be further added to the reaction of a polyisocyanate and a biuret-forming agent. The addition of the unsaturated bond compound exhibits an effect of accelerating a biuret-forming reaction (an adding reaction of an isocyanate to a urea bond), especially.

According to the polyisocyanate composition of the present embodiment, by adding the unsaturated bond compound, the biuret-forming reaction can be accelerated, the reaction time can be shortened, and the coloration of the composition containing the isocyanate polymer that is a manufactured article can be sufficiently suppressed.

Although the mechanism for exhibiting the above-described effects by the addition of the unsaturated bond compound is not clear, the present inventors assume that coordination of the unsaturated bond of the unsaturated bond compound to the urea bond increases a biuret-forming reaction rate.

From the viewpoint of sufficiently obtaining the effects by the addition of the unsaturated bond compound, the additive amount of the unsaturated bond compound is preferably $2.0 \times 10^{-4}$ parts by mass or more and 1.0 part by mass or less with respect to 100 parts by mass of the polyisocyanate.

Moreover, from the viewpoint of further accelerating the biuret-forming reaction, the additive amount of the unsaturated bond compound is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the polyisocyanate.

Furthermore, from the viewpoint of preventing the coloration, the additive amount of the unsaturated bond compound is more preferably 0.5 parts by mass or less, even more preferably 0.3 parts by mass or less, and further preferably 0.1 parts by mass or less with respect to 100 parts by mass of the polyisocyanate.

In the present embodiment, an inactive compound may be further added to the reaction of a polyisocyanate and a biuret-forming agent. By the addition of the inactive compound, solubility of the polyisocyanate in the reaction system is improved and the reaction efficiency is further improved. Furthermore, the addition of the inactive compound also exhibits an effect of making it easy to distill away the unreacted polyisocyanate after the reaction of a polyisocyanate and a biuret-forming agent. In this case, from the viewpoint of effectively obtaining the above-described effect, the additive amount of the inactive compound is preferably $2.0 \times 10^{-4}$ parts by mass or more, more preferably $2.0 \times 10^{-3}$ parts by mass or more, and further preferably $3.0 \times 10^{-2}$ parts by mass or more with respect to 100 parts by mass of the polyisocyanate.

Furthermore, in order to avoid incorporation of the inactive compound into the isocyanate polymer, the additive amount of the inactive compound is preferably 1.5 parts by mass or less, more preferably 1.3 parts by mass or less, and further preferably 1.0 part by mass or less with respect to 100 parts by mass of the polyisocyanate.

In the present embodiment, a urea compound is obtained by a urea-forming reaction of a polyisocyanate and a biuret-forming agent, and then, a biuret compound is obtained by a biuret-forming reaction of a polyisocyanate and a urea compound (an adding reaction of an isocyanate to a urea bond).

Regarding a proportion of the polyisocyanate to the biuret-forming agent subjected to the reaction, the molar number of the isocyanate group of the polyisocyanate is preferably 4 to 40 with respect to the molar number of the biuret-forming agent of 1. The lower limit is more preferably 5. Moreover, the upper limit is more preferably 30, and further preferably 20. When the molar number of the isocyanate group of the polyisocyanate is 4 or more, a low-viscosity polyisocyanate composition can be manufactured. Moreover, when the molar number of the isocyanate group of the polyisocyanate is less than 40, the sufficient production efficiency can be maintained.

The reaction temperature of the urea-forming reaction and the subsequent biuret-forming reaction is preferably 70° C. to 200° C. The lower limit is more preferably 80° C., and further preferably 90° C. Moreover, the upper limit is more preferably 180° C., and further preferably 170° C. When it is 70° C. or more, the sufficient reaction rate can be maintained, and when it is 200° C. or less, the coloration of the obtained composition containing the isocyanate polymer can be suppressed.

Furthermore, the reaction time is preferably 10 minutes to 24 hours, more preferably 15 minutes to 15 hours, and further preferably 20 minutes to 10 hours.

Although these reactions can be performed batch-wise, a continuous method is preferable in terms of productivity and the like. In particular, a continuous manufacturing method in which after a reaction of a diisocyanate and a biuret-forming agent, which is disclosed in JP 62-41496 B, is performed in a homogeneously stirred state, the reaction product is further introduced into a pipe reactor and the reaction is made to proceed in an extraction flow in the pipe reactor is preferably applied.

Moreover, a solvent can be used in the biuret-forming reaction. A polyisocyanate and a biuret-forming agent are dissolved and a homogeneous phase can be formed under reaction conditions by using a solvent. Generation of by-products such as polyurea can be suppressed by using a solvent. A solvent having low solubility of a biuret-forming agent such as water is not preferable because the additive amount thereof becomes such high, and it is not economical when separating and collecting the solvent after the completion of the reaction. The solvent has preferably solubility of a biuret-forming agent such as water of 0.5 mass % or more. Furthermore, considering collection and separation of the unreacted diisocyanate, the boiling point of the solvent is preferably lower than the boiling point of the raw material diisocyanate.

Specific examples of the solvent include ethylene glycol solvents, propylene glycol solvents, and alkyl phosphate solvents not having an active hydrogen group. Examples of the ethylene glycol solvents include ethylene glycol monomethyl ether acetate, ethylene glycol monoethyl ether acetate, ethylene glycol mono-n-propyl ether acetate, ethylene glycol monoisopropyl ether acetate, ethylene glycol mono-n-butyl ether acetate, ethylene glycol diacetate, ethylene glycol dimethyl ether, ethylene glycol diethyl ether, ethylene glycol di-n-propyl ether, ethylene glycol diisopropyl ether, ethylene glycol di-n-butyl ether, ethylene glycol methyl ethyl ether, ethylene glycol methyl isopropyl ether, ethylene glycol methyl-n-butyl ether, ethylene glycol ethyl-n-propyl ether, ethylene glycol ethyl isopropyl ether, ethylene glycol ethyl-n-butyl ether, ethylene glycol-n-propyl-n-butyl ether, ethylene glycol isopropyl-n-butyl ether, diethylene glycol monomethyl ether acetate, diethylene glycol monoethyl ether acetate, diethylene glycol mono-n-propyl ether acetate, diethylene glycol monoisopropyl ether acetate, diethylene glycol mono-n-butyl ether acetate, diethylene glycol diacetate, diethylene glycol dimethyl ether, diethylene glycol diethyl ether, diethylene glycol di-n-propyl ether, diethylene glycol diisopropyl ether, diethylene glycol di-n-butyl ether, diethylene glycol methyl ethyl ether, diethylene glycol methyl isopropyl ether, diethylene glycol methyl-n-propyl ether, diethylene glycol methyl-n-butyl ether, diethylene glycol ethyl isopropyl ether, diethylene glycol ethyl-n-propyl ether, diethylene glycol ethyl-n-butyl ether, diethylene glycol-n-propyl-n-butyl ether, and diethylene glycol isopropyl-n-butyl ether. Moreover, examples of the propylene glycol solvents include propylene glycol monomethyl ether acetate, propylene glycol monoethyl ether acetate, propylene glycol mono-n-propyl ether acetate, propylene glycol monoisopropyl ether acetate, propylene glycol mono-n-butyl ether acetate, propylene glycol diacetate, propylene glycol dimethyl ether, propylene glycol diethyl ether, propylene glycol di-n-propyl ether, propylene glycol diisopropyl ether, propylene glycol di-n-butyl ether, propylene glycol methyl ethyl ether, propylene glycol methyl isopropyl ether, propylene glycol methyl-n-butyl ether, propylene glycol ethyl-n-propyl ether, propylene glycol ethyl isopropyl ether, propylene glycol ethyl-n-butyl ether, propylene glycol-n-propyl-n-butyl ether, propylene glycol isopropyl-n-butyl ether, dipropylene glycol monomethyl ether acetate, dipropylene glycol monoethyl ether acetate, dipropylene glycol mono-n-propyl ether acetate, dipropylene glycol monoisopropyl ether acetate, dipropylene glycol mono-n-butyl ether acetate, dipropylene glycol diacetate, dipropylene glycol dimethyl ether, dipropylene glycol diethyl ether, dipropylene glycol di-n-propyl ether, dipropylene glycol diisopropyl ether, dipropylene glycol di-n-butyl ether, dipropylene glycol methyl ethyl ether, dipropylene glycol methyl isopropyl ether, dipropylene glycol methyl-n-propyl ether, dipropylene glycol methyl-n-butyl ether, dipropylene glycol ethyl isopropyl ether, dipropylene glycol ethyl-n-propyl ether, dipropylene glycol ethyl-n-butyl ether, dipropylene glycol-n-propyl-n-butyl ether, and dipropylene glycol isopropyl-n-butyl ether.

Examples of preferred ethylene glycol solvents include ethylene glycol monomethyl ether acetate, ethylene glycol monoethyl ether acetate, ethylene glycol diacetate, and diethylene glycol dimethyl ether, and examples of preferred propylene glycol solvents include propylene glycol monomethyl ether acetate, propylene glycol monoethyl ether acetate, propylene glycol diacetate, and dipropylene glycol dimethyl ether.

Furthermore, examples of the alkyl phosphate solvents include trimethyl phosphate, triethyl phosphate, tripropyl phosphate, and tributyl phosphate, and trimethyl phosphate or triethyl phosphate is preferable. These may be used alone or two or more kinds thereof may be used in combination. The preferred solvent-blending mass ratio of ethylene glycol solvent/phosphate solvent is 3/7 to 9/1, and the preferred amount used is 20 to 50 mass % with respect to the total mass of the diisocyanate and the solvent.

After the completion of the reaction, the unreacted polyisocyanate and the solvent can be separated from the composition containing the isocyanate polymer by treatment such as a thin-film distillation method and a solvent extraction method.

On the basis of the total mass of the composition containing the isocyanate polymer, the concentration of the polyisocyanate contained in the composition containing the isocyanate polymer is preferably controlled to be 2 mass % or less by performing the treatment. The upper limit of the polyisocyanate concentration is more preferably 1.5 mass % or less, even more preferably 1.0 mass % or less, further preferably 0.7 mass % or less, and even further preferably 0.5 mass % or less. By making the polyisocyanate concentration be the above-described upper limit or less, toxicity of the composition containing the isocyanate polymer can be further reduced, and safety can be increased.

The average value of the number of isocyanate groups in the composition containing the isocyanate polymer having the biuret bond obtained in the present embodiment is preferably 3.0 or more. Furthermore, it is more preferably 3.1 or more, and further preferably 3.2 or more. If the average value of the number of isocyanate groups in the isocyanate polymer is 3.0 or more, a cross-linkage property when being used as a curing agent for a coating material can be exhibited.

(III) Polyisocyanate Composition Containing Polyisocyanate and Inactive Compound.

A polyisocyanate composition of the present embodiment contains, on the basis of the total mass thereof, 97 mass % or more of a polyisocyanate, and 20 mass ppm or more and $2.0 \times 10^4$ mass ppm or less of an inactive compound (at least one compound selected from the group consisting of compound A to compound G).

In the polyisocyanate composition of the present embodiment, the content of the polyisocyanate is 97 mass % or more, and preferably 98 mass % or more. In addition, the content of the diisocyanate may be 99.5 mass % or less, or 99 mass % or less. The content of the inactive compound is preferably $2.0 \times 10^{-3}$ parts by mass or more and 2.0 parts by mass or less with respect to 100 parts by mass of the polyisocyanate.

The present inventors found that, when manufacturing an isocyanate polymer containing an isocyanurate structure (a structure represented by formula (3)), an iminooxadiazine dione structure (a structure represented by formula (5)), or a uretdione structure (a structure represented by formula (7))

using the polyisocyanate composition of the present embodiment, simultaneously proceeding isocyanurate-forming reaction, iminooxadiazine dione-forming reaction, and uretdione-forming reaction can be accelerated with a lower amount of the catalyst. Since the catalyst becomes the cause of increase in thermal yellowing and deterioration in weatherability of the composition containing the isocyanate polymer, the amount of the catalyst used in the above-described manufacturing method of an isocyanate polymer can be reduced, and therefore, a remarkable effect that thermal yellowing and weatherability of the obtained composition containing the isocyanate polymer are improved is exhibited. Although the mechanism for exhibiting the effect is not clear, it is assumed that this is because polarity in the reaction system is decreased by the presence of the above-described inactive compound and the catalyst is activated.

From the viewpoint of effectively obtaining the above-described effect, the amount of the inactive compound contained in the polyisocyanate composition of the present embodiment is preferably $2.0 \times 10^{-4}$ parts by mass or more, more preferably $2.0 \times 10^{-3}$ parts by mass or more, and further preferably $3.0 \times 10^{-2}$ parts by mass or more with respect to 100 parts by mass of the polyisocyanate. Moreover, the content of the inactive compound is preferably 2.0 parts by mass or less, more preferably 1.3 parts by mass or less, and further preferably 1.0 part by mass or less with respect to 100 parts by mass of the polyisocyanate. The content of the inactive compound of 2.0 parts by mass or less tends to be difficult to cause coloration.

The polyisocyanate composition of the present embodiment may contain the compound represented by formula (1). By performing a reaction such as the isocyanurate-forming reaction using the diisocyanate composition further containing the compound represented by formula (1), the reactivity of the reaction such as the isocyanurate-forming reaction is further improved, and the amount of the catalyst can be further reduced. Although the mechanism for exhibiting these effects is not clear, the present inventors assume that coordination of the urethane group (—NHCOO—) of the compound represented by formula (1) to the catalyst stabilizes the catalyst.

The urethane group (—NHCOO—) may become the cause of thermal yellowing and coloration when remaining in the isocyanate polymer. However, since the urethane group of the compound represented by formula (1) has the low thermal decomposition temperature, the urethane group is often thermally decomposed by heating when distillation purifying the unreacted polyisocyanate after the reaction such as the isocyanurate-forming reaction and is difficult to remain in the composition containing the isocyanate polymer as an impurity. Therefore, there is an advantage that the compound represented by formula (1) is difficult to become the cause of thermal yellowing and deterioration in weatherability of the obtained composition containing the isocyanate polymer.

The amount of the compound represented by formula (1) contained in the polyisocyanate composition of the present embodiment is preferably $2.0 \times 10^{-4}$ parts by mass or more and 1.0 part by mass or less with respect to 100 parts by mass of the polyisocyanate. By making the content of the compound represented by formula (1) be within the above-described range, the reactivity in the reaction such as the isocyanurate-forming reaction is further improved, and the amount of the catalyst can be further reduced.

From the viewpoint of capable of further reducing the amount of the catalyst, the content of the compound represented by formula (1) is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the polyisocyanate. Moreover, from the viewpoint of preventing the coloration, the content of the compound represented by formula (1) is more preferably 0.5 parts by mass or less, even more preferably 0.3 parts by mass or less, and further preferably 0.1 parts by mass or less with respect to 100 parts by mass of the polyisocyanate.

The polyisocyanate composition of the present embodiment may further contain an unsaturated bond compound. The reactivity in the reaction such as the isocyanurate-forming reaction of the polyisocyanate composition of the present embodiment is further improved, and the amount of the catalyst can be further reduced by further containing the unsaturated bond compound. Although the mechanism for exhibiting these effects is not clear, the present inventors assume that coordination of the unsaturated bond of the unsaturated bond compound to the catalyst increases catalyst activity.

In order to obtain more improvement effect of the catalyst activity, the amount of the unsaturated bond compound subjected to the reaction such as the isocyanurate-forming reaction is preferably increased. In the present embodiment, the amount of the unsaturated bond compound added to the reaction system of the isocyanurate-forming reaction is preferably $2.0 \times 10^{-4}$ parts by mass or more and 1.0 part by mass or less with respect to 100 parts by mass of the polyisocyanate. When the unsaturated bond compound is contained within the range, the reactivity of the reaction such as the isocyanurate-forming reaction is further improved, and the amount of the catalyst can be further reduced.

From the viewpoint of capable of further reducing the amount of the catalyst, the amount of the unsaturated bond compound contained in the polyisocyanate composition is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the polyisocyanate.

Moreover, from the viewpoint of preventing the coloration due to the excessive unsaturated bond compound, the amount of the unsaturated bond compound added to the reaction system of the reaction such as the isocyanurate-forming reaction is more preferably 0.5 parts by mass or less, even more preferably 0.3 parts by mass or less, and further preferably 0.1 parts by mass or less with respect to 100 parts by mass of the isocyanate.

A manufacturing method of an isocyanate polymer using the polyisocyanate composition of the present embodiment will be described. In addition, an isocyanurate-forming reaction will be mainly described, but an iminooxadiazine dione-forming reaction and a uretdione-forming reaction may occur depending on a catalyst or reaction conditions used, as described below.

<Manufacturing Method of Isocyanurate Type Isocyanate Polymer>

The isocyanurate-forming reaction is preferably performed in the presence of an isocyanurate-forming catalyst.

For example, as a specific isocyanurate-forming catalyst, generally, one having basicity is preferable, and examples thereof include the following compounds.

(i) hydroxides or organic acid salts (for example, salts such as acetate, butyrate, and decanoate) of tetraalkylammoniums (tetramethylammonium, tetraethylammonium and the like), (ii) hydroxides or organic acid salts (for example, salts such as acetate, butyrate, and decanoate) of trialkyl hydroxyalkylammoniums (trimethyl hydroxypropylammonium, trimethyl hydroxyethylammonium, triethyl hydroxypropylammonium, triethyl hydroxyethylammonium and the like),
(iii) metal salts (for example, tin salt, zinc salt, lead salt, sodium salt, potassium salt and the like) of alkylcarboxylic acids such as acetic acid, capric acid, octylic acid, and myristic acid,
(iv) metal alkoxides such as sodium alkoxide and potassium alkoxide,
(v) aminosilyl group-containing compounds (for example, hexamethyldisilazane and the like),
(vi) phosphorous compounds such as tributylphosphine,
(vii) fluorine compounds or hydrogen polyfluoride compounds (for example, tetraalkylammonium fluorides and the like such as tetramethylammonium fluoride hydrate and tetraethylammonium fluoride),
(viii) compounds formed from compounds containing a structure represented by formula (28) or (29) (for example, 3,3,3-trifluoropropanoic acid; 3,3,4,4,4-pentafluorobutanoic acid; 3,3,4,4,5,5,5-heptafluoropentanoic acid; 3,3-difluoroprop-2-enoic acid or the like), and quaternary ammonium ion or quaternary phosphonium ion.

$$R^{19}=CR'-C(=O)O- \qquad (28)$$

$$R^{20}-CR'_2-C(=O)O- \qquad (29)$$

(In the formulas, $R^{19}$ and $R^{20}$ each independently represents a perfluoroalkyl group having 1 to 30 carbon atoms, and R' each independently represents one selected from the group consisting of a hydrogen atom, an alkyl group having 1 to 20 carbon atoms, and an aromatic group, and these may contain a hetero atom.)

In addition, $R^{19}$ and $R^{20}$ may each independently be a linear-chain, branched, or cyclic saturated perfluoroalkyl group or unsaturated perfluoroalkyl group.

Among them, from the viewpoint of the catalyst efficiency and the selectivity of the isocyanurate-forming reaction, the above-described catalyst (i) or (ii) is preferable.

Moreover, in the case of forming such that the proportion of the uretdione structure (a structure represented by formula (7)) is high, the use of the above-described catalyst (vi) is preferable.

Furthermore, in the case of desiring to form such that the proportion of the iminooxadiazine dione structure (a structure represented by formula (5)) is high, the use of the catalyst (vii) or the catalyst (viii) is preferable.

The amount of the isocyanurate-forming catalyst added to the reaction system of the isocyanurate-forming reaction can be appropriately adjusted depending on the kind of the catalyst to be used, the concentration of other constituents in the reaction system and the like, and it can be $1.0 \times 10^{-4}$ parts by mass or more and 1.0 part by mass or less with respect to 100 parts by mass of the isocyanate, for example. From the viewpoint of the suppression of coloration or discoloration of a product, and a reaction control, the upper limit of the amount of the isocyanurate-forming catalyst used is preferably $5.0 \times 10^{-1}$ parts by mass or less, more preferably $1.0 \times 10^{-1}$ parts by mass or less, and further preferably $2.0 \times 10^{-2}$ parts by mass or less. From the viewpoint of reactivity, the lower limit of the amount of the isocyanurate-forming catalyst used is more preferably $1.0 \times 10^{-3}$ parts by mass or more, and further preferably $2.0 \times 10^{-3}$ parts by mass or more.

The isocyanurate-forming catalyst described above can become the allophanate-forming catalyst at the same time. Thus, by adding a hydroxy group-containing compound before or during the isocyanurate-forming reaction, the isocyanurate-forming reaction and the allophanate-forming reaction can be made to simultaneously proceed.

As the hydroxy group-containing compound in this case, a compound formed from only carbon, hydrogen, and oxygen and having one or two hydroxy groups in one molecule is preferable. A compound having only one hydroxy group is further preferable. Specific examples of the compound having one hydroxy group include methyl alcohol, ethyl alcohol, propyl alcohol, butyl alcohol, pentyl alcohol, hexyl alcohol, heptyl alcohol, octyl alcohol, and nonyl alcohol, examples of the compound having two hydroxy groups include ethylene glycol, 1,3-butanediol, 1,4-butanediol, neopentyl glycol, and 2-ethyl hexanediol, and two or more kinds thereof may be used in combination.

Although the reaction temperature of the isocyanurate-forming reaction is not particularly limited, 0° C. to 200° C. is preferable. The reaction temperature of less than 0° C. is not practical because the reaction rate is low, and when the reaction is performed at high temperature above 200° C., side reactions, extreme coloration of a product and the like tend to easily occur. Among them, from the viewpoint of the reaction rate, the lower limit of the reaction temperature is more preferably 40° C., further preferably 50° C., and most preferably 60° C. From the viewpoint of coloration of a product itself and the obtained polyisocyanate, the upper limit of the reaction temperature is more preferably 150° C., and is 40° C. to 150° C. From the viewpoint of coloration of a product, the upper limit of the polymerization reaction temperature is more preferably 150° C. or less, further preferably 120° C., and most preferably 110° C.

The reaction time of the isocyanurate-forming reaction is not particularly limited, and for example, the isocyanurate-forming reaction can be performed within a range of 10 seconds to 24 hours.

Examples of a confirmation method of the terminal point of the isocyanurate-forming reaction include a method for measuring the content rate of the isocyanate group in the reaction mixture (NCO %), a method for measuring a refractive index, and a method by gel permeation chromatography measurement of the reaction mixture. In addition, the measurement method of the content rate of the isocyanate group in the reaction mixture (NCO %) will be described below.

When the isocyanurate-forming reaction proceeds too much, the viscosity of the product is increased, the content proportion of the isocyanurate compound is increased, and a manufactured article having intended physical properties may not be obtained, and therefore, the conversion rate of the reaction (proportion of reacted polyisocyanate to initial amount of polyisocyanate) is preferably limited to 50% or less (more preferably 40% or less, and further preferably 25% or less). Moreover, from the viewpoint of sufficiently obtaining the yield of the isocyanurate compound, the conversion rate of the reaction is preferably 5% or more, more preferably 10% or more, and more preferably 15% or more.

In the present embodiment, when the isocyanurate-forming reaction reaches the intended conversion rate, a catalyst-terminating agent is added to deactivate the isocyanurate-forming catalyst so that the isocyanurate-forming reaction can be terminated. If the catalyst-terminating agent is not added, the isocyanurate-forming reaction further proceeds in the distillation purification of the isocyanate polymer, and the viscosity of the manufactured article may become high and a gel component may be generated. In order to prevent the isocyanurate-forming reaction from proceeding in the distillation purification, it is preferable that the isocyanurate-forming catalyst be deactivated by adding the catalyst-terminating agent. In the present embodiment, since the amount of the catalyst used can be sufficiently suppressed by the addition of the inactive compound (at least one compound selected from the group consisting of compound A to compound G), thermal yellowing and weatherability can be sufficiently improved even when the catalyst-terminating agent is added. As the isocyanurate-forming catalyst, the compound B is preferable.

As the catalyst-terminating agent, for example, sulfuric acid, phosphoric acid, acidic phosphate esters, hydrochloric acid, sulfonic acid compounds and the like can be used. In the case where a reaction product of the catalyst-terminating agent and the catalyst is precipitated as a solid, the reaction product is preferably separated by a method such as filtration using a filter or Celite.

Although the isocyanurate-forming reaction can be performed in the presence or absence of a solvent, from the viewpoint of easiness of controlling the reaction and easiness of handling, the isocyanurate-forming reaction is preferably performed in the presence of a solvent.

As a solvent used in the isocyanurate-forming reaction, a solvent that is inactive with respect to a polyisocyanate to be used and dissolves a raw material isocyanate and an isocyanurate compound to be generated is selected. Specifically, as a solvent, acetate esters such as ethyl acetate, butyl acetate, and amyl acetate; and aromatic hydrocarbons such as benzene, toluene, xylene, and monochlorobenzene can be used alone or in combination.

Moreover, in the case of performing the isocyanurate-forming reaction in the absence of a solvent, by limiting the conversion rate to 50% or less, the unreacted polyisocyanate functions as a solvent and can dissolve the isocyanurate compound to be generated. From the viewpoint, the conversion rate of the isocyanurate-forming reaction in the absence of a solvent is preferably 5% to 50%, and more preferably 10% to 40%.

After the completion of the reaction of the isocyanurate-forming reaction, for example, by removing the unreacted polyisocyanate and the solvent from the reaction system, the isocyanurate compound can be collected. A removal method is not particularly limited, and the unreacted polyisocyanate and the solvent can be removed by distillation purification, for example. In addition, the removal is desirably performed at low temperature, and is preferably performed using a device that has a large evaporation surface with respect to liquid and good evaporation efficiency, such as a falling thin-film evaporator, a thin-film evaporation device, a molecular distillation device.

The concentration of the polyisocyanate contained in the composition containing the isocyanate polymer is preferably controlled to be 1 mass % or less by performing the removal. The upper limit of the diisocyanate concentration is more preferably 0.7 mass % or less, further preferably 0.5 mass % or less, and more further preferably 0.3 mass % or less. By making the polyisocyanate concentration be the above-described upper limit or less, toxicity of the composition containing the isocyanate polymer can be further reduced, and safety can be increased.

In the composition containing the isocyanate polymer including the isocyanurate structure obtained by the method of the present embodiment, the average value of the number of isocyanate groups is preferably 2.3 or more. Furthermore, it is more preferably 2.5 or more, even more preferably 2.7 or more, further preferably 3.0 or more, and more further preferably 3.2 or more.

If the average value of the number of isocyanate groups is 2.3 or more, a cross-linkage property when being used as a curing agent for a coating material can be exhibited.

When performing the isocyanurate-forming reaction, the polyisocyanate and at least one compound selected from the group consisting of the above-described compound A to compound G may each independently be subjected to the reaction system, or the polyisocyanate composition containing the polyisocyanate and at least one compound selected from the group consisting of the above-described compound A to compound G is prepared in advance, and then, the polyisocyanate composition may be subjected to the reaction system.

In the present embodiment, the polyisocyanate composition subjected to the isocyanurate-forming reaction or the like contains, for example, the polyisocyanate and, with respect to 100 parts by mass of the polyisocyanate, $5.0 \times 10^{-4}$ parts by mass or more and 2.0 parts by mass or less of at least one compound selected from the group consisting of the above-described compound A to compound G. The isocyanurate-forming reaction or the like can be more easily performed by preparing the polyisocyanate composition like this.

On the basis of the total mass of the polyisocyanate composition, the content of the polyisocyanate in the polyisocyanate composition may be 98 mass % or more, and may also be 99 mass % or more.

Moreover, the polyisocyanate composition of the present embodiment may further contain a compound represented by formula (1). The content of the compound represented by formula (1) is preferably $2.0 \times 10^{-4}$ parts by mass or more and 1.0 part by mass or less with respect to 100 parts by mass of the polyisocyanate.

Furthermore, the polyisocyanate composition of the present embodiment may further contain an unsaturated bond compound. The content of the unsaturated bond compound is preferably $2.0 \times 10^{-4}$ parts by mass or more and 1.0 part by mass or less with respect to 100 parts by mass of the polyisocyanate. The isocyanurate-forming reaction to which the unsaturated bond compound is added can thus be easily performed.

<Isocyanate Polymer>

The polyisocyanate composition of the present embodiment is suitable for manufacturing an isocyanate polymer obtained by polymerizing a polyisocyanate. In the case where the polyisocyanate is a diisocyanate, the isocyanate polymer has a unit represented by formula (2), and has at least one or more units among units represented by formulas (3) to (9). In addition, a nitrogen atom constituting the isocyanate polymer is bonded to a carbon atom.

[Chemical Formula 32]

$$O=C=N-R^3-\qquad(2)$$

[Chemical Formula 33]

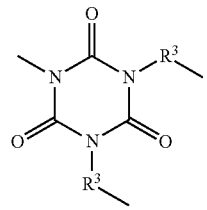

(3)

-continued

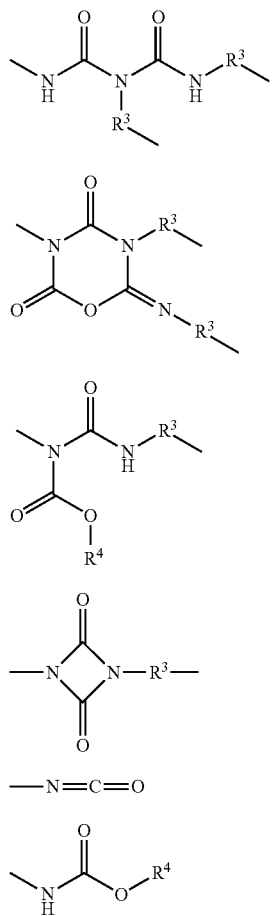

(In the formulas, $R^3$ represents a divalent hydrocarbon group, $R^4$ represents a monovalent organic group, and multiple $R^3$s and $R^4$s may be the same or different.)

In formulas (3) to (7), $R^3$ is a group derived from a polyisocyanate. In the case where the polyisocyanate is the compound represented by formula (10) and a diisocyanate, in which c is 2, $R^3$ is the same as the definition of $R^1$ in formula (1).

In formula (6) or formula (9), $R^4$ depends on a compound used when manufacturing the isocyanate polymer, and for example, in the case of using an alcohol, $R^4$ is a residue obtained by removing a hydroxy group (OH group) from the above-described alcohol.

Hereinafter, the present embodiment will be described more specifically.

(Manufacturing Method of Isocyanurate Compound)

A manufacturing method of an isocyanurate compound according to the present embodiment is characterized by including a step of obtaining an isocyanurate compound having an isocyanurate structure by an isocyanurate-forming reaction of an isocyanate compound having an isocyanate group, and performing the isocyanurate-forming reaction in a reaction system to which, with respect to 100 parts by mass of the isocyanate compound, $2.0 \times 10^{-3}$ parts by mass or more and 2.0 parts by mass or less of benzyltoluene is added.

Generally, coloration often occurs in the obtained isocyanurate compound if an aromatic compound is mixed in the raw material, but surprisingly, the present inventors found that the isocyanurate-forming reaction can be performed with a lower amount of the catalyst by offering a specific amount of benzyltoluene to the isocyanurate-forming reaction. As described above, since the catalyst used in the manufacture of the isocyanurate compound becomes the cause of increase in thermal yellowing and deterioration in weatherability of the isocyanurate compound, by reduction in the amount of the catalyst used, a remarkable effect that thermal yellowing and weatherability of the isocyanurate compound are improved is exhibited. Although the mechanism for exhibiting the effect is not clear, it is assumed that this is because polarity in the reaction system is decreased by the presence of benzyltoluene and the catalyst is activated.

Benzyltoluene has three kinds of isomers represented by formulas (3-1), (3-2), and (3-3), and in the present embodiment, any of these isomers may be used, or a mixture of these isomers may be used as benzyltoluene. In addition, the content of benzyltoluene is the sum of the content of the isomers.

[Chemical Formula 39]

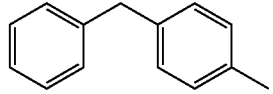
(3-1)

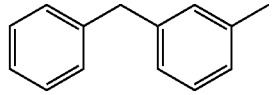
(3-2)

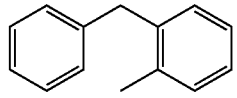
(3-3)

From the viewpoint of effectively obtaining the above-described effect, the amount of benzyltoluene added to the reaction system of the isocyanurate-forming reaction is preferably $5.0 \times 10^{-4}$ parts by mass or more, more preferably $2.0 \times 10^{-3}$ parts by mass or more, and further preferably $3.0 \times 10^{-2}$ parts by mass or more with respect to 100 parts by mass of the isocyanate compound.

In addition, the addition of too much benzyltoluene may become the cause of coloration, and therefore, the amount of benzyltoluene added to the reaction system of the isocyanurate-forming reaction is preferably 2.0 parts by mass or less, more preferably 1.3 parts by mass or less, and further preferably 1.0 part by mass or less with respect to 100 parts by mass of the isocyanate compound.

In addition, commercial benzyltoluene or the like may contain compounds represented by formulas (4-1) to (4-8), and in the present embodiment, benzyltoluene containing these compounds may be directly used or benzyltoluene purified by distillation purification or the like may be used. In addition, the content of these compounds in the reaction system of the isocyanurate-forming reaction is preferably 10 parts by mass or less with respect to 100 parts by mass of benzyltoluene.

[Chemical Formula 35]

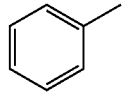
(4-1)

-continued (4-2) 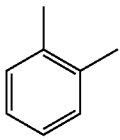

(4-3) 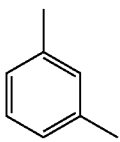

(4-4) 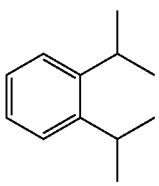

(4-5) 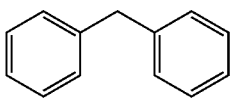

(4-6) 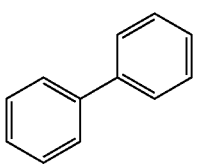

(4-7) 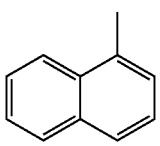

(4-8) 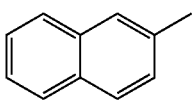

The isocyanate compound in the present embodiment is not particularly limited and can be appropriately varied depending on an intended isocyanurate compound. For example, from the viewpoint of obtaining an isocyanurate compound capable of being suitably used for applications requiring weatherability, an aliphatic diisocyanate and/or an alicyclic diisocyanate are preferable. In addition, for the purpose of being applied to fields not requiring weatherability and the like, an aromatic diisocyanate can also be selected.

From the viewpoint of remarkably exhibiting the effect of the present invention, the isocyanate compound may be an isocyanate compound having two or more isocyanate groups, may also be an isocyanate compound having two to four isocyanate groups, or may also be an isocyanate compound having two isocyanate groups. Furthermore, the isocyanate compound may be a compound represented by formula (10).

[Chemical Formula 36]

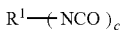

(10)

In the formula, c represents an integer of 2 to 4, and $R^1$ represents a c-valent organic group.

Examples of $R^1$ include an aliphatic hydrocarbon group, an alicyclic hydrocarbon group (a hydrocarbon group having an alicyclic group), and an aromatic hydrocarbon group (a hydrocarbon group having an aromatic ring).

Examples of the aliphatic hydrocarbon group include a group having 1 to 40 carbon atoms (preferably 4 to 30 carbon atoms). Moreover, specific examples of the aliphatic hydrocarbon group include groups obtained by removing c hydrogen atoms from aliphatic hydrocarbons such as butane (each isomer), pentane (each isomer), hexane (each isomer), heptane (each isomer), octane (each isomer), decane (each isomer), dodecane (each isomer), and octadecane (each isomer).

Examples of the alicyclic hydrocarbon group include a group having 6 to 40 carbon atoms (preferably 8 to 30 carbon atoms). Moreover, specific examples of the alicyclic hydrocarbon group include groups obtained by removing c hydrogen atoms from alicyclic hydrocarbons such as cyclohexane, dimethylcyclohexane (each isomer), tetramethylcyclohexane (each isomer), dicyclohexylmethane, cycloheptane, and cyclooctane.

Examples of the aromatic hydrocarbon group include a group having 6 to 40 carbon atoms (preferably 8 to 30 carbon atoms). Moreover, specific examples of the aromatic hydrocarbon group include groups obtained by removing c hydrogen atoms from aromatic hydrocarbons such as benzene, toluene, xylene (each isomer), naphthalene, diphenylmethane, and biphenyl.

Furthermore, $R^1$ may be a group obtained by substituting the above-described group with a substituent group, such as a halogen atom, an alkoxy group, and an alkoxycarbonyl group.

Specific examples of the isocyanate compound include tetramethylene diisocyanate, pentamethylene diisocyanate, hexamethylene diisocyanate, 2,2,4-trimethyl-1,6-diisocyanatohexane, lysine diisocyanate, isophorone diisocyanate, 1,3-bis(isocyanatomethyl)-cyclohexane, 4,4'-dicyclohexylmethane diisocyanate, 4,4'-diphenylmethane diisocyanate, toluene diisocyanate (each isomer), and lysine triisocyanate. Among them, from the viewpoint of being suitable for applications requiring weatherability and thermal yellowing resistance and being industrially easily-available, hexamethylene diisocyanate and isophorone diisocyanate are preferable. Moreover, the isocyanate compound may be used alone or a plurality of kinds thereof may be used in combination.

In the present embodiment, the isocyanurate-forming reaction can also be performed in the reaction system to which a compound in which a urethane bond is formed by the reaction of a part or all of the isocyanate groups of the isocyanate compound with phenol is further added. That is, when the isocyanate compound is the compound represented by formula (10), a compound represented by formula (1) can be further subjected to the isocyanurate-forming reaction.

[Chemical Formula 37]

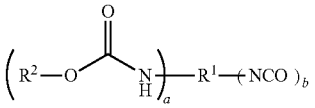

(1)

In the formula, $R^1$ is synonymous with $R^1$ in formula (10), a represents an integer of 1 to 4, b represents an integer of 0 to 3, and the sum of a and b is the same value as c in formula (10) (a+b=c).

By offering the compound represented by formula (10) to the isocyanurate-forming reaction in addition to the above-described benzyltoluene, the reactivity of the isocyanurate-forming reaction is further improved, and the amount of the catalyst can be further reduced. Although the mechanism for exhibiting these effects is not clear, the present inventors assume that coordination of the urethane group (—NHCOO—) of the compound represented by formula (1) to the catalyst stabilizes the catalyst.

Moreover, although the urethane group (—NHCOO—) may become the cause of thermal yellowing and coloration when remaining in the isocyanurate compound, the urethane group of the compound represented by formula (1) has the low thermal decomposition temperature, and thus, the urethane group is thermally decomposed by heating when distillation separating the unreacted isocyanurate compound after the isocyanurate-forming reaction. Since thermal decomposition products of the compound represented by formula (1) are an isocyanurate compound and phenol and since these are both easily distillation separated from the isocyanurate compound, an impurity derived from the compound represented by formula (1) is difficult to remain in the isocyanurate compound. Therefore, there is an advantage that the compound represented by formula (1) is difficult to become the cause of thermal yellowing and deterioration in weatherability of the isocyanurate compound.

The amount of the compound represented by formula (1) subjected to the isocyanurate-forming reaction is preferably increased so as to obtain more effect of catalyst stabilization, whereas an excess of the amount of the compound represented by formula (1) may become the cause of coloration. Therefore, in the present embodiment, the amount of the compound represented by formula (1) added to the reaction system of the isocyanurate-forming reaction is preferably $2.0 \times 10^{-4}$ parts by mass or more and 1.0 part by mass or less with respect to 100 parts by mass of the isocyanate compound. By offering the compound represented by formula (1) within the range, the reactivity of the isocyanurate-forming reaction is further improved, and the amount of the catalyst can be further reduced.

From the viewpoint of capable of further reducing the amount of the catalyst, the amount of the compound represented by formula (1) added to the reaction system of the isocyanurate-forming reaction is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the isocyanate compound.

Moreover, from the viewpoint of preventing the coloration, the amount of the compound represented by formula (1) added to the reaction system of the isocyanurate-forming reaction is more preferably 0.5 parts by mass or less, even more preferably 0.3 parts by mass or less, and further preferably 0.1 parts by mass or less with respect to 100 parts by mass of the isocyanate compound.

In the reaction system of the isocyanurate-forming reaction, only one kind of the compound represented by formula (1) may be added, or a plurality of kinds thereof may be added. In addition, when a plurality of kinds of the compound represented by formula (1) is added, the additive amount of the compound represented by formula (1) is the sum of the plurality of kinds thereof.

When the isocyanate compound is a compound having two isocyanate groups (that is, when c in formula (10) is 2, and $R^1$ is a divalent organic group), examples of the compound represented by formula (1) include a compound represented by formula (1-3) and a compound represented by formula (1-4). In addition, in the formulas, $R^1$ represents a divalent organic group that is the same as $R^1$ in formula (1).

[Chemical Formula 38]

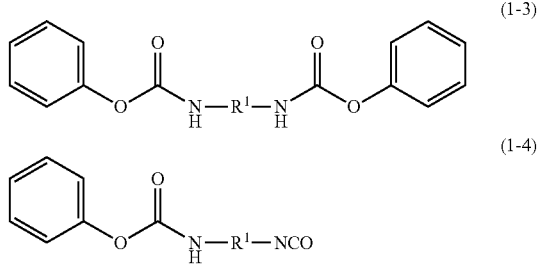

In the present embodiment, the isocyanurate-forming reaction can also be performed in the reaction system to which α-methylstyrene is further added. By offering α-methylstyrene to the isocyanurate-forming reaction in addition to the above-described benzyltoluene, the reactivity of the isocyanurate-forming reaction is further improved, and the amount of the catalyst can be further reduced. Although the mechanism for exhibiting these effects is not clear, the present inventors assume that coordination of the unsaturated bond of α-methylstyrene to the catalyst increases a catalytic activity.

The amount of α-methylstyrene subjected to the isocyanurate-forming reaction is preferably increased so as to obtain more improvement effect of the catalyst activity, whereas an excess of the amount of α-methylstyrene may become the cause of coloration. Therefore, in the present embodiment, the amount of α-methylstyrene added to the reaction system of the isocyanurate-forming reaction is preferably $2.0 \times 10^{-4}$ parts by mass or more and 1.0 part by mass or less with respect to 100 parts by mass of the isocyanate compound. By adding α-methylstyrene within the range, the reactivity of the isocyanurate-forming reaction is further improved, and the amount of the catalyst can be further reduced.

From the viewpoint of capable of further reducing the amount of the catalyst, the amount of α-methylstyrene added to the reaction system of the isocyanurate-forming reaction is more preferably $3.0 \times 10^{-4}$ parts by mass or more, even more preferably $5.0 \times 10^{-4}$ parts by mass or more, and further preferably $1.0 \times 10^{-3}$ parts by mass or more with respect to 100 parts by mass of the isocyanate compound.

Moreover, from the viewpoint of preventing the coloration, the amount of α-methylstyrene added to the reaction system of the isocyanurate-forming reaction is more preferably 0.5 parts by mass or less, even more preferably 0.3 parts by mass or less, and further preferably 0.1 parts by mass or less with respect to 100 parts by mass of the isocyanate compound.

Hereinafter, the isocyanurate-forming reaction will be described in detail.

The isocyanurate-forming reaction is preferably performed in the presence of a catalyst (isocyanurate-forming catalyst). Examples of the isocyanurate-forming catalyst include hydroxides or organic weak acid salts of tetraalkylammoniums such as tetramethylammonium, tetraethylammonium, and tetrabutylammonium; hydroxides or organic weak acid salts of trialkyl hydroxyalkylammoniums such as trimethyl hydroxypropylammonium, trimethyl hydroxyethylammonium, triethyl hydroxypropylammonium, and triethyl hydroxyethylammonium; alkali metal salts of alkylcarboxylic acids such as acetic acid, caproic acid, octylic acid, and myristic acid; metal salts of tin, zinc, lead or the like of alkylcarboxylic acids such as acetic acid, caproic acid, octylic acid, and myristic acid; and aminosilyl group-containing compounds such as hexamethyldisilazane.

The amount of the isocyanurate-forming catalyst added to the reaction system of the isocyanurate-forming reaction can be appropriately adjusted depending on the kind of the catalyst to be used, the concentration of other constituents in the reaction system and the like, and it can be $1.0 \times 10^{-4}$ parts by mass or more and $1.0 \times 10^{-2}$ parts by mass or less with respect to 100 parts by mass of the isocyanate compound, for example.

The reaction temperature of the isocyanurate-forming reaction is preferably 0° C. to 200° C., and more preferably 50 to 120° C. The reaction temperature of less than 0° C. is not practical because the reaction rate is low, and when the reaction is performed at high temperature above 200° C., side reactions, extreme coloration of a product and the like tend to easily occur.

The reaction time of the isocyanurate-forming reaction is not particularly limited, and for example, the isocyanurate-forming reaction can be performed within a range of 10 seconds to 24 hours. In addition, a reaction liquid is sampled, and for example, the reaction may be terminated after confirming by infrared absorption spectrum that the isocyanurate structure is contained, or the reaction may be terminated after confirming by gel permeation chromatography that the reaction liquid reaches an intended weight average molecular weight.

When the isocyanurate-forming reaction proceeds too much, the viscosity of the product is increased, the content proportion of the isocyanurate compound is increased, and a manufactured article having intended physical properties may not be obtained, and therefore, the conversion rate of the reaction (proportion of reacted isocyanate compound to initial amount of isocyanate compound) is preferably limited to 50% or less (more preferably 40% or less, and further preferably 25% or less). Moreover, from the viewpoint of sufficiently obtaining the yield of the isocyanurate compound, the conversion rate of the reaction is preferably 5% or more, more preferably 10% or more, and more preferably 15% or more.

In the present embodiment, when the isocyanurate-forming reaction reaches the intended conversion rate, a catalyst-terminating agent is added to deactivate the catalyst so that the isocyanurate-forming reaction can be terminated. Although not adding the catalyst-terminating agent that can become the cause of thermal yellowing is one of choices, the isocyanurate-forming reaction proceeds in the distillation separation of the isocyanate compound described below, and the viscosity of the manufactured article may become high and a gel component may be generated, and therefore, it is preferable that the catalyst-terminating agent be added so as to prevent this. In the present embodiment, since the amount of the catalyst used can be sufficiently suppressed by the addition of benzyltoluene, thermal yellowing and weatherability can be sufficiently improved even when the catalyst-terminating agent is added.

As the catalyst-terminating agent, for example, sulfuric acid, phosphoric acid, and phosphate esters and the like can be used. In the case where a reaction product of the catalyst-terminating agent and the catalyst is precipitated as a solid, the reaction product is preferably separated by a method such as filtration using a filter or Celite.

Although the isocyanurate-forming reaction can be performed in the presence or absence of a solvent, from the viewpoint of easiness of controlling the reaction and easiness of handling, the isocyanurate-forming reaction is preferably performed in the presence of a solvent.

As a solvent used in the isocyanurate-forming reaction, a solvent that is inactive with respect to an isocyanate compound to be used and dissolves a raw material isocyanate compound and an isocyanurate compound to be generated is selected. Specifically, as a solvent, acetate esters such as ethyl acetate, butyl acetate, and amyl acetate; and aromatic hydrocarbons such as benzene, toluene, xylene, and monochlorobenzene can be used alone or in combination.

Moreover, in the case of performing the isocyanurate-forming reaction in the absence of a solvent, by limiting the conversion rate to 50% or less, the unreacted isocyanate compound functions as a solvent and can dissolve the isocyanurate compound to be generated. From the viewpoint, the conversion rate of the isocyanurate-forming reaction in the absence of a solvent is preferably 5% to 50%, and more preferably 10% to 40%.

After the completion of the reaction of the isocyanurate-forming reaction, for example, by removing the unreacted isocyanate compound and the solvent from the reaction system, the isocyanurate compound can be collected. A removal method is not particularly limited, and the unreacted isocyanate and the solvent can be removed by distillation separation, for example. In addition, the removal is desirably performed at low temperature, and is preferably performed using a device that has a large evaporation surface with respect to liquid and good evaporation efficiency, such as a falling thin-film evaporator, a thin-film evaporation device, a molecular distillation device.

When performing the isocyanurate-forming reaction, the isocyanate compound and α-methylstyrene may each independently be subjected to the reaction system, or the isocyanate composition containing the isocyanate compound and α-methylstyrene is prepared in advance, and then, the isocyanate composition may be subjected to the reaction system.

In the present embodiment, the isocyanate composition subjected to the isocyanurate-forming reaction contains, for example, the isocyanate compound having an isocyanate group and, with respect to 100 parts by mass of the isocyanate compound, $5.0 \times 10^{-4}$ parts by mass or more and 2.0 parts by mass or less of benzyltoluene. The isocyanurate-forming reaction can be more easily performed by preparing the isocyanate composition like this.

On the basis of the total amount of the isocyanate composition, the content of the isocyanate compound in the isocyanate composition may be 98 mass % or more, and may also be 99 mass % or more.

Moreover, the isocyanate composition may further contain a compound represented by formula (1), and the content thereof is preferably $2.0 \times 10^{-4}$ parts by mass or more and 1.0 part by mass or less with respect to 100 parts by mass of the isocyanate compound. The isocyanurate-forming reaction to which the compound represented by formula (1) is added can thus be easily performed.

Furthermore, the isocyanate composition may further contain α-methylstyrene, and the content thereof is preferably $2.0 \times 10^{-4}$ parts by mass or more and 1.0 part by mass or less with respect to 100 parts by mass of the isocyanate compound. The isocyanurate-forming reaction to which α-methylstyrene is added can thus be easily performed.

Heretofore, the preferred embodiment of the present invention has been described, but the present invention is not limited to the above-described embodiment. For example, the present invention can also be a method for reducing the amount of the catalyst in the isocyanurate-forming reaction of the isocyanate compound, and a method for improving thermal yellowing of the isocyanurate compound generated in the isocyanurate-forming reaction of the isocyanurate compound.

<Use of Isocyanate Polymer>

A block isocyanate polymer can be manufactured by using a composition including various isocyanate polymers obtained by the above-described method and blocking a part or all of the isocyanate groups of the isocyanate polymers by a blocking agent. The blocking agent that can be used here are as follows.

The blocking agent is a compound having one active hydrogen in the molecule, and examples thereof include compounds of alcohol, alkylphenol, phenol, active methylene, mercaptan, acid amide, acid imide, imidazole, urea, oxime, amine, imine, and pyrazole compounds. More specific examples of the blocking agent are shown below.

(i) alcohols: methyl alcohol, ethyl alcohol, 2-propyl alcohol, n-butyl alcohol, sec-butyl alcohol, 2-ethyl-1-hexyl alcohol, 2-methoxyethyl alcohol, 2-ethoxyethyl alcohol, 2-butoxyethyl alcohol and the like (ii) alkylphenols: mono- and dialkylphenols including an alkyl group having 4 or more carbon atoms as a substituent group, for example, monoalkylphenols such as n-propylphenol, isopropylphenol, n-butylphenol, sec-butylphenol, t-butylphenol, n-hexylphenol, 2-ethylhexylphenol, n-octylphenol, and n-nonylphenol, and dialkylphenols such as di-n-propylphenol, diisopropylphenol, isopropylcresol, di-n-butylphenol, di-t-butylphenol, di-sec-butylphenol, di-n-octylphenol, di-2-ethylhexylphenol and di-n-nonylphenol (iii) phenols: phenol, cresol, ethylphenol, styrenated phenol, hydroxybenzoic acid ester and the like (iv) active methylenes: dimethyl malonate, diethyl malonate, methyl acetoacetate, ethyl acetoacetate, acetylacetone and the like (v) mercaptans: butyl mercaptan, dodecyl mercaptan and the like (vi) acid amides: acetanilide, amide acetate, ε-caprolactam, δ-valerolactam, γ-butyrolactam and the like (vii) acid imides: succinimide, maleinimide and the like (viii) imidazoles: imidazole, 2-methylimidazole and the like (ix) ureas: urea, thiourea, ethyleneurea and the like (x) oximes: formaldoxime, acetaldoxime, acetoxime, methyl ethyl ketoxime, cyclohexanone oxime and the like (xi) amines: diphenylamine, aniline, carbazole, di-n-propylamine, diisopropylamine, isopropylethylamine and the like (xii) imines: ethyleneimine, polyethyleneimine and the like (xiii) pyrazoles: pyrazole, 3-methylpyrazole, 3,5-dimethylpyrazole and the like A preferred blocking agent is at least one selected from alcohols, oximes, acid amides, active methylenes, and pyrazoles.

Moreover, for the purpose of improving water dispersibility, a composition of a hydrophilic group-modified isocyanate polymer, in which a part of the isocyanate groups of various isocyanate polymers obtained by the above-described method is modified by an active hydrogen-containing hydrophilic compound, can also be obtained.

The active hydrogen-containing hydrophilic compound is selected from non-ionic hydrophilic compounds, anionic hydrophilic compounds, and cationic hydrophilic compounds. Among them, in terms of easiness of manufacture, non-ionic hydrophilic compounds and anionic hydrophilic compounds are preferable, and non-ionic hydrophilic compounds are further preferable. These hydrophilic compounds may be used alone or two or more kinds thereof may be used in combination.

Examples of the non-ionic hydrophilic compounds include polyethylene glycol compounds having at least three continuous ethylene oxide groups. Furthermore, the number average molecular weight of the non-ionic hydrophilic compounds is preferably 200 to 2000. The lower limit of the number average molecular weight is more preferably 300, and further preferably 400. The upper limit of the number average molecular weight is more preferably 1500, further preferably 1200, and most preferably 1000. By the lower limit of the number average molecular weight of 200 or more, sufficient water dispersibility of the composition can be obtained. In contrast, by the upper limit of the number average molecular weight of 2000 or less, reduction in physical properties of a coating film, such as water resistance after baking, can be suppressed.

The exemplified polyethylene glycol compounds having at least three continuous ethylene oxide groups may have other oxyalkylene groups, specifically, such as an oxypropylene group and an oxystyrene group, at the ethylene oxide unit. In that case, the molar ratio of the ethylene oxide group is preferably 60 mol % or more, more preferably 70 mol % or more, and most preferably 80 mol % or more. The molar ratio of the ethylene oxide group is preferably high because compatibility in a water-based coating material can be effectively improved.

Examples of the polyethylene glycol compounds include monoalkoxy polyethylene glycols, and polyethylene glycols or triols; Pluronic polypropylene glycols or triols, in which ethylene oxide is addition-polymerized to the terminal of polypropylene glycol; polyoxypropylene polyoxyethylene copolymer diols or triols; and polyoxypropylene polyoxyethylene block polymer diols or triols. In particular, monoalkoxy polyethylene glycols and polyethylene glycols are preferable, and monoalkoxy polyethylene glycols are further preferable. Monoalkoxy polyethylene glycols are compounds having a structure in which a monoalcohol is added to one terminal of polyethylene glycol. The monoalcohol that can be used for monoalkoxy polyethylene glycol has preferably 1 to 8 carbon atoms, more preferably 1 to 6 carbon atoms, and further preferably 1 to 4 carbon atoms. Methyl alcohol and ethyl alcohol are most preferable.

Therefore, among monoalkoxy polyethylene glycols, monomethoxy polyethylene glycol or monoethoxy polyethylene glycol is preferable, and monomethoxy polyethylene glycol is most preferable.

Among these polyethylene glycol compounds used as the active hydrogen-containing hydrophilic compound, polyethylene glycol compounds having a number average molecular weight of 200 to 2000, to whose one terminal a monoalcohol having 1 to 4 carbon atoms is added, are most preferable.

Specific examples of polyethylene glycols include PEG 200, 300, 400, 600, 1000, and 2000 manufactured by NOF Corporation. Moreover, examples of monomethoxy polyethylene glycol include UNIOX M400, 550, 1000, and 2000 manufactured by NOF Corporation and MPG-081 manufactured by Nippon Nyukazai Co., Ltd.

Examples of the anionic hydrophilic compounds include carboxy group-containing compounds and sulfo group-containing compounds. Examples of the carboxy group-containing compounds include monohydroxycarboxylic acid, dihydroxycarboxylic acid, and derivatives thereof. Among the carboxy group-containing compounds, monohydroxycarboxylic acid or dihydroxycarboxylic acid is preferable, and monohydroxycarboxylic acid is further preferable.

Specific examples of the carboxy group-containing compounds include hydroxypivalinic acid, 2,2-dimethylol propionic acid, 2,2-dimethylol butanoic acid, and derivatives formed therefrom as initiators, such as polycaprolactone diol and polyether polyol. In the case of using the carboxy group-containing compounds, it is preferably neutralized with a neutralizing agent after manufacturing a block polyisocyanate composition. Examples of the neutralizing agent include alkali metals, alkali earth metals, ammonia, and tertiary amines such as trimethylamine, triethylamine and dimethylethanolamine.

Examples of the sulfo group-containing compounds include aminoethylsulfonic acid, ethylenediamino-propyl-β-ethylsulfonic acid, 1,3-propylenediamine-β-ethylsulfonic acid, and N,N-bis(2-hydroxyethyl)-2-aminoethane sulfonic acid. In the case of using the sulfo group-containing compounds, it is preferably neutralized with a neutralizing agent after manufacturing a block polyisocyanate composition. Examples of the neutralizing agent include alkali metals, alkali earth metals, ammonia, and tertiary amines such as trimethylamine, triethylamine and dimethylethanolamine.

When the carboxy group-containing compounds are compared with the sulfo group-containing compounds, the carboxy group-containing compounds are preferable in terms of easiness of manufacture and compatibility in a water-based coating material.

Examples of the cationic hydrophilic compounds include hydroxy group-containing amino compounds. Specific examples thereof include dimethylethanolamine, diethylethanolamine, and hydroxypyridine. In the case of using the hydroxy group-containing amino compounds, it is preferably neutralized with a neutralizing agent after manufacturing a block polyisocyanate composition as well as the above. Examples of the neutralizing agent include organic acids such as acetic acid, propionic acid, butanoic acid, and 2-ethylhexanoic acid.

Examples of the active hydrogen of the active hydrogen-containing hydrophilic compound include hydrogen of a hydroxy group in the case of non-ionic hydrophilic compounds. Examples thereof include hydrogen of a hydroxy group in the case of hydroxypivalinic acid, and, hydrogen of an amino group in the case of aminoethylsulfonic acid, which are the anionic hydrophilic compounds. Examples thereof include hydrogen of a hydroxy group in the case of dimethylethanolamine that is the cationic hydrophilic compound.

Moreover, regarding the altered amount of the active hydrogen-containing hydrophilic compound, if the isocyanate group of the polyisocyanate composition is A mol and the active hydrogen group of the active hydrogen-containing hydrophilic compound is B mol, B/(A+B) is preferably 0.40 or less, more preferably 0.35 or less, further preferably 0.30 or less, and most preferably 0.20 or less. When B/(A+B) is 0.40 or less, a cross-linkage property is difficult to be decreased, and water resistance of a cross-linkage coating film using the polyisocyanate composition tends to be difficult to be decreased.

Furthermore, when being used as a water-based one-liquid coating material and a cross-linking agent for coating agents, a blocking agent and an active hydrogen-containing hydrophilic compound may be made to react with the isocyanate polymer obtained in the embodiment, respectively.

It is surprising that, also in the case where a block isocyanate or an active hydrogen-containing hydrophilic compound is made to addition-react using the composition containing the isocyanate polymer obtained in the present embodiment, the reaction rate is high and coloration of a product after the reaction is suppressed.

As described above, the polyisocyanate composition of the present embodiment, a method for performing distillation purification using the polyisocyanate composition, a distilled polyisocyanate composition containing a distillation-purified polyisocyanate, a manufacturing method of an isocyanate polymer to react a polyisocyanate contained in the above-described polyisocyanate composition, and a composition containing the above-described isocyanate polymer are a manufacturing method of a composition whose coloration is suppressed and a composition for manufacturing a composition whose coloration is suppressed, and suitably used as raw materials such as a coating material and an adhesive in fields requiring quality of appearance.

EXAMPLES

The present invention will be described in more detail below by Examples. However, the present invention is not limited to the following Examples.

<NCO Content by Percentage (NCO %)>

The NCO content by percentage (NCO %) was obtained by mass % of by neutralizing the isocyanate group in the test portion with excessive 2 N amine and then carrying out back titration with 1 N hydrochloric acid.

<Number Average Molecular Weight>

The number average molecular weight of the test portion was measured by gel permeation chromatography (GPC). The following method was used in the measurement by GPC.

Apparatus used: HLC-8120 (a product of Tosoh Corporation),

Column used: TSK GEL Super H1000, TSK GEL Super H2000, TSK GEL Super H3000 (all of these are products of Tosoh Corporation), Concentration of test portion: 5 wt/vol % (a test portion (50 mg) was dissolved in 1 mL tetrahydrofuran (THF)), Carrier: THF, Determination method: Parallax refractometer, Outflow: 0.6 mL/min, Column temperature: 30° C.

In producing the calibration curve, polystyrene of molecular weight of 1,000 to 20,000 and an isocyanurate derivatives (trimers, pentamers, and heptamers) of 1,6-diisocyanate hexane were used.

<Measurement of Mass Concentration of Diisocyanate Monomer in Polyisocyanate Composition>

A 20 mL sample bottle was placed on a digital balance, and an accurately weighted 1 g of a sample was added. Next, an accurately weighted 0.03 to 0.04 g of nitrobenzene (an internal standard solution) was added to the sample bottle. Finally, ethyl acetate (9 mL) was added to the sample bottle and the lid was closed. The mixture was sufficiently stirred and used as the test portion. The test portion was subjected to gas chromatography analysis under the following conditions and the amount of the diisocyanate monomer was analyzed.

Apparatus: "GC-8A" (a product of Shimadzu Corporation)
Column: "Silicone OV-17" (a product of Shinwa Chemical Industries Ltd.)
Column oven temperature: 120° C.
Injection/detector temperature: 160° C.

<Hazen Color Number>

For the Hazen color number, numerical values obtained by measurement by a Hazen meter are described.

Example A1

A polyisocyanate composition comprising 98.7 mass % of hexamethylene diisocyanate and 2.1 mass ppm of α-methylstyrene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of hexamethylene diisocyanate was 99.9 mass % and that sufficiently purified hexamethylene diisocyanate was obtained. The Hazen color number (APHA, measured by a Hazen meter) of the obtained fraction was 26. Note that a mixed solution comprising hexamethylene diisocyanate and a hexamethylene diisocyanate multimer (a compound having an isocyanurate ring structure) was recovered from the column bottom, and the flow characteristics of the mixed solution were satisfactory.

Examples A2 to A11

In a similar manner as Example A1 except that the content of hexamethylene diisocyanate and the content of α-methylstyrene in the polyisocyanate composition were changed as illustrated in Table 1, a fraction comprising 99.9 mass % content of hexamethylene diisocyanate was obtained. The Hazen color number (APHA) of the obtained fraction was as illustrated in Table 1.

Example A12

A polyisocyanate composition comprising 98.1 mass % of hexamethylene diisocyanate, 250 mass ppm of α-methylstyrene, and 350 mass ppm of a compound represented by formula (5-1) or (5-2) was prepared.

[Chemical Formula 39]

(5-1)

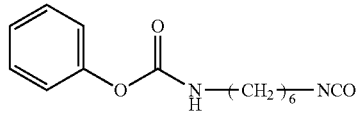

(5-2)

Distillation purification was carried out for the prepared polyisocyanate composition in the similar manner as Example A1 to obtain a fraction comprising 99.9 mass % of hexamethylene diisocyanate. The Hazen color number (APHA) of the obtained fraction was 8.

Example A13

A polyisocyanate composition comprising 98.5 mass % of hexamethylene diisocyanate, 150 mass ppm of α-methylstyrene, 500 mass ppm of a compound represented by formula (5-1) or (5-2), and 1,300 mass ppm of benzyltoluene was prepared.

Distillation purification was carried out for the prepared polyisocyanate composition in the similar manner as Example A1 to obtain a fraction comprising 99.9 mass % of hexamethylene diisocyanate. The Hazen color number (APHA) of the obtained fraction was 5.

Comparative Examples A1 and A2

In a similar manner as Example A1 except that the content of hexamethylene diisocyanate and the content of α-methylstyrene in the polyisocyanate composition were changed as illustrated in Table 1, a fraction comprising 99.9 mass % of content of hexamethylene diisocyanate was obtained. The Hazen color number (APHA) of the obtained fraction was as illustrated in Table 1.

Results of respective Examples and Comparative Examples are illustrated in Table 1. Note that in Table 1, "HMDI" denotes the content of hexamethylene diisocyanate (mass %), "αMS" denotes the content of α-methylstyrene (mass ppm), "5-1, 5-2" denotes the total content of a compound represented by formula (5-1) or (5-2) (mass ppm), and "BT" denotes the content of benzyltoluene (mass ppm).

TABLE 1

|  | Isocyanate composition | | | | Fraction | |
|---|---|---|---|---|---|---|
|  | HMDI (mass %) | αMS (mass ppm) | 5-1, 5-2 (mass ppm) | BT (mass ppm) | HMDI (mass %) | Hazen color number (APHA) |
| Example A1 | 98.7 | 2.1 | — | — | 99.9 | 26 |
| Example A2 | 98.8 | 3.5 | — | — | 99.9 | 20 |
| Example A3 | 98.1 | 5.5 | — | — | 99.9 | 15 |
| Example A4 | 98.3 | 12 | — | — | 99.9 | 10 |
| Example A5 | 98.2 | 930 | — | — | 99.9 | 11 |
| Example A6 | 98.5 | 1200 | — | — | 99.9 | 15 |
| Example A7 | 98.1 | 2800 | — | — | 99.9 | 16 |

TABLE 1-continued

|  | Isocyanate composition | | | | Fraction | |
|---|---|---|---|---|---|---|
|  | HMDI (mass %) | αMS (mass ppm) | 5-1, 5-2 (mass ppm) | BT (mass ppm) | HMDI (mass %) | Hazen color number (APHA) |
| Example A8 | 98.1 | 3100 | — | — | 99.9 | 21 |
| Example A9 | 98.3 | 4600 | — | — | 99.9 | 22 |
| Example A10 | 98.4 | 5100 | — | — | 99.9 | 26 |
| Example A11 | 98.2 | 9000 | — | — | 99.9 | 27 |
| Example A12 | 98.1 | 250 | 350 | — | 99.9 | 8 |
| Example A13 | 98.5 | 150 | 500 | 1300 | 99.9 | 5 |
| Comparative Example A1 | 98.1 | 1.1 | — | — | 99.9 | 35 |
| Comparative Example A2 | 98.2 | 11000 | — | — | 99.9 | 38 |

Example A14

A polyisocyanate composition comprising 98.3 mass % of hexamethylene diisocyanate and 2.8 mass ppm of 2,4,4-trimethylpentene-1 was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of hexamethylene diisocyanate was 99.9 mass % and that sufficiently purified hexamethylene diisocyanate was obtained. The Hazen color number (APHA) of the obtained fraction was 15. Note that a mixed solution comprising hexamethylene diisocyanate and a hexamethylene diisocyanate multimer (a compound having an isocyanurate ring structure) was recovered from the column bottom, and the flow characteristics of the mixed solution were satisfactory.

Examples A15 to A24

In a similar manner as Example A1 except that the content of hexamethylene diisocyanate and the content of 2,4,4-trimethylpentene-1 in the polyisocyanate composition were changed as illustrated in Table 2, a fraction comprising 99.9 mass % of content of hexamethylene diisocyanate was obtained. The Hazen color number (APHA) of the obtained fraction was as illustrated in Table 2.

Example A25

A polyisocyanate composition comprising 98.3 mass % of hexamethylene diisocyanate, 220 mass ppm of 2,4,4-trimethylpentene-1, and 320 mass ppm of a compound represented by formula (5-1) or (5-2) was prepared.

Distillation purification was carried out for the prepared polyisocyanate composition in the similar manner as Example A1 to obtain a fraction comprising 99.9 mass % of hexamethylene diisocyanate. The Hazen color number (APHA) of the obtained fraction was 4.

Example A26

A polyisocyanate composition comprising 98.5 mass % of hexamethylene diisocyanate, 150 mass ppm of 2,4,4-trimethylpentene-1, 600 mass ppm of a compound represented by formula (5-1) or (5-2), and 1,200 mass ppm of n-hexadecane was prepared.

Distillation purification was carried out for the prepared polyisocyanate composition in the similar manner as Example A1 to obtain a fraction comprising 99.9 mass % of hexamethylene diisocyanate. The Hazen color number (APHA) of the obtained fraction was 3.

Comparative Examples A3 and A4

In a similar manner as Example A14 except that the content of hexamethylene diisocyanate and the content of 2,4,4-trimethylpentene-1 in the polyisocyanate composition were changed as illustrated in Table 2, a fraction comprising 99.9 mass % of content of hexamethylene diisocyanate was obtained. The Hazen color number (APHA) of the obtained fraction was as illustrated in Table 2.

Results of respective Examples and Comparative Examples are illustrated in Table 2. Note that in Table 2, "HMDI" denotes the content of hexamethylene diisocyanate (mass %), "TMP" denotes the content of 2,4,4-trimethylpentene-1 (mass ppm), "5-1, 5-2" denotes the total content of a compound represented by formula (5-1) or (5-2) (mass ppm), and "HD" denotes the content of n-hexadecane (mass ppm).

TABLE 2

|  | Isocyanate composition | | | | Fraction | |
|---|---|---|---|---|---|---|
|  | HMDI (mass %) | TMP (mass ppm) | 5-1, 5-2 (mass ppm) | HD (mass ppm) | HMDI (mass %) | Hazen color number (APHA) |
| Example A14 | 98.3 | 2.8 | — | — | 99.9 | 15 |
| Example A15 | 98.3 | 3.6 | — | — | 99.9 | 13 |
| Example A16 | 98.4 | 5.3 | — | — | 99.9 | 10 |

TABLE 2-continued

|  | Isocyanate composition | | | | Fraction | |
|---|---|---|---|---|---|---|
|  | HMDI (mass %) | TMP (mass ppm) | 5-1, 5-2 (mass ppm) | HD (mass ppm) | HMDI (mass %) | Hazen color number (APHA) |
| Example A17 | 98.1 | 12 | — | — | 99.9 | 8 |
| Example A18 | 98.5 | 980 | — | — | 99.9 | 8 |
| Example A19 | 98.5 | 1100 | — | — | 99.9 | 9 |
| Example A20 | 98.4 | 2800 | — | — | 99.9 | 9 |
| Example A21 | 98.4 | 3200 | — | — | 99.9 | 11 |
| Example A22 | 98.4 | 4800 | — | — | 99.9 | 12 |
| Example A23 | 98.6 | 5200 | — | — | 99.9 | 13 |
| Example A24 | 98.1 | 9300 | — | — | 99.9 | 15 |
| Example A25 | 98.3 | 220 | 320 | — | 99.9 | 4 |
| Example A26 | 98.5 | 150 | 600 | 1200 | 99.9 | 3 |
| Comparative Example A3 | 98.6 | 1.0 | — | — | 99.9 | 30 |
| Comparative Example A4 | 98.1 | 12000 | — | — | 99.9 | 32 |

Example A27

A polyisocyanate composition comprising 98.3 mass % of hexamethylene diisocyanate and 2.2 mass ppm of 2-methylbutene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of hexamethylene diisocyanate was 99.9 mass % and that sufficiently purified hexamethylene diisocyanate was obtained. The Hazen color number (APHA, measured by a Hazen meter) of the obtained fraction was 15. Note that a mixed solution comprising hexamethylene diisocyanate and a hexamethylene diisocyanate multimer (a compound having an isocyanurate ring structure) was recovered from the column bottom, and the flow characteristics of the mixed solution were satisfactory.

Examples A28 to A37

In a similar manner as Example A1 except that the content of hexamethylene diisocyanate and the content of 2-methylbutene in the polyisocyanate composition were changed as illustrated in Table 3, a fraction comprising 99.9 mass % of content of hexamethylene diisocyanate was obtained. The Hazen color number (APHA) of the obtained fraction was as illustrated in Table 3.

Example A38

A polyisocyanate composition comprising 98.3 mass % of hexamethylene diisocyanate, 220 mass ppm of 2-methylbutene, and 310 mass ppm of a compound represented by formula (6-1) or (6-2) was prepared.

[Chemical Formula 40]

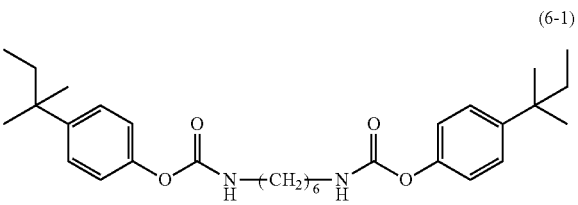

(6-1)

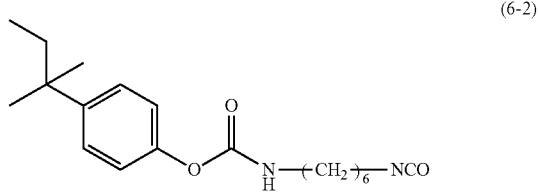

(6-2)

Distillation purification was carried out for the prepared polyisocyanate composition in the similar manner as Example A27 to obtain a fraction comprising 99.9 mass % of hexamethylene diisocyanate. The Hazen color number (APHA) of the obtained fraction was 3.

Example A39

A polyisocyanate composition comprising 98.6 mass % of hexamethylene diisocyanate, 130 mass ppm of 2-methylbutene, 640 mass ppm of a compound represented by formula (6-1) or (6-2), and 1,100 mass ppm of n-pentadecane was prepared.

Distillation purification was carried out for the prepared polyisocyanate composition in the similar manner as Example A27 to obtain a fraction comprising 99.9 mass % of hexamethylene diisocyanate. The Hazen color number (APHA) of the obtained fraction was 2.

Comparative Examples A5 and A6

In a similar manner as Example A1 except that the content of hexamethylene diisocyanate and the content of α-methylstyrene in the polyisocyanate composition were changed as illustrated in Table 3, a fraction comprising 99.9 mass % of content of hexamethylene diisocyanate was obtained. The Hazen color number (APHA) of the obtained fraction was as illustrated in Table 3.

Results of respective Examples and Comparative Examples are illustrated in Table 3. Note that in Table 3, "HMDI" denotes the content of hexamethylene diisocyanate (mass %), "MB" denotes the content of 2-methylbutene (mass ppm), "6-1, 6-2" denotes the total content of a compound represented by formula (6-1) or (6-2) (mass ppm), and "PD" denotes the content of n-pentadecane (mass ppm).

[Chemical Formula 41] (7-1)

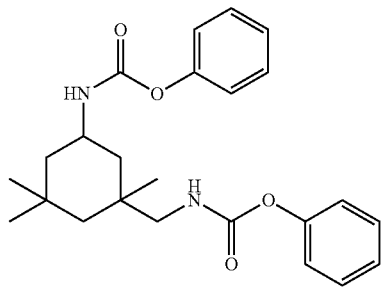

TABLE 3

| | Isocyanate composition | | | | Fraction | |
| --- | --- | --- | --- | --- | --- | --- |
| | | | | | | Hazen color |
| | HMDI (mass %) | MB (mass ppm) | 6-1, 6-2 (mass ppm) | PD (mass ppm) | HMDI (mass %) | number (APHA) |
| Example A27 | 98.3 | 2.2 | — | — | 99.9 | 15 |
| Example A28 | 98.1 | 3.4 | — | — | 99.9 | 14 |
| Example A29 | 98.5 | 5.2 | — | — | 99.9 | 10 |
| Example A30 | 98.3 | 11 | — | — | 99.9 | 5 |
| Example A31 | 98.4 | 960 | — | — | 99.9 | 5 |
| Example A32 | 98.5 | 1100 | — | — | 99.9 | 8 |
| Example A33 | 98.4 | 2600 | — | — | 99.9 | 8 |
| Example A34 | 98.2 | 3200 | — | — | 99.9 | 10 |
| Example A35 | 98.6 | 4600 | — | — | 99.9 | 10 |
| Example A36 | 98.9 | 5400 | — | — | 99.9 | 18 |
| Example A37 | 98.2 | 9100 | — | — | 99.9 | 20 |
| Example A38 | 98.3 | 220 | 310 | — | 99.9 | 3 |
| Example A39 | 98.6 | 130 | 640 | 1100 | 99.9 | 2 |
| Comparative Example A5 | 98.2 | 1.1 | — | — | 99.9 | 25 |
| Comparative Example A6 | 98.2 | 12000 | — | — | 99.9 | 25 |

Example A40

A polyisocyanate composition comprising 98.2 mass % of isophorone diisocyanate and 8 mass ppm of styrene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of isophorone diisocyanate was 99.9 mass % and that sufficiently purified isophorone diisocyanate was obtained. The Hazen color number (APHA, measured by a Hazen meter) of the obtained fraction was 7. Note that a mixed solution comprising isophorone diisocyanate and an isophorone diisocyanate multimer (a compound having an isocyanurate ring structure) was recovered from the column bottom, and the flow characteristics of the mixed solution were satisfactory.

Example A41

A polyisocyanate composition comprising 99.7 mass % of isophorone diisocyanate, 20 mass ppm of styrene, and an 80 mass ppm of compound represented by formula (7-1) was prepared.

Distillation purification was carried out for the prepared polyisocyanate composition in the similar manner as Example A40 to obtain a fraction comprising 99.9 mass % of isophorone diisocyanate. The Hazen color number (APHA) of the obtained fraction was 4.

Example A42

A polyisocyanate composition comprising 98.3 mass % of isophorone diisocyanate, 11 mass ppm of styrene, 100 mass ppm of a compound represented by formula (7-1), and 1,500 mass ppm of decyl ether was prepared.

Distillation purification was carried out for the prepared polyisocyanate composition in the similar manner as Example A40 to obtain a fraction comprising 99.9 mass % of isophorone diisocyanate. The Hazen color number (APHA) of the obtained fraction was 3.

Results of respective Examples and Comparative Examples are illustrated in Table 4. Note that in Table 4, "IPDI" denotes the content of isophorone diisocyanate (mass %), "ST" denotes the content of styrene (mass ppm), "7-1" denotes the content of a compound represented by formula (7-1) (mass ppm), and "DE" denotes the content of decyl ether (mass ppm).

TABLE 4

| | Isocyanate composition | | | | Fraction | |
|---|---|---|---|---|---|---|
| | IPDI (mass %) | ST (mass ppm) | 7-1 (mass ppm) | DE (mass ppm) | IPDI (mass %) | Hazen color number (APHA) |
| Example A40 | 98.2 | 8 | — | — | 99.9 | 7 |
| Example A41 | 99.7 | 20 | 80 | — | 99.9 | 4 |
| Example A42 | 98.3 | 11 | 100 | 1500 | 99.9 | 3 |

Example A43

A polyisocyanate composition comprising 98.9 mass % of isophorone diisocyanate and 14 mass ppm of nonene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of isophorone diisocyanate was 99.9 mass % and that sufficiently purified isophorone diisocyanate was obtained. The Hazen color number (APHA, measured by a Hazen meter) of the obtained fraction was 5. Note that a mixed solution comprising isophorone diisocyanate and an isophorone diisocyanate multimer (a compound having an isocyanurate ring structure) was recovered from the column bottom, and the flow characteristics of the mixed solution were satisfactory.

Example A44

A polyisocyanate composition comprising 98.0 mass % of isophorone diisocyanate, 33 mass ppm of nonene, and 90 mass ppm of a compound represented by formula (8-1) was prepared.

[Chemical Formula 42]

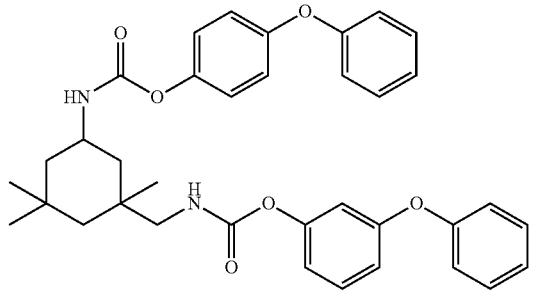

(8-1)

Distillation purification was carried out for the prepared polyisocyanate composition in the similar manner as Example A43 to obtain a fraction comprising 99.9 mass % of isophorone diisocyanate. The Hazen color number (APHA) of the obtained fraction was 3.

Example A45

A polyisocyanate composition comprising 97.7 mass % of isophorone diisocyanate, 12 mass ppm of nonene, 40 mass ppm of a compound represented by formula (8-1), and 350 mass ppm of dibenzyl ether was prepared.

Distillation purification was carried out for the prepared polyisocyanate composition in the similar manner as Example A43 to obtain a fraction comprising 99.9 mass % of isophorone diisocyanate. The Hazen color number (APHA) of the obtained fraction was 2.

Results of respective Examples and Comparative Examples are illustrated in Table 5. Note that in Table 5, "IPDI" denotes the content of isophorone diisocyanate (mass %), "NN" denotes the content of nonene (mass ppm), "8-1" denotes the content of a compound represented by formula (8-1) (mass ppm), and "DBE" denotes the content of dibenzyl ether (mass ppm).

TABLE 5

| | Isocyanate composition | | | | Fraction | |
|---|---|---|---|---|---|---|
| | IPDI (mass %) | NN (mass ppm) | 8-1 (mass ppm) | DBE (mass ppm) | IPDI (mass %) | Hazen color number (APHA) |
| Example A43 | 98.9 | 14 | — | — | 99.9 | 5 |
| Example A44 | 98.0 | 33 | 90 | — | 99.9 | 3 |
| Example A45 | 97.7 | 12 | 40 | 350 | 99.9 | 2 |

Example A46

A polyisocyanate composition comprising 98.5 mass % of hexamethylene diisocyanate and 8 mass ppm of n-octene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of hexamethylene diisocyanate was 99.9 mass % and that sufficiently purified hexamethylene diisocyanate was obtained. The Hazen color number (APHA, measured by a Hazen meter) of the obtained fraction was 5. Note that a mixed solution comprising hexamethylene diisocyanate and a hexamethylene diisocyanate multimer (a compound having an isocyanurate ring structure) was recovered from the column bottom, and the flow characteristics of the mixed solution were satisfactory.

Example A47

A polyisocyanate composition comprising 98.1 mass % of hexamethylene diisocyanate, 20 mass ppm of n-octene, and 40 mass ppm of a compound represented by formula (5-1) or (5-2) was prepared.

Distillation purification was carried out for the prepared polyisocyanate composition in the similar manner as Example A46 to obtain a fraction comprising 99.9 mass % of hexamethylene diisocyanate. The Hazen color number (APHA) of the obtained fraction was 3.

Example A48

A polyisocyanate composition comprising 98.1 mass % of hexamethylene diisocyanate, 11 mass ppm of n-octene, 20 mass ppm of a compound represented by formula (5-1) or (5-2), and 100 mass ppm of butylphenyl ether was prepared.

Distillation purification was carried out for the prepared polyisocyanate composition in the similar manner as Example A46 to obtain a fraction comprising 99.9 mass % of hexamethylene diisocyanate. The Hazen color number (APHA) of the obtained fraction was 2.

Results of respective Examples and Comparative Examples are illustrated in Table 6. Note that in Table 6, "HMDI" denotes the content of hexamethylene diisocyanate (mass %), "NO" denotes the content of n-octene (mass ppm), "5-1, 5-2" denotes the total content of a compound represented by formula (5-1) or (5-2) (mass ppm), and "BPE" denotes the content of butylphenyl ether (mass ppm).

TABLE 6

| | Isocyanate composition | | | | Fraction | |
|---|---|---|---|---|---|---|
| | HMDI (mass %) | NO (mass ppm) | 5-1, 5-2 (mass ppm) | BPE (mass ppm) | HMDI (mass %) | Hazen color number (APHA) |
| Example A46 | 98.5 | 8 | — | — | 99.9 | 5 |
| Example A47 | 98.1 | 20 | 40 | — | 99.9 | 3 |
| Example A48 | 98.1 | 11 | 20 | 100 | 99.9 | 2 |

Example A49

A polyisocyanate composition comprising 98.5 mass % of dicyclohexylmethane diisocyanate and 8 mass ppm of α-methylstyrene was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of dicyclohexylmethane diisocyanate was 99.9 mass % and that sufficiently purified dicyclohexylmethane diisocyanate was obtained. The Hazen color number (APHA, measured by a Hazen meter) of the obtained fraction was 10. Note that a mixed solution comprising dicyclohexylmethane diisocyanate and a dicyclohexylmethane diisocyanate multimer (a compound having an isocyanurate ring structure) was recovered from the column bottom, and the flow characteristics of the mixed solution were satisfactory.

Example A50

A polyisocyanate composition comprising 98.1 mass % of dicyclohexylmethane diisocyanate, 25 mass ppm of α-methylstyrene, and 20 mass ppm of a compound represented by formula (9-1) or (9-2) was prepared.

[Chemical Formula 43]

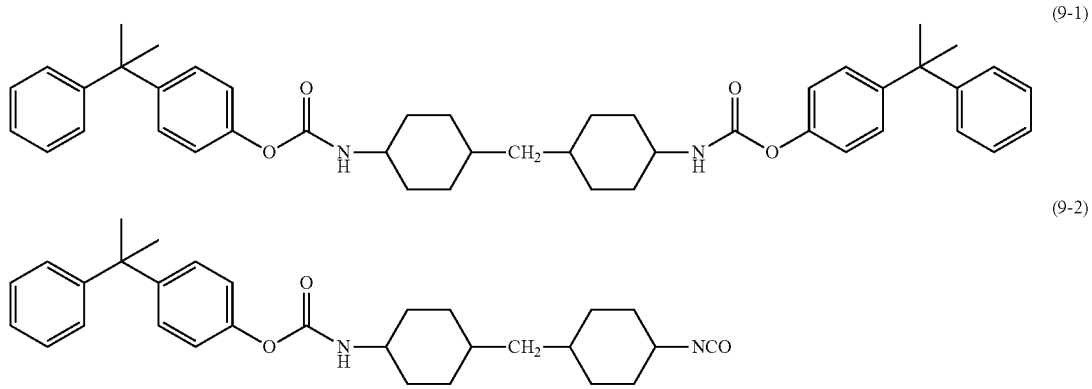

(9-1)

(9-2)

Distillation purification was carried out for the prepared polyisocyanate composition in the similar manner as Example A49 to obtain a fraction comprising 99.9 mass % of dicyclohexylmethane diisocyanate. The Hazen color number (APHA) of the obtained fraction was 6.

Example A51

A polyisocyanate composition comprising 98.1 mass % of dicyclohexylmethane diisocyanate, 33 mass ppm of α-methylstyrene, 10 mass ppm of a compound represented by formula (9-1) or (9-2), and 320 mass ppm of decamethyltetrasiloxane was prepared.

Distillation purification was carried out for the prepared polyisocyanate composition in the similar manner as Example A49 to obtain a fraction comprising 99.9 mass % of isophorone diisocyanate. The Hazen color number (APHA) of the obtained fraction was 2.

Results of respective Examples and Comparative Examples are illustrated in Table 7. Note that in Table 7, "H-MDI" denotes the content of dicyclohexylmethane diisocyanate (mass %), "αMS" denotes the content of α-methylstyrene (mass ppm), "9-1, 9-2" denotes the total content of a compound represented by formula (9-1) or (9-2) (mass ppm), and "DMTS" denotes the content of decamethyltetrasiloxane (mass ppm).

Example A52

A polyisocyanate composition comprising 98.5 mass % of hexamethylene diisocyanate and 2.8 mass ppm of di-n-butyl carbonate was prepared.

The prepared polyisocyanate composition was supplied to a continuous multistage distillation column (height: 3,000 mm, internal diameter: 50 mm; Dixon packing was used as the filler). The pressure at the top of the distillation column was 1 kPa (absolute pressure) and the heat required for the distillation was supplied from a reboiler. After the temperature distribution in the column was stabilized, a fraction was taken out from the side cut line provided at a location 600 mm below the column top in the direction of height. The obtained fraction was analyzed by gas chromatography, and it was confirmed that the content of hexamethylene diisocyanate was 99.9 mass % and that sufficiently purified hexamethylene diisocyanate was obtained. The Hazen color number (APHA, measured by a Hazen meter) of the obtained fraction was 18. Note that a mixed solution comprising hexamethylene diisocyanate and a hexamethylene diisocyanate multimer (a compound having an isocyanurate ring structure) was recovered from the column bottom, and the flow characteristics of the mixed solution were satisfactory.

Examples A53 to A62

In a similar manner as Example A52 except that the content of hexamethylene diisocyanate and the content of di-n-butyl carbonate in the polyisocyanate composition were changed as illustrated in Table 8, a fraction comprising 99.9 mass % of content of hexamethylene diisocyanate was obtained. The Hazen color number (APHA) of the obtained fraction was as illustrated in Table 8.

Example A63

A polyisocyanate composition comprising 98.6 mass % of hexamethylene diisocyanate, 250 mass ppm of di-n-butyl carbonate, and 150 mass ppm of a compound represented by formula (10-1) or (10-2) was prepared.

TABLE 7

| | Isocyanate composition | | | | Fraction | |
| | | | | | | Hazen color |
| | H-MDI (mass %) | αMS (mass ppm) | 9-1, 9-2 (mass ppm) | DMTS (mass ppm) | H-MDI (mass %) | number (APHA) |
|---|---|---|---|---|---|---|
| Example A49 | 98.5 | 8 | — | — | 99.9 | 10 |
| Example A50 | 98.1 | 25 | 20 | — | 99.9 | 6 |
| Example A51 | 98.1 | 33 | 10 | 320 | 99.9 | 2 |

[Chemical Formula 44]

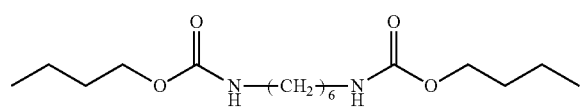
(10-1)

obtained. The Hazen color number (APHA) of the obtained fraction was as illustrated in Table 8.

Results of respective Examples and Comparative Examples are illustrated in Table 8. Note that in Table 8, "HMDI" denotes the content of hexamethylene diisocyanate (mass %), "DBC" denotes the content of di-n-butyl carbonate (mass ppm), "10-1, 10-2" denotes the total content of a compound represented by formula (10-1) or (10-2) (mass ppm), and "DBE" denotes the content of dibenzyl ether (mass ppm).

TABLE 8

| | Isocyanate composition | | | | Fraction | |
|---|---|---|---|---|---|---|
| | HMDI (mass %) | DBC (mass ppm) | 10-1, 10-2 (mass ppm) | DBE (mass ppm) | HMDI (mass %) | Hazen color number (APHA) |
| Example A52 | 98.5 | 2.8 | — | — | 99.9 | 18 |
| Example A53 | 98.1 | 3.3 | — | — | 99.9 | 15 |
| Example A54 | 98.3 | 5.5 | — | — | 99.9 | 12 |
| Example A55 | 98.6 | 12 | — | — | 99.9 | 12 |
| Example A56 | 98.7 | 930 | — | — | 99.9 | 12 |
| Example A57 | 98.4 | 1200 | — | — | 99.9 | 14 |
| Example A58 | 98.7 | 2800 | — | — | 99.9 | 16 |
| Example A59 | 98.5 | 3100 | — | — | 99.9 | 17 |
| Example A60 | 98.3 | 4600 | — | — | 99.9 | 18 |
| Example A61 | 98.3 | 5100 | — | — | 99.9 | 18 |
| Example A62 | 98.5 | 9000 | — | — | 99.9 | 18 |
| Example A63 | 98.6 | 250 | 150 | — | 99.9 | 10 |
| Example A64 | 98.4 | 150 | 100 | 200 | 99.9 | 8 |
| Comparative Example A7 | 98.3 | 0.5 | — | — | 99.9 | 30 |
| Comparative Example A8 | 98.3 | 14000 | — | — | 99.9 | 28 |

-continued

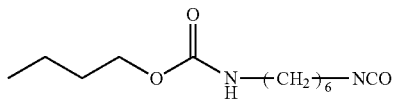
(10-2)

Distillation purification was carried out for the prepared polyisocyanate composition in the similar manner as Example A52 to obtain a fraction comprising 99.9 mass % of hexamethylene diisocyanate. The Hazen color number (APHA) of the obtained fraction was 10.

Example A64

A polyisocyanate composition comprising 98.4 mass % of hexamethylene diisocyanate, 150 mass ppm of di-n-butyl carbonate, 100 mass ppm of a compound represented by formula (10-1) or (10-2), and 200 mass ppm of dibenzyl ether was prepared.

Distillation purification was carried out for the prepared polyisocyanate composition in the similar manner as Example A52 to obtain a fraction comprising 99.9 mass % of hexamethylene diisocyanate. The Hazen color number (APHA) of the obtained fraction was 8.

Comparative Examples A7 and A8

In a similar manner as Example A52 except that the content of hexamethylene diisocyanate and the content of di-n-butyl carbonate in the polyisocyanate composition were changed as illustrated in Table 8, a fraction comprising 99.9 mass % of content of hexamethylene diisocyanate was Example B1

A polyisocyanate composition comprising 98.5 mass % of hexamethylene diisocyanate and 22 mass ppm of benzyltoluene (an isomer mixture) (note that the term "mass ppm" denotes "×10$^{-4}$ mass %") was prepared.

The prepared polyisocyanate composition (1,000 g) was placed in a four-neck glass flask comprising a thermometer, a stirrer, and a nitrogen seal tube, and then the air inside the flask was substituted with nitrogen, and the reaction liquid was heated to 70° C. while stirring. By measuring the refractive index of the reaction liquid, the catalyst (tetramethylammonium hydroxide) was gradually added until the degree of conversion of hexamethylene diisocyanate reached 20%, and a 85% aqueous phosphoric acid solution (0.5 g) was added when the degree of conversion of hexamethylene diisocyanate reached 20%, and then the reaction was terminated. In this process, the quantity of the catalyst necessary for achieving the 20% degree of conversion was 220 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound which was a polymer of hexamethylene diisocyanate.

Examples B2 to B15

An isocyanurate-forming reaction was carried out in a similar manner as Example B1 except that the content of hexamethylene diisocyanate and the content of benzyltoluene in the polyisocyanate composition were changed as illustrated in Table 9.

Example B16

A polyisocyanate composition comprising 99.0 mass % of hexamethylene diisocyanate, 1,300 mass ppm of benzyltoluene (an isomer mixture), and 530 mass ppm of a mixture of a compound represented by formula (11-1) and a compound represented by formula (11-2) (as two kinds of mixtures) was prepared.

[Chemical Formula 45]

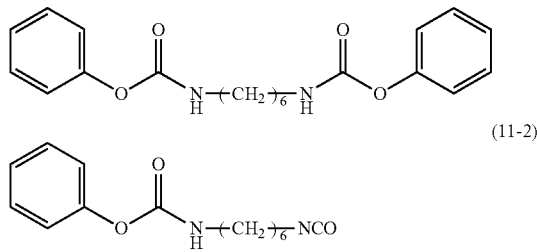

By using the prepared polyisocyanate composition, an isocyanurate-forming reaction was carried out in the similar manner as Example B1. In this process, the quantity of the catalyst necessary for achieving the 20% degree of conversion was 75 mass ppm with respect to the polyisocyanate composition used for the reaction.

Example B17

A polyisocyanate composition comprising 99.0 mass % of hexamethylene diisocyanate, 1,200 mass ppm of benzyltoluene (an isomer mixture), 610 mass ppm of α-methylstyrene, and 380 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B1. The quantity of the catalyst necessary for achieving the 20% degree of conversion was 70 mass ppm of with respect to the polyisocyanate composition used for the reaction.

Comparative Examples B1 and B2

An isocyanurate-forming reaction was carried out in a similar manner as Example B1 except that the content of hexamethylene diisocyanate and the content of benzyltoluene in the polyisocyanate composition were changed as illustrated in Table 9.

<Evaluation of Weatherability>

The weatherability of the isocyanurate compound was evaluated by the following method.

The isocyanurate compound and polyester polyol (Setal116 produced by Nuplex Resin) were mixed so that the equivalence ratio of the isocyanate group to the hydroxy group became 1.0, and a mixed solution of ethyl acetate/toluene/butyl acetate/xylene/propylene glycolmonomethyl ether acetate (mass ratio: 30/30/20/15/5) was added so that the mass of the content of the solid comprising the isocyanurate compound and polyol became 50% to obtain a coating solution. The coating solution was applied onto an enamel white panel by using an applicator so that the film thickness after drying became 40 μm, then the coating film was cured for 1 week under conditions of the temperature of 20° C. and the humidity of 63%, and then the weatherability of the panel was evaluated. For the evaluation of the weatherability, a dew panel weathermeter (a product of Suga Test Instruments Co., Ltd.) was used. The evaluation conditions were compliant with JIS D0205, i.e., the irradiation speed of 30 W/m$^2$ and the panel temperature of 60° C., and the test was carried out by cycle operation in which irradiation time and dew condensation time are set to be 4 hours, respectively.

Panels with the glossiness retention rate of 80% or more when the exposure time reached 1,200 hours were evaluated "A" and those with the glossiness retention rate of less than 80% were evaluated "B". Results of the tests are illustrated in Table 9.

The compositions of the polyisocyanate compositions and the quantities of the catalyst necessary for achieving the 20% degree of conversion in Examples and Comparative Examples are illustrated in Table 9. Note that in Table 9, "HMDI" denotes the content of hexamethylene diisocyanate (mass %), "BT" denotes the content of benzyltoluene (mass ppm), "11-1, 11-2" denotes the total content of a compound represented by formula (11-1) or (11-2) (mass ppm), "αMS" denotes the content of α-methylstyrene (mass ppm), and the "necessary catalyst quantity" denotes the quantity of the catalyst necessary for achieving the 20% degree of conversion (the ratio to the total quantity of polyisocyanate composition in mass ppm).

TABLE 9

|  | Isocyanate composition | | | | Necessary | |
| --- | --- | --- | --- | --- | --- | --- |
|  | HMDI (mass %) | BT (mass ppm) | 11-1, 11-2 (mass ppm) | αMS (mass ppm) | catalyst quantity (mass ppm) | Result of evaluation of weatherability |
| Example B1 | 98.5 | 22 | — | — | 220 | A |
| Example B2 | 99.3 | 43 | — | — | 210 | A |
| Example B3 | 98.9 | 55 | — | — | 160 | A |
| Example B4 | 99.1 | 92 | — | — | 150 | A |
| Example B5 | 98.1 | 110 | — | — | 110 | A |
| Example B6 | 98.8 | 290 | — | — | 100 | A |
| Example B7 | 98.5 | 330 | — | — | 85 | A |
| Example B8 | 98.3 | 2400 | — | — | 85 | A |
| Example B9 | 98.3 | 8000 | — | — | 90 | A |
| Example B10 | 98.1 | 10500 | — | — | 100 | A |
| Example B11 | 98.3 | 12600 | — | — | 110 | A |
| Example B12 | 98.2 | 13200 | — | — | 160 | A |

TABLE 9-continued

| | Isocyanate composition | | | | Necessary | |
| --- | --- | --- | --- | --- | --- | --- |
| | HMDI (mass %) | BT (mass ppm) | 11-1, 11-2 (mass ppm) | αMS (mass ppm) | catalyst quantity (mass ppm) | Result of evaluation of weatherability |
| Example B13 | 98.2 | 14800 | — | — | 170 | A |
| Example B14 | 98.1 | 15200 | — | — | 220 | A |
| Example B15 | 98.0 | 18300 | — | — | 250 | A |
| Example B16 | 99.0 | 1300 | 530 | — | 75 | A |
| Example B17 | 99.0 | 1200 | 380 | 610 | 70 | A |
| Comparative Example B1 | 99.0 | 3.0 | — | — | 930 | B |
| Comparative Example B2 | 97.5 | 22000 | — | — | 1220 | B |

Example B18

A polyisocyanate composition comprising 98.1 mass % of hexamethylene diisocyanate and 25 mass ppm of n-hexadecane was prepared.

The isocyanurate compound was prepared in the similar manner as Example B1, and the catalyst quantity was 230 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound, which was a polymer of hexamethylene diisocyanate.

Examples B19 to B32

An isocyanurate-forming reaction was carried out in a similar manner as Example B1 except that the content of hexamethylene diisocyanate and the content of n-hexadecane in the polyisocyanate composition were changed as illustrated in Table 10.

Example B33

A polyisocyanate composition comprising 99.2 mass % of hexamethylene diisocyanate, 1,400 mass ppm of n-hexadecane, and 630 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B18. In this process, the quantity of the catalyst necessary for achieving the 20% degree of conversion was 65 mass ppm with respect to the polyisocyanate composition used for the reaction.

Example B34

A polyisocyanate composition comprising 99.1 mass % of hexamethylene diisocyanate, 1,500 mass ppm of n-hexadecane, 120 mass ppm of 2,4,4-trimethylpentene-1, and 430 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B18. The quantity of the catalyst necessary for achieving the 20% degree of conversion was 55 mass ppm with respect to the polyisocyanate composition used for the reaction.

Comparative Examples B3 and B4

An isocyanurate-forming reaction was carried out in a similar manner as Example B18 except that the content of hexamethylene diisocyanate and the content of benzyltoluene in the polyisocyanate composition were changed as illustrated in Table 10.

The compositions of the polyisocyanate compositions and the quantities of the catalyst necessary for achieving the 20% degree of conversion in Examples and Comparative Examples are illustrated in Table 10. In Table 10, "HMDI" denotes the content of hexamethylene diisocyanate (mass %), "HD" denotes the content of n-hexadecane (mass ppm), "11-1, 11-2" denotes the total content of a compound represented by formula (11-1) or (11-2) (mass ppm), "TMP" denotes the content of 2,4,4-trimethylpentene-1 (mass ppm), and the "necessary catalyst quantity" denotes the quantity of the catalyst necessary for achieving the 20% degree of conversion (the ratio to the total quantity of polyisocyanate composition in mass ppm).

TABLE 10

| | Isocyanate composition | | | | Necessary | |
| --- | --- | --- | --- | --- | --- | --- |
| | HMDI (mass %) | HD (mass ppm) | 11-1, 11-2 (mass ppm) | TMP (mass ppm) | catalyst quantity (mass ppm) | Result of evaluation of weatherability |
| Example B18 | 98.1 | 25 | — | — | 230 | A |
| Example B19 | 98.2 | 45 | — | — | 200 | A |
| Example B20 | 98.3 | 52 | — | — | 170 | A |
| Example B21 | 98.9 | 93 | — | — | 140 | A |
| Example B22 | 99.1 | 112 | — | — | 120 | A |
| Example B23 | 99.2 | 280 | — | — | 100 | A |
| Example B24 | 98.3 | 320 | — | — | 85 | A |
| Example B25 | 98.5 | 2200 | — | — | 85 | A |
| Example B26 | 98.3 | 9000 | — | — | 88 | A |

TABLE 10-continued

|  | Isocyanate composition | | | | Necessary | |
| --- | --- | --- | --- | --- | --- | --- |
|  | HMDI (mass %) | HD (mass ppm) | 11-1, 11-2 (mass ppm) | TMP (mass ppm) | catalyst quantity (mass ppm) | Result of evaluation of weatherability |
| Example B27 | 98.1 | 10200 | — | — | 100 | A |
| Example B28 | 98.3 | 12800 | — | — | 120 | A |
| Example B29 | 98.2 | 13200 | — | — | 150 | A |
| Example B30 | 98.1 | 14200 | — | — | 180 | A |
| Example B31 | 98.1 | 15100 | — | — | 230 | A |
| Example B32 | 98.0 | 18200 | — | — | 240 | A |
| Example B33 | 99.2 | 1400 | 630 | — | 65 | A |
| Example B34 | 99.1 | 1500 | 430 | 120 | 55 | A |
| Comparative Example B3 | 99.1 | 3.0 | — | — | 920 | B |
| Comparative Example B4 | 98.5 | 23000 | — | — | 1200 | B |

Example B35

A polyisocyanate composition comprising 99.1 mass % of hexamethylene diisocyanate and 22 mass ppm of n-pentadecane was prepared.

The isocyanurate compound was prepared in the similar manner as Example B1, and the catalyst quantity was 210 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound, which was a polymer of hexamethylene diisocyanate.

Examples B36 to B49

An isocyanurate-forming reaction was carried out in a similar manner as Example B1 except that the content of hexamethylene diisocyanate and the content of n-pentadecane in the polyisocyanate composition were changed as illustrated in Table 11.

Example B50

A polyisocyanate composition comprising 98.2 mass % of hexamethylene diisocyanate, 180 mass ppm of n-pentadecane, and 20 mass ppm of a mixture of a compound represented by formula (12-1) and a compound represented by formula (12-2) (as two kinds of mixtures) was prepared.

[Chemical Formula 46]

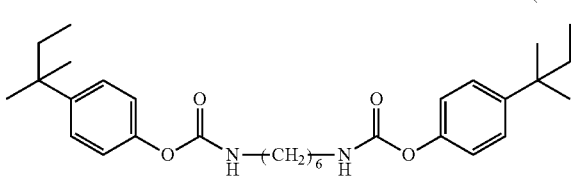

(12-1)

-continued

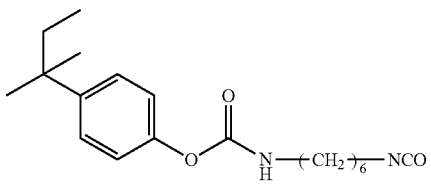

(12-2)

By using the prepared polyisocyanate composition, an isocyanurate-forming reaction was carried out in the similar manner as Example B35. In this process, the quantity of the catalyst necessary for achieving the 20% degree of conversion was 70 mass ppm with respect to the polyisocyanate composition used for the reaction.

Example B51

A polyisocyanate composition comprising 98.1 mass % of hexamethylene diisocyanate, 200 mass ppm of n-pentadecane, 20 mass ppm of 2-methylbutene, and 30 mass ppm of a mixture of a compound represented by formula (12-1) and a compound represented by formula (12-2) (as two kinds of mixtures) was prepared.

By using the prepared polyisocyanate composition, an isocyanurate-forming reaction was carried out in the similar manner as Example B35. The quantity of the catalyst necessary for achieving the 20% degree of conversion was 60 mass ppm with respect to the polyisocyanate composition used for the reaction.

Comparative Examples B5 and B6

An isocyanurate-forming reaction was carried out in a similar manner as Example B35 except that the content of hexamethylene diisocyanate and the content of benzyltoluene in the polyisocyanate composition were changed as illustrated in Table 11.

The compositions of the polyisocyanate compositions and the quantities of the catalyst necessary for achieving the 20% degree of conversion in Examples and Comparative Examples are illustrated in Table 11. In Table 11, "HMDI" denotes the content of hexamethylene diisocyanate (mass %), "PD" denotes the content of n-pentadecane (mass ppm), "12-1, 12-2" denotes the total content of a compound represented by formula (12-1) or (12-2) (mass ppm), "MB" denotes the content of 2-methylbutene (mass ppm), and the "necessary catalyst quantity" denotes the quantity of the catalyst necessary for achieving the 20% degree of conversion (the ratio to the total quantity of polyisocyanate composition in mass ppm).

TABLE 11

| | Isocyanate composition | | | | Necessary catalyst quantity (mass ppm) | Result of evaluation of weatherability |
|---|---|---|---|---|---|---|
| | HMDI (mass %) | PD (mass ppm) | 12-1, 12-2 (mass ppm) | MB (mass ppm) | | |
| Example B35 | 99.1 | 22 | — | — | 210 | A |
| Example B36 | 99.0 | 43 | — | — | 190 | A |
| Example B37 | 98.4 | 56 | — | — | 160 | A |
| Example B38 | 98.0 | 92 | — | — | 130 | A |
| Example B39 | 98.4 | 105 | — | — | 110 | A |
| Example B40 | 98.2 | 220 | — | — | 100 | A |
| Example B41 | 98.5 | 310 | — | — | 90 | A |
| Example B42 | 98.8 | 2100 | — | — | 95 | A |
| Example B43 | 98.9 | 9100 | — | — | 98 | A |
| Example B44 | 98.1 | 10300 | — | — | 100 | A |
| Example B45 | 98.0 | 12200 | — | — | 110 | A |
| Example B46 | 98.1 | 13300 | — | — | 140 | A |
| Example B47 | 98.1 | 14300 | — | — | 180 | A |
| Example B48 | 98.0 | 15300 | — | — | 200 | A |
| Example B49 | 98.0 | 18400 | — | — | 220 | A |
| Example B50 | 98.2 | 180 | 20 | — | 70 | A |
| Example B51 | 98.1 | 200 | 30 | 20 | 60 | A |
| Comparative Example B5 | 99.1 | 2.0 | — | — | 930 | B |
| Comparative Example B6 | 98.8 | 24000 | — | — | 300 | B |

Example B52

A polyisocyanate composition comprising 98.8 mass % of hexamethylene diisocyanate and 120 mass ppm of dibenzyl ether was prepared.

The isocyanurate compound was prepared in the similar manner as Example B1, and the catalyst quantity was 230 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound, which was a polymer of hexamethylene diisocyanate.

Example B53

A polyisocyanate composition comprising 98.2 mass % of hexamethylene diisocyanate, 130 mass ppm of dibenzyl ether, and 10 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B52. In this process, the quantity of the catalyst necessary for achieving the 20% degree of conversion was 65 mass ppm of with respect to the polyisocyanate composition used for the reaction.

Example B54

A polyisocyanate composition comprising 98.9 mass % of hexamethylene diisocyanate, 22 mass ppm of dibenzyl ether, 10 mass ppm of n-octene, and 10 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B52. The quantity of the catalyst necessary for achieving the 20% degree of conversion was 55 mass ppm with respect to the polyisocyanate composition used for the reaction.

The compositions of the polyisocyanate compositions and the quantities of the catalyst necessary for achieving the 20% degree of conversion in Examples and Comparative Examples are illustrated in Table 12. Note that in Table 12, "HMDI" denotes the content of hexamethylene diisocyanate (mass %), "DBE" denotes the content of dibenzyl ether (mass ppm), "11-1, 11-2" denotes the total content of a compound represented by formula (11-1) or (11-2) (mass ppm), "NO" denotes the content of n-octene (mass ppm), and the "necessary catalyst quantity" denotes the quantity of the catalyst necessary for achieving the 20% degree of conversion (the ratio to the total quantity of polyisocyanate composition in mass ppm).

TABLE 12

| | Isocyanate composition | | | | Necessary catalyst quantity (mass ppm) | Result of evaluation of weatherability |
|---|---|---|---|---|---|---|
| | HMDI (mass %) | DBE (mass ppm) | 11-1, 11-2 (mass ppm) | NO (mass ppm) | | |
| Example B52 | 98.8 | 120 | — | — | 230 | A |
| Example B53 | 98.2 | 130 | 10 | — | 65 | A |
| Example B54 | 98.9 | 22 | 10 | 10 | 55 | A |

Example B55

A polyisocyanate composition comprising 98.5 mass % of hexamethylene diisocyanate and 130 mass ppm of decyl ether was prepared.

The isocyanurate compound was prepared in the similar manner as Example B1, and the catalyst quantity was 120 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound, which was a polymer of hexamethylene diisocyanate.

Example B56

A polyisocyanate composition comprising 98.4 mass % of hexamethylene diisocyanate, 160 mass ppm of decyl ether, and 20 mass ppm of a mixture of a compound represented by formula (11-1) and a compound represented by formula (11-2) (as two kinds of mixtures) was prepared.

By using the prepared polyisocyanate composition, an isocyanurate-forming reaction was carried out in the similar manner as Example B55. In this process, the quantity of the catalyst necessary for achieving the 20% degree of conversion was 55 mass ppm with respect to the polyisocyanate composition used for the reaction.

Example B57

A polyisocyanate composition comprising 99.1 mass % of hexamethylene diisocyanate, 190 mass ppm of decyl ether, 25 mass ppm of styrene, and 25 mass ppm of a mixture of a compound represented by formula (9-1) and a compound represented by formula (9-2) (as two kinds of mixtures) was prepared.

By using the prepared polyisocyanate composition, an isocyanurate-forming reaction was carried out in the similar manner as Example B55. The quantity of the catalyst necessary for achieving the 20% degree of conversion was 50 mass ppm with respect to the polyisocyanate composition used for the reaction.

The compositions of the polyisocyanate compositions and the quantities of the catalyst necessary for achieving the 20% degree of conversion in Examples and Comparative Examples are illustrated in Table 13. Note that in Table 13, "HMDI" denotes the content of hexamethylene diisocyanate (mass %), "DE" denotes the content of decyl ether (mass ppm), "9-1, 9-2" denotes the total content of a compound represented by formula (9-1) or (9-2) (mass ppm), "ST" denotes the content of styrene (mass ppm), and the "necessary catalyst quantity" denotes the quantity of the catalyst necessary for achieving the 20% degree of conversion (the ratio to the total quantity of polyisocyanate composition in mass ppm).

TABLE 13

|  | Isocyanate composition | | | | Necessary catalyst | Result of |
|---|---|---|---|---|---|---|
|  | HMDI (mass %) | DE (mass ppm) | 9-1, 9-2 (mass ppm) | ST (mass ppm) | quantity (mass ppm) | evaluation of weatherability |
| Example B55 | 98.5 | 130 | — | — | 120 | A |
| Example B56 | 98.4 | 160 | 20 | — | 55 | A |
| Example B57 | 99.1 | 190 | 25 | 25 | 50 | A |

Example B58

A polyisocyanate composition comprising 99.1 mass % of isophorone diisocyanate and 500 mass ppm of butyl phenyl ether was prepared.

The isocyanurate compound was prepared in the similar manner as Example B1, and the catalyst quantity was 100 mass ppm with respect to the polyisocyanate composition used for the reaction.

After the reaction was complete, the reaction liquid was filtered, then unreacted isophorone diisocyanate was removed at 180° C. (27 Pa) for the first distillation and at 170° C. (13 Pa) for the second distillation by using a flow-down type thin film distillation apparatus to obtain an isocyanurate compound, which was a polymer of isophorone diisocyanate.

Example B59

A polyisocyanate composition comprising 99.2 mass % of isophorone diisocyanate, 450 mass ppm of butyl phenyl ether, and 30 mass ppm of a compound represented by formula (13-1) was prepared.

[Chemical Formula 47]

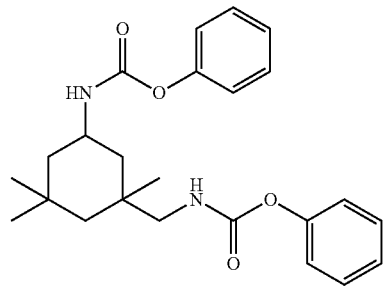

(13-1)

By using the prepared polyisocyanate composition, an isocyanurate-forming reaction was carried out in the similar manner as Example B58. In this process, the quantity of the catalyst necessary for achieving the 20% degree of conversion was 65 mass ppm with respect to the polyisocyanate composition used for the reaction.

Example B60

A polyisocyanate composition comprising 98.4 mass % of isophorone diisocyanate, 390 mass ppm of butyl phenyl ether, 20 mass ppm of nonene, and 30 mass ppm of a compound represented by formula (13-1) was prepared.

By using the prepared polyisocyanate composition, an isocyanurate-forming reaction was carried out in the similar manner as Example B58. The quantity of the catalyst necessary for achieving the 20% degree of conversion was 55 mass ppm with respect to the polyisocyanate composition used for the reaction.

The compositions of the polyisocyanate compositions and the quantities of the catalyst necessary for achieving the 20% degree of conversion in Examples and Comparative Examples are illustrated in Table 14. Note that in Table 14, "IPDI" denotes the content of isophorone diisocyanate (mass %), "BPE" denotes the content of butyl phenyl ether (mass ppm), "13-1" denotes the content of a compound represented by formula (13-1) (mass ppm), "NN" denotes the content of nonene (mass ppm), and the "necessary catalyst quantity" denotes the quantity of the catalyst necessary for achieving the 20% degree of conversion (the ratio to the total quantity of polyisocyanate composition in mass ppm).

By using the prepared polyisocyanate composition, an isocyanurate-forming reaction was carried out in the similar manner as Example B61. In this process, the quantity of the catalyst necessary for achieving the 20% degree of conversion was 85 mass ppm with respect to the polyisocyanate composition used for the reaction.

Example B63

A polyisocyanate composition comprising 98.8 mass % of isophorone diisocyanate, 50 mass ppm of o-dichlorobenzene, 40 mass ppm of α-methylstyrene, and 15 mass ppm of a compound represented by formula (13-1) was prepared.

By using the prepared polyisocyanate composition, an isocyanurate-forming reaction was carried out in the similar manner as Example B61. The quantity of the catalyst necessary for achieving the 20% degree of conversion was 70 mass ppm with respect to the polyisocyanate composition used for the reaction.

The compositions of the polyisocyanate compositions and the quantities of the catalyst necessary for achieving the

TABLE 14

| | Isocyanate composition | | | Necessary catalyst | Result of |
|---|---|---|---|---|---|
| | IPDI (mass %) | BPE (mass ppm) | 13-1 (mass ppm) | NN (mass ppm) | quantity (mass ppm) | evaluation of weatherability |
| Example B58 | 99.1 | 500 | — | — | 100 | A |
| Example B59 | 99.2 | 450 | 30 | — | 65 | A |
| Example B60 | 98.4 | 390 | 30 | 20 | 55 | A |

Example B61

A polyisocyanate composition comprising 99.0 mass % of isophorone diisocyanate and 50 mass ppm of o-dichlorobenzene was prepared.

The isocyanurate compound was prepared in the similar manner as Example B1, and the catalyst quantity was 220 mass ppm with respect to the polyisocyanate composition used for the reaction.

After the reaction was complete, the reaction liquid was filtered, then unreacted isophorone diisocyanate was removed at 180° C. (27 Pa) for the first distillation and at 170° C. (13 Pa) for the second distillation by using a flow-down type thin film distillation apparatus to obtain an isocyanurate compound, which was a polymer of isophorone diisocyanate.

Example B62

A polyisocyanate composition comprising 98.8 mass % of isophorone diisocyanate, 50 mass ppm of o-dichlorobenzene, and 15 mass ppm of a compound represented by formula (13-1) was prepared.

20% degree of conversion in Examples and Comparative Examples are illustrated in Table 15. Note that in Table 15, "IPDI" denotes the content of isophorone diisocyanate (mass %), "OD" denotes the content of o-dichlorobenzene (mass ppm), "13-1" denotes the content of a compound represented by formula (13-1) (mass ppm), "αMS" denotes the content of α-methylstyrene (mass ppm), and the "necessary catalyst quantity" denotes the quantity of the catalyst necessary for achieving the 20% degree of conversion (the ratio to the total quantity of polyisocyanate composition in mass ppm).

TABLE 15

| | Isocyanate composition | | | | Necessary catalyst | Result of |
|---|---|---|---|---|---|---|
| | IPDI (mass %) | OD (mass ppm) | 13-1 (mass ppm) | αMS (mass ppm) | quantity (mass ppm) | evaluation of weatherability |
| Example B61 | 99.0 | 50 | — | — | 220 | A |
| Example B62 | 98.8 | 50 | 15 | — | 85 | A |
| Example B63 | 98.8 | 50 | 15 | 40 | 70 | A |

Example B64

A polyisocyanate composition comprising 98.2 mass % of isophorone diisocyanate and 120 mass ppm of decamethyl tetrasiloxane was prepared.

The isocyanurate compound was prepared in the similar manner as Example B1, and the catalyst quantity was 100 mass ppm with respect to the polyisocyanate composition used for the reaction.

After the reaction was complete, the reaction liquid was filtered, then unreacted isophorone diisocyanate was removed at 180° C. (27 Pa) for the first distillation and at 170° C. (13 Pa) for the second distillation by using a flow-down type thin film distillation apparatus to obtain an isocyanurate compound, which was a polymer of isophorone diisocyanate.

Example B65

A polyisocyanate composition comprising 98.4 mass % of isophorone diisocyanate, 200 mass ppm of decamethyl tetrasiloxane, and 40 mass ppm of a compound represented by formula (14-1) was prepared.

[Chemical Formula 48]

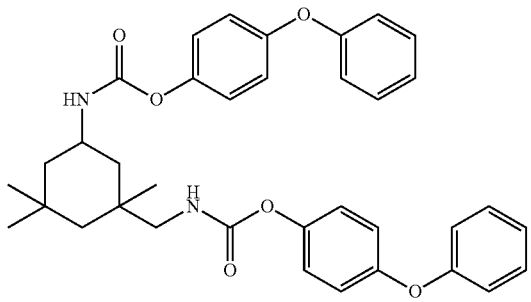

(14-1)

By using the prepared polyisocyanate composition, an isocyanurate-forming reaction was carried out in the similar manner as Example B64. In this process, the quantity of the catalyst necessary for achieving the 20% degree of conversion was 65 mass ppm with respect to the polyisocyanate composition used for the reaction.

Example B66

A polyisocyanate composition comprising 98.3 mass % of isophorone diisocyanate, 180 mass ppm of decamethyl tetrasiloxane, 50 mass ppm of n-octene, and 40 mass ppm of a compound represented by formula (14-1) was prepared.

By using the prepared polyisocyanate composition, an isocyanurate-forming reaction was carried out in the similar manner as Example 64. The quantity of the catalyst necessary for achieving the 20% degree of conversion was 55 mass ppm with respect to the polyisocyanate composition used for the reaction.

The compositions of the polyisocyanate compositions and the quantities of the catalyst necessary for achieving the 20% degree of conversion in Examples and Comparative Examples are illustrated in Table 16. Note that in Table 16, "IPDI" denotes the content of isophorone diisocyanate (mass %), "DMTS" denotes the content of decamethyl tetrasiloxane (mass ppm), "14-1" denotes the content of a compound represented by formula (14-1) (mass ppm), "NO" denotes the content of n-octene (mass ppm), and the "necessary catalyst quantity" denotes the quantity of the catalyst necessary for achieving the 20% degree of conversion (the ratio to the total quantity of polyisocyanate composition in mass ppm).

TABLE 16

| | Isocyanate composition | | | | Necessary catalyst | Result of |
|---|---|---|---|---|---|---|
| | IPDI (mass %) | DMTS (mass ppm) | 14-1 (mass ppm) | NO (mass ppm) | quantity (mass ppm) | evaluation of weatherability |
| Example B64 | 98.2 | 120 | — | — | 100 | A |
| Example B65 | 98.4 | 200 | 40 | — | 65 | A |
| Example B66 | 98.3 | 180 | 40 | 50 | 55 | A |

Example B67

A polyisocyanate composition comprising 98.2 mass % of hexamethylene diisocyanate and 150 mass ppm of dibenzyl ether was prepared.

The isocyanurate compound was prepared in the similar manner as Example B1, and the catalyst quantity was 100 mass ppm with respect to the polyisocyanate composition used for the reaction.

After the reaction was complete, the reaction liquid was filtered, then unreacted hexamethylene diisocyanate was removed at 160° C. (27 Pa) for the first distillation and at 150° C. (13 Pa) for the second distillation by using a flow-down type thin film distillation apparatus to obtain an isocyanurate compound, which was a polymer of hexamethylene diisocyanate.

Example B68

A polyisocyanate composition comprising 98.3 mass % of hexamethylene diisocyanate, 130 mass ppm of dibenzyl ether, and 60 mass ppm of a mixture of a compound represented by formula (15-1) and a compound represented by formula (15-2) (as two kinds of mixtures) was prepared.

[Chemical Formula 49]

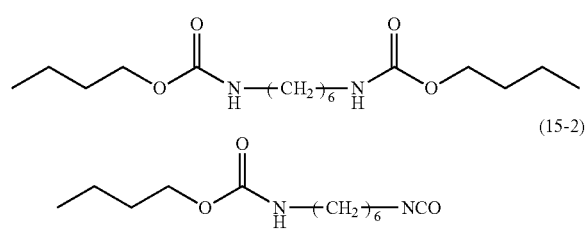

(15-1)

(15-2)

By using the prepared polyisocyanate composition, an isocyanurate-forming reaction was carried out in the similar manner as Example B67. In this process, the quantity of the catalyst necessary for achieving the 20% degree of conversion was 65 mass ppm with respect to the polyisocyanate composition used for the reaction.

Example B69

A polyisocyanate composition comprising 98.1 mass % of hexamethylene diisocyanate, 130 mass ppm of dibenzyl ether, 60 mass ppm of di-n-butyl carbonate, and 80 mass ppm of mixture of a compound represented by formula (15-1) and a compound represented by formula (15-2) (as two kinds of mixtures) was prepared.

By using the prepared polyisocyanate composition, an isocyanurate-forming reaction was carried out in the similar manner as Example B67. The quantity of the catalyst necessary for achieving the 20% degree of conversion was 55 mass ppm with respect to the polyisocyanate composition used for the reaction.

The compositions of the polyisocyanate compositions and the quantities of the catalyst necessary for achieving the 20% degree of conversion in Examples are illustrated in Table 17. Note that in Table 17, "HMDI" denotes the content of hexamethylene diisocyanate (mass %), "DBE" denotes the content of dibenzyl ether (mass ppm), "15-1, 15-2" denotes the total content of a compound represented by formula (15-1) or (15-2) (mass ppm), "DBC" denotes the content of di-n-butyl carbonate (mass ppm), and the "necessary catalyst quantity" denotes the quantity of the catalyst necessary for achieving the 20% degree of conversion (the ratio to the total quantity of polyisocyanate composition in mass ppm of).

(16-2)

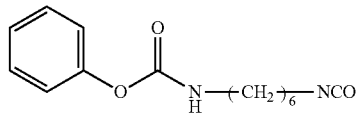

Step (1-1)

The inside of a four-neck flask to which a stirrer, a thermometer, a cooling tube, and a FT-IR probe (a product of Mettler-Toledo International Inc., React-IR, an AgX probe) had been previously attached was substituted with nitrogen, then the prepared polyisocyanate composition (1,200 g) and polyester polyol "Placcel 305" (the name of a product of DAICEL Corporation) induced from trihydric alcohol and ε-caprolactone (130 g) were placed in the flask, and then the mixture was heated at 130° C. while stirring. The reaction liquid was allowed to react while verifying the formation of the urethane group by FT-IR, and the completion of the reaction was confirmed after about 1.7 hours from the start.

Step (1-2)

Subsequently, a solution of zirconyl 2-ethylhexanoate in 20% octanol (0.5 g) was added to carry out an allophanate-forming reaction. When the rise in the refractive index of the reaction liquid reached 0.0051, a solution of 10% solid content of pyrophosphoric acid in 2-ethyl-1-hexanol (a solution prepared by diluting a product of Taihei Chemical Industrial Co., Ltd. (product name: "phosphoric acid

TABLE 17

| | Isocyanate composition | | | Necessary catalyst | Result of |
|---|---|---|---|---|---|
| | HMDI (mass %) | DBE (mass ppm) | 15-1, 15-2 (mass ppm) | DBC (mass ppm) | quantity (mass ppm) | evaluation of weatherability |
| Example B67 | 98.2 | 150 | — | — | 100 | A |
| Example B68 | 98.3 | 130 | 60 | — | 65 | A |
| Example B69 | 98.1 | 130 | 80 | 60 | 55 | A |

Example C1

Preparation of Polyisocyanate Composition

A polyisocyanate composition comprising 98.8 mass % of hexamethylene diisocyanate and 3.5 mass ppm of a mixture of a compound represented by formula (16-1) and a compound represented by formula (16-2) (two kinds of mixtures) (note that the term "mass ppm" denotes "×10⁻⁴ mass % of") was prepared.

[Chemical Formula 50]

(16-1)

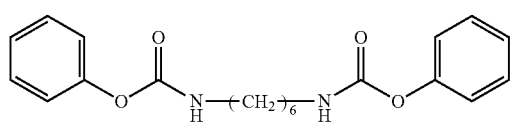

(105%)") with 2-ethyl-1-hexanol) (3.9 g) was added, and then the reaction was terminated.

The reaction liquid was filtered, then distilled at 160° C. and 0.027 kPa by using a thin film distillation apparatus (a product of Sibata Scientific Technology Ltd., heat transfer area: 0.1 m²), and then the residue was recovered. The residue was further distilled at 150° C. and 0.013 kPa by using the thin film distillation apparatus to recover the residue.

The resultant residue was a polyisocyanate composition with the yield of 280 g and the NCO content by percentage (NCO %) of 14.9%, and the Hazen color number (APHA) of the resultant polyisocyanate was 90. In addition, 1.5 mass % of hexamethylene diisocyanate remained in the obtained polyisocyanate composition.

Examples C2 to C12

Steps (1-1) and (1-2) were carried out in the similar manner as Example C1 except that the content of hexamethylene diisocyanate and the content of the compound represented by formulae (16-1) and (16-2) in the polyisocyanate composition were changed as illustrated in Table 18 to obtain a polyisocyanate composition. Note that in the respective Examples, the time taken from the start of the urethane-forming reaction to the completion of the reaction in Step (1-1) was as illustrated in Table 18.

The NCO %, Hazen color number (APHA), and the amount of remaining hexamethylene diisocyanate of the polyisocyanate compositions obtained in the respective Examples were as illustrated in Table 19.

Example C13

An isocyanate composition comprising 98.1 mass % of hexamethylene diisocyanate, and 400 mass ppm of a compound represented by formulae (16-1) and (16-2), and 1,100 mass ppm of α-methylstyrene was prepared. Steps (1-1) and (1-2) were performed in the similar manner as Example C1 except that the prepared polyisocyanate composition was used to obtain a polyisocyanate composition. Note that in Step (1-1), the time taken from the start of the urethane-forming reaction to the completion of the reaction was 0.5 hours.

The NCO %, Hazen color number (APHA), and the amount of remaining hexamethylene diisocyanate of the resultant polyisocyanate composition were as illustrated in Table 19.

Example C14

A polyisocyanate composition comprising 98.1 mass % of hexamethylene diisocyanate, and 420 mass ppm of a compound represented by formulae (16-1) and (16-2), 930 mass ppm of α-methylstyrene, and 620 ppm of benzyltoluene (an isomer mixture) was prepared. Steps (1-1) and (1-2) were performed in the similar manner as Example C1 except that the prepared isocyanate composition was used to obtain a polyisocyanate composition. Note that in Step (1-1), the time taken from the start of the urethane-forming reaction to the completion of the reaction was 0.5 hours.

The NCO %, Hazen color number (APHA), and the amount of remaining hexamethylene diisocyanate of the resultant polyisocyanate composition were as illustrated in Table 19. Furthermore, in Example C14, the time taken for Step (1-1) was as illustrated in Table 18.

Comparative Examples C1 and C2

Steps (1-1) and (1-2) were carried out in the similar manner as Example C1 except that the content of hexamethylene diisocyanate and the content of the compound represented by formulae (16-1) and (16-2) in the polyisocyanate composition were changed as illustrated in Table 18 to obtain a polyisocyanate composition. Note that in the respective Comparative Examples, the time taken from the start of the urethane-forming reaction to the completion of the reaction in Step (1-1) was as illustrated in Table 18.

The NCO %, Hazen color number (APHA), and the amount of remaining hexamethylene diisocyanate of the polyisocyanate compositions obtained in the respective Comparative Examples were as illustrated in Table 19.

Note that in Table 18, "HMDI" denotes the content of hexamethylene diisocyanate (mass %), "16-1, 16-2" denotes the total content of a compound represented by formula (16-1) or (16-2) (mass ppm), "αMS" denotes the content of α-methylstyrene (mass ppm), "BT" denotes the content of benzyltoluene (mass ppm), and "Step (1-1)" denotes the time taken from the start of the urethane-forming reaction to the completion of the reaction (hours) in Step (1-1). In Table 19, "amount of remaining HMDI" denotes the amount of hexamethylene diisocyanate remaining in the polyisocyanate composition (mass %).

TABLE 18

| | Isocyanate composition | | | | |
|---|---|---|---|---|---|
| | HMDI (mass %) | 16-1, 16-2 (mass ppm) | αMS (mass ppm) | BT (mass ppm) | Step (1-1) (hours) |
| Example C1 | 98.8 | 3.5 | — | — | 1.7 |
| Example C2 | 98.7 | 4.1 | — | — | 1.7 |
| Example C3 | 98.1 | 5.5 | — | — | 1.3 |
| Example C4 | 98.3 | 12 | — | — | 0.8 |
| Example C5 | 98.5 | 380 | — | — | 0.5 |
| Example C6 | 98.2 | 930 | — | — | 0.5 |
| Example C7 | 98.5 | 1200 | — | — | 0.4 |
| Example C8 | 98.1 | 2800 | — | — | 0.4 |
| Example C9 | 98.1 | 3200 | — | — | 0.3 |
| Example C10 | 98.3 | 4700 | — | — | 0.3 |
| Example C11 | 98.4 | 5100 | — | — | 0.3 |
| Example C12 | 98.2 | 9300 | — | — | 0.2 |
| Example C13 | 98.1 | 400 | 1100 | — | 0.5 |
| Example C14 | 98.1 | 420 | 930 | 620 | 0.5 |
| Comparative Example C1 | 98.3 | 1.2 | — | — | 2.5 |
| Comparative Example C2 | 98.5 | 12000 | — | — | 0.1 |

TABLE 19

| | NCO CONTENT (%) | Hazen color number (APHA) | Amount of remaining HMDI (mass %) |
|---|---|---|---|
| Example C1 | 14.9 | 90 | 1.5 |
| Example C2 | 15.0 | 80 | 1.2 |
| Example C3 | 14.9 | 70 | 1.3 |
| Example C4 | 15.0 | 60 | 1.4 |
| Example C5 | 15.0 | 60 | 1.3 |
| Example C6 | 15.1 | 60 | 1.3 |
| Example C7 | 14.9 | 70 | 1.5 |
| Example C8 | 14.8 | 70 | 1.5 |
| Example C9 | 13.5 | 80 | 1.6 |
| Example C10 | 13.0 | 80 | 1.5 |
| Example C11 | 12.0 | 90 | 1.2 |
| Example C12 | 11.8 | 90 | 1.7 |
| Example C13 | 14.9 | 50 | 1.2 |
| Example C14 | 14.9 | 50 | 0.2 |
| Comparative Example C1 | 15.1 | 120 | 1.6 |
| Comparative Example C2 | 10.0 | 130 | 1.6 |

Example C15

Preparation of Polyisocyanate Composition

A polyisocyanate composition comprising 98.2 mass % of hexamethylene diisocyanate and 3.0 mass ppm of a mixture of a compound represented by formula (17-1) and a compound represented by formula (17-2) (two kinds of mixtures) (note that the term "mass ppm" denotes "$\times 10^{-4}$ mass %") was prepared.

[Chemical Formula 51]

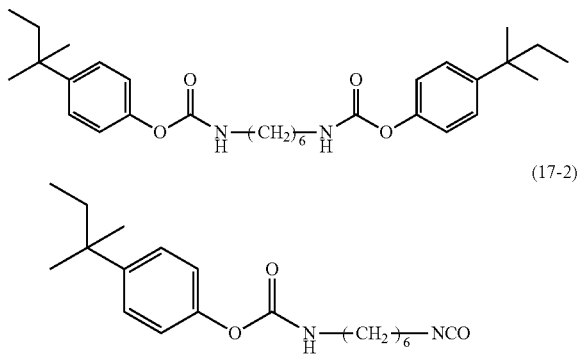

Step (2-1)

The inside of a four-neck flask to which a stirrer, a thermometer, a cooling tube, and a FT-IR probe (a product of Mettler-Toledo International Inc., React-IR, an AgX probe) had been previously attached was substituted with nitrogen, then the prepared polyisocyanate composition (1,200 g) and polyester polyol "Placcel 305" (the name of a product of DAICEL Corporation) induced from trihydric alcohol and ε-caprolactone (130 g) were placed in the flask, and then the mixture was heated at 130° C. while stirring. The reaction liquid was allowed to react while verifying the formation of the urethane group by FT-IR, and the completion of the reaction was confirmed after about 1.6 hours from the start.

Step (2-2)

Subsequently, a solution of zirconyl 2-ethylhexanoate in 20% of octanol (0.5 g) was added to carry out an allophanate-forming reaction. When the rise in the refractive index of the reaction liquid reached 0.0051, a solution of 10% of solid content of pyrophosphoric acid in 2-ethyl-1-hexanol (a solution prepared by diluting a product of Taihei Chemical Industrial Co., Ltd. (product name: "phosphoric acid (105%)") with 2-ethyl-1-hexanol) (4.0 g) was added, and then the reaction was terminated.

The reaction liquid was filtered, then distilled at 160° C. and 0.027 kPa by using a thin film distillation apparatus (a product of Sibata Scientific Technology Ltd., heat transfer area: 0.1 m$^2$), and then the residue was recovered. The residue was further distilled at 150° C. and 0.013 kPa by using the thin film distillation apparatus to recover the residue.

The resultant residue was a polyisocyanate composition with the yield of 280 g and the NCO content by percentage (NCO %) of 15.0%, and the Hazen color number (APHA) of the resultant polyisocyanate was 40. In addition, 1.4 mass % of hexamethylene diisocyanate remained in the obtained polyisocyanate composition.

Examples C16 to C26

Steps (2-1) and (2-2) were carried out in the similar manner as Example C15 except that the content of hexamethylene diisocyanate and the content of the compound represented by formulae (17-1) and (17-2) in the polyisocyanate composition were changed as illustrated in Table 20 to obtain a polyisocyanate composition. Note that in the respective Examples, the time taken from the start of the urethane-forming reaction to the completion of the reaction in Step (2-1) was as illustrated in Table 20.

The NCO %, Hazen color number (APHA), and the amount of remaining hexamethylene diisocyanate of the polyisocyanate compositions obtained in the respective Examples were as illustrated in Table 21.

Example C27

An isocyanate composition comprising 98.6 mass % of hexamethylene diisocyanate, and 300 mass ppm of a compound represented by formulae (17-1) and (17-2), and 700 mass ppm of 2,4,4-trimethylpentene-1 was prepared. Steps (2-1) and (2-2) were performed in the similar manner as Example C15 except that the prepared polyisocyanate composition was used to obtain a polyisocyanate composition. Note that in Step (2-1), the time taken from the start of the urethane-forming reaction to the completion of the reaction was 0.4 hours.

The NCO %, Hazen color number (APHA), and the amount of remaining hexamethylene diisocyanate of the resultant polyisocyanate composition were as illustrated in Table 21.

Example C28

A polyisocyanate composition comprising 99.0 mass % of hexamethylene diisocyanate, and 220 mass ppm of a compound represented by formulae (17-1) and (17-2), 500 mass ppm of 2,4,4-trimethylpentene-1, and 100 ppm of n-pentadecane was prepared. Steps (2-1) and (2-2) were performed in the similar manner as Example C15 except that the prepared isocyanate composition was used to obtain a polyisocyanate composition. Note that in Step (2-1), the time taken from the start of the urethane-forming reaction to the completion of the reaction was 0.5 hours.

The NCO %, Hazen color number (APHA), and the amount of remaining hexamethylene diisocyanate of the resultant polyisocyanate composition were as illustrated in Table 21. Furthermore, in Example C28, the time taken for Step (2-1) was as illustrated in Table 20.

Comparative Examples C3 and C4

Steps (2-1) and (2-2) were carried out in the similar manner as Example C15 except that the content of hexamethylene diisocyanate and the content of the compound represented by formulae (17-1) and (17-2) in the polyisocyanate composition were changed as illustrated in Table 20 to obtain a polyisocyanate composition. Note that in the respective Comparative Examples, the time taken from the start of the urethane-forming reaction to the completion of the reaction in Step (2-1) was as illustrated in Table 20.

The NCO %, Hazen color number (APHA), and the amount of remaining hexamethylene diisocyanate of the polyisocyanate compositions obtained in the respective Comparative Examples were as illustrated in Table 21.

Note that in Table 20, "HMDI" denotes the content of hexamethylene diisocyanate (mass %), "17-1, 17-2" denotes the total content of a compound represented by formula (17-1) or (17-2) (mass ppm), "TMP" denotes the content of 2,4,4-trimethylpentene-1 (mass ppm), "PD" denotes the content of n-pentadecane (mass ppm), and "Step (2-1)" denotes the time taken from the start of the urethane-forming reaction to the completion of the reaction (hours) in Step (2-1). In Table 21, "amount of remaining HMDI" denotes the amount of hexamethylene diisocyanate remaining in the polyisocyanate composition (mass %).

TABLE 20

| | Isocyanate composition | | | | |
|---|---|---|---|---|---|
| | HMDI (mass %) | 17-1, 17-2 (mass ppm) | TMP (mass ppm) | PD (mass ppm) | Step (2-1) (hours) |
| Example C15 | 98.2 | 3.0 | — | — | 1.6 |
| Example C16 | 98.2 | 4.2 | — | — | 1.6 |
| Example C17 | 98.4 | 5.0 | — | — | 1.2 |
| Example C18 | 99.1 | 15 | — | — | 0.9 |
| Example C19 | 99.2 | 400 | — | — | 0.4 |
| Example C20 | 98.7 | 950 | — | — | 0.4 |
| Example C21 | 98.2 | 1300 | — | — | 0.4 |
| Example C22 | 98.4 | 2900 | — | — | 0.4 |
| Example C23 | 98.4 | 3100 | — | — | 0.2 |
| Example C24 | 98.4 | 4700 | — | — | 0.2 |
| Example C25 | 98.2 | 5200 | — | — | 0.2 |

TABLE 20-continued

| | Isocyanate composition | | | | |
|---|---|---|---|---|---|
| | HMDI (mass %) | 17-1, 17-2 (mass ppm) | TMP (mass ppm) | PD (mass ppm) | Step (2-1) (hours) |
| Example C26 | 98.1 | 9700 | — | — | 0.2 |
| Example C27 | 98.6 | 300 | 700 | — | 0.4 |
| Example C28 | 99.0 | 220 | 500 | 100 | 0.5 |
| Comparative Example C3 | 98.2 | 0.2 | — | — | 2.7 |
| Comparative Example C4 | 98.1 | 14000 | — | — | 0.1 |

TABLE 21

| | NCO CONTENT (%) | Hazen color number (APHA) | Amount of remaining HMDI (mass %) |
|---|---|---|---|
| Example C15 | 15.0 | 40 | 1.4 |
| Example C16 | 15.1 | 30 | 1.2 |
| Example C17 | 15.2 | 20 | 1.2 |
| Example C18 | 15.0 | 10 | 1.4 |
| Example C19 | 15.0 | 10 | 1.2 |
| Example C20 | 14.9 | 5 | 1.5 |
| Example C21 | 15.1 | 20 | 1.2 |
| Example C22 | 15.0 | 20 | 1.3 |
| Example C23 | 14.8 | 30 | 1.1 |
| Example C24 | 14.0 | 30 | 1.1 |
| Example C25 | 15.0 | 40 | 1.3 |
| Example C26 | 14.8 | 20 | 1.4 |
| Example C27 | 14.9 | 10 | 1.1 |
| Example C28 | 15.0 | 50 | 1.2 |

TABLE 21-continued

| | NCO CONTENT (%) | Hazen color number (APHA) | Amount of remaining HMDI (mass %) |
|---|---|---|---|
| Comparative Example C3 | 15.1 | 90 | 1.4 |
| Comparative Example C4 | 12.0 | 90 | 1.2 |

Example C29

Preparation of Polyisocyanate Composition

A polyisocyanate composition comprising 99.0 mass % of hexamethylene diisocyanate and 100 mass ppm of a mixture of a compound represented by formula (18-1) and a compound represented by formula (18-2) (two kinds of mixtures) (note that the term "mass ppm" denotes "×10$^{-4}$ mass %") was prepared.

[Chemical Formula 52]

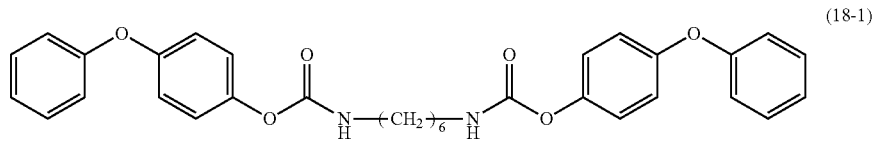
(18-1)

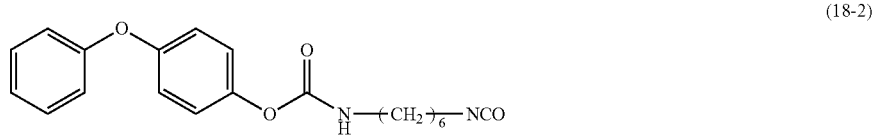
(18-2)

Step (3-1)

The inside of a four-neck flask to which a stirrer, a thermometer, a cooling tube, and a FT-IR probe (a product of Mettler-Toledo International Inc., React-IR, an AgX probe) had been previously attached was substituted with nitrogen, then the prepared polyisocyanate composition (1,200 g) and polyester polyol "Placcel 305" (the name of a product of DAICEL Corporation) induced from trihydric alcohol and ε-caprolactone (130 g) were placed in the flask, and then the mixture was heated at 130° C. while stirring. The reaction liquid was allowed to react while verifying the formation of the urethane group by FT-IR, and the completion of the reaction was confirmed after about 1.8 hours from the start.

Step (3-2)

Subsequently, a solution of zirconyl 2-ethylhexanoate in 20% of octanol (0.5 g) was added to carry out an allophanate-forming reaction. When the rise in the refractive index of the reaction liquid reached 0.0051, a solution of 10% of solid content of pyrophosphoric acid in 2-ethyl-1-hexanol (a solution prepared by diluting a product of Taihei Chemical Industrial Co., Ltd. (product name: "phosphoric acid (105%)") with 2-ethyl-1-hexanol) (3.9 g) was added, and then the reaction was terminated.

The reaction liquid was filtered, then distilled at 160° C. and 0.027 kPa by using a thin film distillation apparatus (a product of Sibata Scientific Technology Ltd., heat transfer area: 0.1 m$^2$), and then the residue was recovered. The residue was further distilled at 150° C. and 0.013 kPa by using the thin film distillation apparatus to recover the residue.

The resultant residue was a polyisocyanate composition with the yield of 280 g and the NCO content by percentage (NCO %) of 14.9%, and the Hazen color number (APHA) of the resultant polyisocyanate was 30. In addition, 1.4 mass % of hexamethylene diisocyanate remained in the obtained polyisocyanate composition.

Example C30

An isocyanate composition comprising 98.3 mass % of hexamethylene diisocyanate, and 100 mass ppm of a compound represented by formulae (18-1) and (18-2), and 100 mass ppm of styrene was prepared. Steps (3-1) and (3-2) were performed in the similar manner as Example C29 except that the prepared polyisocyanate composition was used to obtain a polyisocyanate composition. Note that in Step (3-1), the time taken from the start of the urethane-forming reaction to the completion of the reaction was 0.5 hours.

The NCO %, Hazen color number (APHA), and the amount of remaining hexamethylene diisocyanate of the resultant polyisocyanate composition were as illustrated in Table 22.

Example C31

A polyisocyanate composition comprising 98.3 mass % of hexamethylene diisocyanate, and 120 mass ppm of a compound represented by formulae (18-1) and (18-2), 130 mass ppm of styrene, and 220 ppm of dibenzyl ether was prepared. Steps (3-1) and (3-2) were performed in the similar manner as Example C29 except that the prepared isocyanate composition was used to obtain a polyisocyanate composition. Note that in Step (3-1), the time taken from the start of the urethane-forming reaction to the completion of the reaction was 0.5 hours.

The NCO %, Hazen color number (APHA), and the amount of remaining hexamethylene diisocyanate of the resultant polyisocyanate composition were as illustrated in Table 23. Furthermore, in Example C31, the time taken for Step (3-1) was as illustrated in Table 22.

Note that in Table 22, "HMDI" denotes the content of hexamethylene diisocyanate (mass %), "18-1, 18-2" denotes the total content of a compound represented by formula (18-1) or (18-2) (mass ppm), "ST" denotes the content of styrene (mass ppm), "DBE" denotes the content of dibenzyl ether (mass ppm), and "Step (3-1)" denotes the time taken from the start of the urethane-forming reaction to the completion of the reaction (hours) in Step (3-1). In Table 23, "amount of remaining HMDI" denotes the amount of hexamethylene diisocyanate remaining in the polyisocyanate composition (mass %).

TABLE 22

| | Isocyanate composition | | | | |
| --- | --- | --- | --- | --- | --- |
| | HMDI (mass %) | 18-1, 18-2 (mass ppm) | ST (mass ppm) | DBE (mass ppm) | Step (3-1) (hours) |
| Example C29 | 99.0 | 100 | — | — | 1.8 |
| Example C30 | 98.3 | 100 | 100 | — | 0.5 |
| Example C31 | 98.3 | 120 | 130 | 220 | 0.5 |

TABLE 23

| | NCO CONTENT (%) | Hazen color number (APHA) | Amount of remaining HMDI (mass %) |
| --- | --- | --- | --- |
| Example C29 | 14.9 | 30 | 1.4 |
| Example C30 | 14.9 | 20 | 1.2 |
| Example C31 | 14.9 | 20 | 1.0 |

Example C32

Preparation of Polyisocyanate Composition

A polyisocyanate composition comprising 98.3 mass % of isophorone diisocyanate and 80 mass ppm of a compound represented by formula (19-1) (note that the term "mass ppm" denotes "×10$^{-4}$ mass %") was prepared.

[Chemical Formula 53]

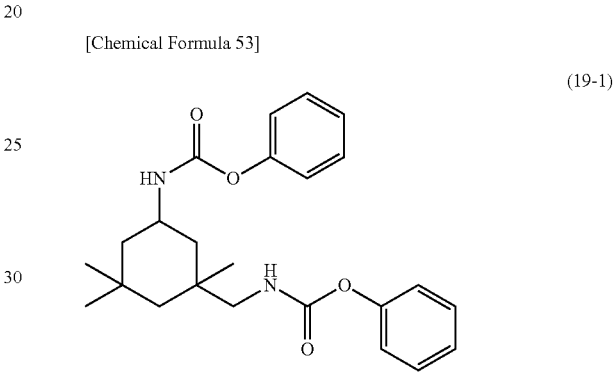

(19-1)

Step (4-1)

The inside of a four-neck flask to which a stirrer, a thermometer, a cooling tube, and a FT-IR probe (a product of Mettler-Toledo International Inc., React-IR, an AgX probe) had been previously attached was substituted with nitrogen, then the prepared polyisocyanate composition (1,200 g) and polyester polyol "Placcel 305" (the name of a product of DAICEL Corporation) induced from trihydric alcohol and ε-caprolactone (170 g) were placed in the flask, and then the mixture was heated at 130° C. while stirring. The reaction liquid was allowed to react while verifying the formation of the urethane group by FT-IR, and the completion of the reaction was confirmed after about 1.7 hours from the start.

Step (4-2)

Subsequently, a solution of zirconyl 2-ethylhexanoate in 20% of octanol (0.5 g) was added to carry out an allophanate-forming reaction. When the rise in the refractive index of the reaction liquid reached 0.0051, a solution of 10% of solid content of pyrophosphoric acid in 2-ethyl-1-hexanol (a solution prepared by diluting a product of Taihei Chemical Industrial Co., Ltd. (product name: "phosphoric acid (105%)") with 2-ethyl-1-hexanol) (3.9 g) was added, and then the reaction was terminated.

The reaction liquid was filtered, then distilled at 180° C. and 0.027 kPa by using a thin film distillation apparatus (a product of Sibata Scientific Technology Ltd., heat transfer area: 0.1 m$^2$), and then the residue was recovered. The residue was further distilled at 170° C. and 0.013 kPa by using the thin film distillation apparatus to recover the residue.

The resultant residue was a polyisocyanate composition with the NCO content by percentage (NCO %) of 15.1%, and the Hazen color number (APHA) of the resultant polyisocyanate was 30. In addition, 1.5 mass % of isophorone diisocyanate remained in the obtained polyisocyanate composition.

Example C33

An isocyanate composition comprising 98.3 mass % of isophorone diisocyanate, and 80 mass ppm of a compound represented by formula (19-1), and 300 mass ppm of nonene was prepared. Steps (4-1) and (4-2) were performed in the similar manner as Example C32 except that the prepared polyisocyanate composition was used to obtain a polyisocyanate composition. Note that in Step (4-1), the time taken from the start of the urethane-forming reaction to the completion of the reaction was 0.5 hours.

The NCO %, Hazen color number (APHA), and the amount of remaining isophorone diisocyanate of the resultant polyisocyanate composition were as illustrated in Table 25.

Example C34

A polyisocyanate composition comprising 98.6 mass % of isophorone diisocyanate, and 90 mass ppm of a compound represented by formula (19-1), 130 mass ppm of nonene, and 120 ppm of decamethyl tetrasiloxane was prepared. Steps (4-1) and (4-2) were performed in the similar manner as Example C32 except that the prepared isocyanate composition was used to obtain a polyisocyanate composition. Note that in Step (4-1), the time taken from the start of the urethane-forming reaction to the completion of the reaction was 0.5 hours.

The NCO %, Hazen color number (APHA), and the amount of remaining isophorone diisocyanate of the resultant polyisocyanate composition were as illustrated in Table 25. Furthermore, in Example C34, the time taken for Step (4-1) was as illustrated in Table 24.

Note that in Table 24, "IPDI" denotes the content of isophorone diisocyanate (mass %), "19-1" denotes the content of a compound represented by formula (19-1) (mass ppm), "NN" denotes the content of nonene (mass ppm), "DMTS" denotes the content of decamethyl tetrasiloxane (mass ppm), and "Step (4-1)" denotes the time taken from the start of the urethane-forming reaction to the completion of the reaction (hours) in Step (4-1). In Table 25, "amount of remaining IPDI" denotes the amount of hexamethylene diisocyanate remaining in the polyisocyanate composition (mass %).

TABLE 24

| | Isocyanate composition | | | | |
| --- | --- | --- | --- | --- | --- |
| | IPDI (mass %) | 19-1 (mass ppm) | NN (mass ppm) | DMTS (mass ppm) | Step (4-1) (hours) |
| Example C32 | 98.3 | 80 | — | — | 1.7 |
| Example C33 | 98.3 | 80 | 300 | — | 0.5 |
| Example C34 | 98.6 | 90 | 130 | 120 | 0.5 |

TABLE 25

| | NCO CONTENT (%) | Hazen color number (APHA) | Amount of remaining IPDI (mass %) |
| --- | --- | --- | --- |
| Example C32 | 15.1 | 30 | 1.5 |
| Example C33 | 15.1 | 20 | 1.1 |
| Example C34 | 15.1 | 20 | 1.2 |

Example C35

Preparation of Polyisocyanate Composition

A polyisocyanate composition comprising 98.3 mass % of isophorone diisocyanate and 50 mass ppm of a compound represented by formula (20-1) (note that the term "mass ppm" denotes "×10$^{-4}$ mass %") was prepared.

[Chemical Formula 54]

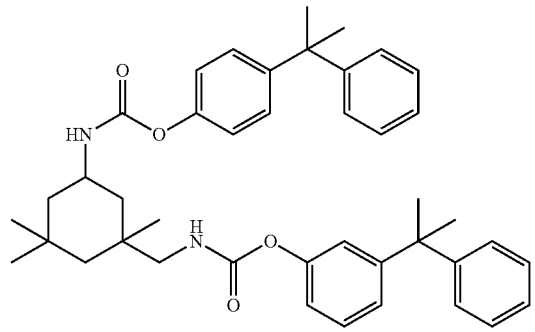

(20-1)

Step (5-1)

The inside of a four-neck flask to which a stirrer, a thermometer, a cooling tube, and a FT-IR probe (a product of Mettler-Toledo International Inc., React-IR, an AgX probe) had been previously attached was substituted with nitrogen, then the prepared polyisocyanate composition (1,200 g) and polyester polyol "Placcel 305" (the name of a product of DAICEL Corporation) induced from trihydric alcohol and ε-caprolactone (170 g) were placed in the flask, and then the mixture was heated at 130° C. while stirring. The reaction liquid was allowed to react while verifying the formation of the urethane group by FT-IR, and the completion of the reaction was confirmed after about 1.8 hours from the start.

Step (5-2) Subsequently, a solution of zirconyl 2-ethylhexanoate in 20% of octanol (0.5 g) was added to carry out an allophanate-forming reaction. When the rise in the refractive index of the reaction liquid reached 0.0051, a solution of 10% of solid content of pyrophosphoric acid in 2-ethyl-1-hexanol (a solution prepared by diluting a product of Taihei Chemical Industrial Co., Ltd. (product name: "phosphoric acid (105%)") with 2-ethyl-1-hexanol) (3.9 g) was added, and then the reaction was terminated.

The reaction liquid was filtered, then distilled at 160° C. and 0.027 kPa by using a thin film distillation apparatus (a product of Sibata Scientific Technology Ltd., heat transfer area: 0.1 m$^2$), and then the residue was recovered. The residue was further distilled at 150° C. and 0.013 kPa by using the thin film distillation apparatus to recover the residue.

The resultant residue was a polyisocyanate composition with the yield of 280 g and the NCO content by percentage (NCO %) of 14.9%, and the Hazen color number (APHA) of the resultant polyisocyanate was 30. In addition, 1.5 mass % of isophorone diisocyanate remained in the obtained polyisocyanate composition.

Example C36

An isocyanate composition comprising 98.4 mass % of isophorone diisocyanate, and 45 mass ppm of a compound represented by formula (20-1), and 40 mass ppm of α-methylstyrene was prepared. Steps (5-1) and (5-2) were performed in the similar manner as Example C35 except that the prepared polyisocyanate composition was used to obtain a polyisocyanate composition. Note that in Step (5-1), the time taken from the start of the urethane-forming reaction to the completion of the reaction was 0.5 hours.

The NCO %, Hazen color number (APHA), and the amount of remaining isophorone diisocyanate of the resultant polyisocyanate composition were as illustrated in Table 27.

Example C37

A polyisocyanate composition comprising 98.4 mass % of isophorone diisocyanate, and 50 mass ppm of a compound represented by formula (20-1), 50 mass ppm of α-methylstyrene, and 110 mass ppm of butyl phenyl ether was prepared. Steps (5-1) and (5-2) were performed in the similar manner as Example C35 except that the prepared isocyanate composition was used to obtain a polyisocyanate composition. Note that in Step (5-1), the time taken from the start of the urethane-forming reaction to the completion of the reaction was 0.5 hours.

The NCO %, Hazen color number (APHA), and the amount of remaining isophorone diisocyanate of the resultant polyisocyanate composition were as illustrated in Table 26. Furthermore, in Example C37, the time taken for Step (5-1) was as illustrated in Table 26.

Note that in Table 26, "IPDI" denotes the content of isophorone diisocyanate (mass %), "20-1" denotes the content of a compound represented by formula (20-1) (mass ppm), "αMS" denotes the content of α-methylstyrene (mass ppm), "BPE" denotes the content of butyl phenyl ether (mass ppm), and "Step (5-1)" denotes the time taken from the start of the urethane-forming reaction to the completion of the reaction (hours) in Step (5-1). In Table 27, "amount of remaining IPDI" denotes the amount of isophorone diisocyanate remaining in the polyisocyanate composition (mass %).

TABLE 26

| | Isocyanate composition | | | | |
|---|---|---|---|---|---|
| | IPDI (mass %) | 20-1 (mass ppm) | αMS (mass ppm) | BPE (mass ppm) | Step (5-1) (hours) |
| Example C35 | 98.3 | 50 | — | — | 1.8 |
| Example C36 | 98.4 | 45 | 40 | — | 0.5 |
| Example C37 | 98.4 | 50 | 50 | 110 | 0.5 |

TABLE 27

| | NCO CONTENT (%) | Hazen color number (APHA) | Amount of remaining IPDI (mass %) |
|---|---|---|---|
| Example C35 | 14.9 | 30 | 1.5 |
| Example C36 | 14.9 | 20 | 1.2 |
| Example C37 | 14.9 | 20 | 1.2 |

Example D1

An isocyanate composition comprising 98.5 mass % of hexamethylene diisocyanate and 22 mass ppm of benzyltoluene (an isomer mixture) (note that the term "mass ppm" denotes "×10$^{-4}$ mass %") was prepared.

The inside of a four-neck glass flask to which a stirrer, a thermometer, a circulating cooling tube, and a nitrogen blowing tube had been previously attached was converted into a nitrogen atmosphere, then the prepared polyisocyanate composition (700 g), trimethyl phosphate (150 g), methyl cellosolve acetate (150 g), and water (15 g) (HMDI/water molar ratio=5) were poured into the flask, and the mixture liquid was maintained for 1 hour at the liquid temperature of 160° C. The resultant reaction liquid (concentration of unreacted diisocyanate monomer: 65 mass %) was fed into a scraper type thin film distiller of the degree of vacuum of 655 Pa and the temperature of 160° C. at 500 g/hr. The resultant composition of the biuret type polyisocyanate polymer of which the concentration of diisocyanate monomer was 5 mass % and the concentration of urea dimer was 1.5 mass % was maintained for 30 minutes under nitrogen atmosphere at the liquid temperature of 140° C., and the concentration of the urea dimer after that was 0.2 mass % or less and the permeability thereof was 93%. This polyisocyanate composition was fed to the scraper type thin film distiller (degree of vacuum: 67 Pa, temperature: 160° C.) again to obtain a composition of biuret type polyisocyanate polymer of the concentration of diisocyanate monomer of 0.3 mass %, the concentration of urea dimer of 0.2 mass % or less, and the Hazen color number (APHA) of 35.

Examples D2 to D8

A biuret-forming reaction was carried out in the similar manner as Example D1 except that the content of hexamethylene diisocyanate and the content of benzyltoluene in the polyisocyanate composition were changed as illustrated in Table 28. The Hazen color numbers (APHA) of the obtained polyisocyanate compositions are illustrated in Table 28.

Example D9

A polyisocyanate composition comprising 99.0 mass % of hexamethylene diisocyanate, 1,300 mass ppm of benzyltoluene (an isomer mixture), and 530 mass ppm of a mixture of a compound represented by formula (21-1) and a compound represented by formula (21-2) (as two kinds of mixtures) was prepared.

[Chemical Formula 55]

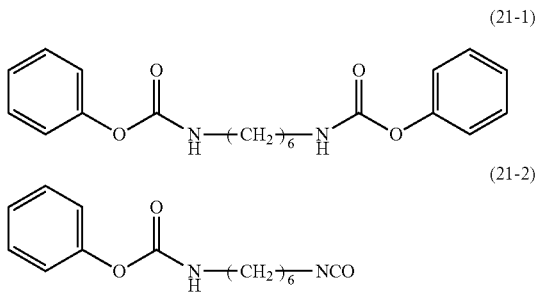

By using the prepared polyisocyanate composition, a biuret-forming reaction was carried out in the similar manner as Example D1. The Hazen color number (APHA) of the obtained polyisocyanate composition is illustrated in Table 28.

Example D10

An isocyanate composition comprising 99.0 mass % of hexamethylene diisocyanate, 1,200 mass ppm of benzyltoluene (an isomer mixture), 610 mass ppm of α-methylstyrene, and 380 mass ppm of a mixture of a compound represented by formula (21-1) and a compound represented by formula (21-2) (as two kinds of mixtures) was prepared.

By using the prepared isocyanate composition, a biuret-forming reaction was carried out in the similar manner as Example D1. The Hazen color number (APHA) of the obtained polyisocyanate composition is illustrated in Table 28.

Comparative Examples D1 and D2

A biuret-forming reaction was carried out in the similar manner as Example D1 except that the content of hexamethylene diisocyanate and the content of benzyltoluene in the isocyanate composition were changed as illustrated in Table 28. The Hazen color numbers (APHA) of the polyisocyanate compositions obtained in the respective Comparative Examples are illustrated in Table 28.

Note that in Table 28, "HMDI" denotes the content of hexamethylene diisocyanate (mass %), "BT" denotes the content of benzyltoluene (mass ppm), "21-1, 21-2" denotes the total content of a compound represented by formula (21-1) or (21-2) (mass ppm), and "αMS" denotes the content of α-methylstyrene (mass ppm).

TABLE 28

| | Isocyanate composition | | | | Hazen color number (APHA) |
|---|---|---|---|---|---|
| | HMDI (mass %) | BT (mass ppm) | 21-1, 21-2 (mass ppm) | αMS (mass ppm) | |
| Example D1 | 98.5 | 22 | — | — | 35 |
| Example D2 | 99.1 | 92 | — | — | 30 |
| Example D3 | 98.8 | 290 | — | — | 28 |
| Example D4 | 98.3 | 2400 | — | — | 31 |
| Example D5 | 98.3 | 8000 | — | — | 36 |
| Example D6 | 98.1 | 10500 | — | — | 41 |
| Example D7 | 98.1 | 15200 | — | — | 45 |
| Example D8 | 98.0 | 18300 | — | — | 48 |
| Example D9 | 99.0 | 1300 | 530 | — | 24 |
| Example D10 | 99.0 | 1200 | 380 | 610 | 25 |

TABLE 28-continued

| | Isocyanate composition | | | | Hazen color number (APHA) |
|---|---|---|---|---|---|
| | HMDI (mass %) | BT (mass ppm) | 21-1, 21-2 (mass ppm) | αMS (mass ppm) | |
| Comparative Example D1 | 99.0 | 3.5 | — | — | 55 |
| Comparative Example D2 | 97.5 | 22000 | — | — | 60 |

Example D11

An isocyanate composition comprising 98.1 mass % of hexamethylene diisocyanate and 25 mass ppm of n-pentadecane (note that the term "mass ppm" denotes "×10$^{-4}$ mass %") was prepared.

The inside of a four-neck glass flask to which a stirrer, a thermometer, a circulating cooling tube, and a nitrogen blowing tube had been previously attached was converted into a nitrogen atmosphere, then the prepared polyisocyanate composition (700 g), trimethyl phosphate (150 g), methyl cellosolve acetate (150 g), and water (15 g) (HMDI/water molar ratio=5) were poured into the flask, and the mixture liquid was maintained for 1 hour at the liquid temperature of 160° C. The resultant reaction liquid (concentration of unreacted diisocyanate monomer: 65 mass %) was fed into a scraper type thin film distiller of the degree of vacuum of 655 Pa and the temperature of 160° C. at 500 g/hr. The resultant composition of the biuret type polyisocyanate polymer of which the concentration of diisocyanate monomer was 5 mass % and the concentration of urea dimer was 1.5 mass % was maintained for 30 minutes under nitrogen atmosphere at the liquid temperature of 140° C., and the concentration of the urea dimer after that was 0.2 mass % or less and the permeability thereof was 93%. This polyisocyanate composition was fed to the scraper type thin film distiller (degree of vacuum: 67 Pa, temperature: 160° C.) again to obtain a composition of biuret type polyisocyanate polymer of the concentration of diisocyanate monomer of 0.3 mass %, the concentration of urea dimer of 0.2 mass % or less, and the Hazen color number (APHA) of 30.

Examples D12 to D18

A biuret-forming reaction was carried out in the similar manner as Example D11 except that the content of hexamethylene diisocyanate and the content of n-pentadecane in the polyisocyanate composition were changed as illustrated in Table 29. The Hazen color numbers (APHA) of the obtained polyisocyanate compositions are illustrated in Table 29.

Example D19

A polyisocyanate composition comprising 98.1 mass % of hexamethylene diisocyanate, 300 mass ppm of n-pentadecane, and 210 mass ppm of a mixture of a compound represented by formula (21-1) and a compound represented by formula (21-2) (as two kinds of mixtures) was prepared.

By using the prepared polyisocyanate composition, a biuret-forming reaction was carried out in the similar manner as Example D11. The Hazen color number (APHA) of the obtained polyisocyanate composition is illustrated in Table 29.

Example D20

An isocyanate composition comprising 98.4 mass % of hexamethylene diisocyanate, 300 mass ppm of n-pentadecane, 110 mass ppm of 2,4,4-trimethylpentene-1, and 200 mass ppm of a mixture of a compound represented by formula (21-1) and a compound represented by formula (21-2) (as two kinds of mixtures) was prepared.

By using the prepared isocyanate composition, a biuret-forming reaction was carried out in the similar manner as Example D11. The Hazen color number (APHA) of the obtained polyisocyanate composition is illustrated in Table 29.

Comparative Examples D3 and D4

A biuret-forming reaction was carried out in the similar manner as Example D11 except that the content of hexamethylene diisocyanate and the content of n-pentadecane in the isocyanate composition were changed as illustrated in Table 29. The Hazen color numbers (APHA) of the polyisocyanate compositions obtained in the respective Comparative Examples are illustrated in Table 29.

The compositions of the isocyanate compositions and the Hazen color numbers (APHA) of the obtained polyisocyanate compositions in Examples and Comparative Examples are illustrated in Table 29. Note that in Table 29, "HMDI" denotes the content of hexamethylene diisocyanate (mass %), "PD" denotes the content of n-pentadecane (mass ppm), "21-1, 21-2" denotes the total content of a compound represented by formula (21-1) or (21-2) (mass ppm), and "TMP" denotes the content of 2,4,4-trimethylpentene (mass ppm).

TABLE 29

| | Isocyanate composition | | | | Hazen color number (APHA) |
|---|---|---|---|---|---|
| | HMDI (mass %) | PD (mass ppm) | 20-1, 20-2 (mass ppm) | TMP (mass ppm) | |
| Example D11 | 98.1 | 25 | — | — | 30 |
| Example D12 | 98.9 | 93 | — | — | 25 |
| Example D13 | 98.1 | 280 | — | — | 23 |
| Example D14 | 98.1 | 2500 | — | — | 31 |
| Example D15 | 98.2 | 7500 | — | — | 33 |
| Example D16 | 98.6 | 10300 | — | — | 39 |
| Example D17 | 98.1 | 15400 | — | — | 40 |
| Example D18 | 98.0 | 18500 | — | — | 41 |
| Example D19 | 98.1 | 300 | 210 | — | 20 |
| Example D20 | 98.4 | 300 | 200 | 110 | 18 |
| Comparative Example D3 | 98.9 | 2 | — | — | 55 |
| Comparative Example D4 | 98.5 | 22000 | — | — | 63 |

The invention claimed is:

1. A polyisocyanate composition comprising, on the basis of a total mass of the polyisocyanate composition:

97 weight % or more of a polyisocyanate; and (i) 2.0 mass ppm to $1.0 \times 10^4$ mass ppm, inclusively, of one or more compounds having at least one unsaturated bond, each of which is a different compound from the polyisocyanate, wherein at least one of the one or more compounds having at least one unsaturated bond comprises a compound of formula (21);

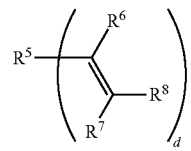

(21)

in which

R[5] represents (i) a hydrogen atom, (ii) an aliphatic group having 1 to 10 carbon atoms which is a d-valent alkyl or cycloalkyl which may be substituted with a linear alkyl group, or (iii) an aromatic group having a 6 to 10 carbon atoms;

each of R[6], R[7], and R[8] independently represents (i) a hydrogen atom, (ii) an aliphatic group having 1 to 10 carbon atoms which is selected from the group consisting of an alkyl group, a linear alkyloxy group, a cycloalkyl group, and a group comprising a linear alkyl group and a cycloalkyl group, or (iii) a mono-valent aromatic group derived from an aromatic compound selected from the group consisting of benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof, R[5], R[6], R[7], and R[8] are not simultaneously hydrogen atoms, and d represents an integer of 1 to 3, or (ii) 5.0 mass ppm to $2.0 \times 10^4$ mass ppm, inclusively, of at least one inactive compound selected from the group consisting of Compounds A, B, C, D, E, F and G, in which Compound A is an aliphatic hydrocarbon compound having a linear-chain, branched-chain, or cyclic structure;

Compound B is an aromatic hydrocarbon compound which is optionally substituted with an aliphatic hydrocarbon group;

Compound C is a compound having (i) a single ether bond or one or more sulfide bonds, and (ii) aromatic groups attached to both sides of the single ether bond or at least one of the one or more sulfide bonds, wherein the aliphatic groups may be the same or different, and a part or all of the carbon atoms of the compound is replaced by silicon atoms;

Compound D is a compound having (i) a single ether bond or one or more sulfide bonds, and (ii) aliphatic groups attached to both sides of the single ether bond or at least one of the one or more sulfide bonds, wherein the aromatic groups may be the same or different, and a part or all of the carbon atoms of the compound is replaced by silicon atoms;

Compound E is a compound having (i) a single ether bond or one or more sulfide bonds, (ii) an aliphatic group attached to one side of the single ether bond or at least one of the one or more sulfide bonds, and (iii) an aromatic group attached to another side of the single ether bond or the at least one of the one or more sulfide bonds, wherein a part or all of the carbon atoms of the compound is replaced by silicon atoms;

Compound F is a compound selected from the group consisting of aromatic hydrocarbon halides and an aliphatic hydrocarbon halides, wherein at least one aliphatic hydrocarbon hydrogen atom or at least one aromatic hydrocarbon hydrogen atom is replaced by a halogen atom; and Compound G is a compound selected from the group consisting of compounds in which a part or all of carbon atoms of the Compounds A, B and F is replaced by silicon atoms.

2. A polyisocyanate composition comprising, on the basis of a total mass of the polyisocyanate composition:

97 weight % or more of a polyisocyanate;

2.0 mass ppm to $1.0 \times 10^4$ mass ppm, inclusively, of one or more compounds having at least one unsaturated bond, wherein at least one of the one or more compounds having at least one unsaturated bond comprises at least one carbonic acid ester selected from the group consisting of dimethyl carbonate, diethyl carbonate, dibutyl carbonate, dipentyl carbonate, and dihexyl carbonate; and 5.0 mass ppm to $2.0 \times 10^4$ mass ppm, inclusively, of at least one inactive compound selected from the group consisting of Compounds A, B, C, D, E, F and G, in which Compound A is an aliphatic hydrocarbon compound having a linear-chain, branched-chain, or cyclic structure;

Compound B is an aromatic hydrocarbon compound which is optionally substituted with an aliphatic hydrocarbon group;

Compound C is a compound having (i) a single ether bond or one or more sulfide bonds, and (ii) aliphatic groups attached to both sides of the single ether bond or at least one of the one or more sulfide bonds, wherein the aliphatic groups may be the same or different, and a part or all of the carbon atoms of the compound is replaced by silicon atoms;

Compound D is a compound having (i) a single ether bond or one or more sulfide bonds, and (ii) aromatic groups attached to both sides of the single ether bond or at least one of the one or more sulfide bonds, wherein the aromatic groups may be the same or different, and a part or all of the carbon atoms of the compound is replaced by silicon atoms;

Compound E is a compound having (i) a single ether bond or one or more sulfide bonds, (ii) an aliphatic group attached to one side of the single ether bond or at least one of the one or more sulfide bonds, and (iii) an aromatic group attached to another side of the single ether bond or the at least one of the one or more sulfide bonds, wherein a part or all of the carbon atoms of the compound is replaced by silicon atoms;

Compound F is a compound selected from the group consisting of aromatic hydrocarbon halides and an aliphatic hydrocarbon halides, wherein at least one aliphatic hydrocarbon hydrogen atom or at least one aromatic hydrocarbon hydrogen atom is replaced by a halogen atom; and Compound G is a compound selected from the group consisting of compounds in which a part or all of carbon atoms of the Compounds A, B and F is replaced by silicon atoms.

3. The composition according to claim 1, wherein the composition comprises the at least one inactive compound selected from the group consisting of the Compounds A, B, C, D, E, F and G.

4. The composition according to claim 3, wherein the composition further comprises the one or more compounds having at least one unsaturated bond.

5. The composition according to claim 4, wherein the one or more compounds having at least one unsaturated bond further comprises at least one compound selected from the group consisting of formulae (23), (24) and (25):

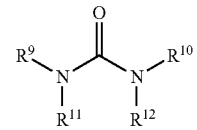

(23)

in which $R^9$, $R^{10}$, $R^{11}$ and $R^{12}$ each independently represents an aliphatic group having 1 to 20 carbon atoms, an aliphatic group substituted with an aromatic compound having 7 to 20 carbon atoms, an aromatic group having 6 to 20 carbon atoms, or a hydrogen atom, a sum of carbon numbers constituting $R^9$ and $R^{11}$ is an integer of 0 to 20, and a sum of carbon numbers constituting $R^{19}$ and $R^{12}$ is an integer of 0 to 20;

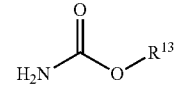

(24)

in which $R^{13}$ represents an aliphatic group having 1 to 50 carbon atoms, an aralkyl group having 7 to 50 carbon atoms, or an aromatic group having 6 to 50 carbon atoms; and

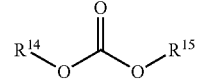

(25)

in which $R^{14}$ and $R^{15}$ each independently represents an aliphatic group having 1 to 20 carbon atoms, an aralkyl group having 7 to 50 carbon atoms, or an aromatic group having 6 to 50 carbon atoms.

6. The composition according to claim 1, wherein the inactive compound is at least one compound selected from the group consisting of benzyltoluene and hexadecane.

7. The composition according to claim 1, wherein the composition comprises the one or more compounds having at least one unsaturated bond, and the one or more compounds having at least one unsaturated bond are at least one compound selected from the group consisting of styrene, α-methylstyrene, pentene, and octene.

8. A method of suppressing or decreasing coloration in a distillation purification of a polyisocyanate, comprising:

distilling a polyisocyanate composition comprising, on the basis of a total mass of the polyisocyanate composition:

97 weight % or more of a polyisocyanate; and (i) 2.0 mass ppm to $1.0 \times 10^4$ mass ppm, inclusively, of one or more compounds having at least one unsaturated bond, each of which is a different compound from the polyisocyanate, wherein at least one of the one or more compounds having at least one unsaturated bond comprises a compound of formula (21);

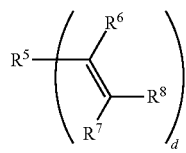
(21)

in which
R⁵ represents (i) a hydrogen atom, (ii) an aliphatic group having 1 to 10 carbon atoms which is a d-valent alkyl or cycloalkyl, or (iii) an aromatic group having a 6 to 10 carbon atoms;
each of $R^6$, $R^7$, and $R^8$ independently represents (i) a hydrogen atom, (ii) aliphatic group having 1 to 10 carbon atoms which is selected from the group consisting of an alkyl group, a linear alkyloxy group, a cycloalkyl group, a group comprising a linear alkyl group and a cycloalkyl group, or (iii) a mono-valent aromatic group derived from an aromatic compound selected from the group consisting of benzene, toluene, ethylbezene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof,
$R^5$, $R^6$, $R^7$, and $R^8$ are not simultaneously hydrogen atoms, and
d represents an integer of 1 to 3, or
(ii) 5.0 mass ppm to $2.0\times10^4$ mass ppm, inclusively, of at least one inactive compound selected from the group consisting of Compounds A, B, C, D, E, F and G, in which
Compound A is an aliphatic hydrocarbon compound having a linear-chain, branched-chain, or cyclic structure;
Compound B is an aromatic hydrocarbon compound which is optionally substituted with an aliphatic hydrocarbon group;
Compound C is a compound having (i) a single ether bond or one or more sulfide bonds, and (ii) aliphatic groups attached to both sides of the single ether bond or at least one of the one or more sulfide bonds, wherein the aliphatic groups may be the same or different, and a part or all of the carbon atoms of the compound is replaced by silicon atoms;
Compound D is a compound having (i) a single ether bond or one or more sulfide bonds, and (ii) aromatic groups attached to both sides of the single ether bond or at least one of the one or more sulfide bonds, wherein the aromatic groups may be the same or different, and a part or all of the carbon atoms of the compound is replaced by silicon atoms;
Compound E is a compound having (i) a single ether bond or one or more sulfide bonds, (ii) an aliphatic group attached to one side of the single ether bond or at least one of the one or more sulfide bonds, and (iii) an aromatic group attached to another side of the single ether bond or the at least one of the one or more sulfide bonds, wherein a part or all of the carbon atoms of the compound is replaced by silicon atoms;
Compound F is a compound selected from the group consisting of aromatic hydrocarbon halides and aliphatic hydrocarbon halides, wherein at least one aliphatic hydrocarbon hydrogen atom or at least one aromatic hydrocarbon hydrogen atom is replaced by a halogen atom; and
Compound G is a compound selected from the group consisting of compounds in which a part or all of carbon atoms of the Compounds A, B and F is replaced by silicon atoms.

9. A manufacturing method of an isocyanate polymer comprising polymerizing a polyisocyanate comprised in a polyisocyanate composition comprising, on the basis of a total mass of the polyisocyanate composition:
97 weight % or more of a polyisocyanate; and
(i) 2.0 mass ppm to $1.0\times10^4$ mass ppm, inclusively, of one or more compounds having at least one unsaturated bond, each of which is a different compound from the polyisocyanate, wherein at least one of the one or more compounds having at least one unsaturated bond comprises a compound of formula (21);

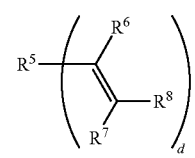
(21)

in which
R⁵ represents (i) a hydrogen atom, (ii) an aliphatic group having 1 to 10 carbon atoms which is a d-valent alkyl or cycloalkyl, or (iii) an aromatic group having a 6 to 10 carbon atoms;
each of $R^6$, $R^7$, and $R^8$ independently represents (i) a hydrogen atom, (ii) aliphatic group having 1 to 10 carbon atoms which is selected from the group consisting of an alkyl group, a linear alkyloxy group, a cycloalkyl group, a group comprising a linear alkyl group and a cycloalkyl group, or (iii) a mono-valent aromatic group derived from an aromatic compound selected from the group consisting of benzene, toluene, ethylbezene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof,
$R^5$, $R^6$, $R^7$, and $R^8$ are not simultaneously hydrogen atoms, and
d represents an integer of 1 to 3, or
(ii) 5.0 mass ppm to $2.0\times10^4$ mass ppm, inclusively, of at least one inactive compound selected from the group consisting of Compounds A, B, C, D, E, F and G, in which
Compound A is an aliphatic hydrocarbon compound having a linear-chain, branched-chain, or cyclic structure;
Compound B is an aromatic hydrocarbon compound which is optionally substituted with an aliphatic hydrocarbon group;
Compound C is a compound having (i) a single ether bond or one or more sulfide bonds, and (ii) aliphatic groups attached to both sides of the single ether bond or at least one of the one or more sulfide bonds, wherein the aliphatic groups may be the same or different, and a part or all of the carbon atoms of the compound is replaced by silicon atoms;

Compound D is a compound having (i) a single ether bond or one or more sulfide bonds, and (ii) aromatic groups attached to both sides of the single ether bond or at least one of the one or more sulfide bonds, wherein the aromatic groups may be the same or different, and a part or all of the carbon atoms of the compound is replaced by silicon atoms;

Compound E is a compound having (i) a single ether bond or one or more sulfide bonds, (ii) an aliphatic group attached to one side of the single ether bond or at least one of the one or more sulfide bonds, and (iii) an aromatic group attached to another side of the single ether bond or the at least one of the one or more sulfide bonds, wherein a part or all of the carbon atoms of the compound is replaced by silicon atoms;

Compound F is a compound selected from the group consisting of aromatic hydrocarbon halides and aliphatic hydrocarbon halides, wherein at least one aliphatic hydrocarbon hydrogen atom or at least one aromatic hydrocarbon hydrogen atom is replaced by a halogen atom; and Compound G is a compound selected from the group consisting of compounds in which a part or all of carbon atoms of the Compounds A, B and F is replaced by silicon atoms, wherein the polyisocyanate comprised in the composition is a diisocyanate, the isocyanate polymer has a unit of formula (2) and at least one unit selected from the group consisting of units of formulae (3), (4), (5), (6), (7), (8) and (9):

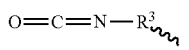 (2)

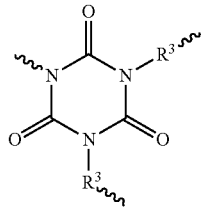 (3)

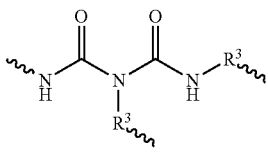 (4)

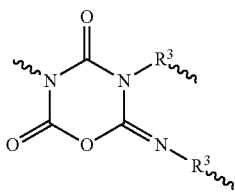 (5)

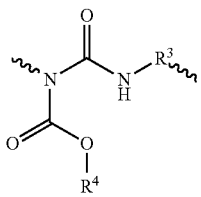 (6)

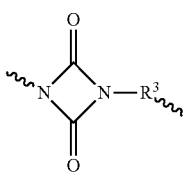 (7)

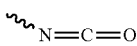 (8)

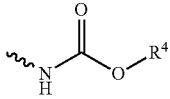 (9)

wherein $R^3$ each independently represents a divalent hydrocarbon group, and $R^4$ each independently represents a monovalent organic group.

* * * * *